(12) United States Patent
Dimmer et al.

(10) Patent No.: US 9,149,328 B2
(45) Date of Patent: Oct. 6, 2015

(54) SYSTEMS, APPARATUSES, AND METHODS FOR TREATING TISSUE AND CONTROLLING STENOSIS

(75) Inventors: Steven C. Dimmer, Bellevue, WA (US); Martin L. Mayse, University City, MO (US); Mark Deem, Mountain View, CA (US); Hanson S. Gifford, III, Woodside, CA (US)

(73) Assignee: Holaira, Inc., Plymouth, MN (US)

( * ) Notice: Subject to any disclaimer, the term of this patent is extended or adjusted under 35 U.S.C. 154(b) by 552 days.

(21) Appl. No.: 13/509,581

(22) PCT Filed: Nov. 11, 2010

(86) PCT No.: PCT/US2010/056424
§ 371 (c)(1),
(2), (4) Date: Aug. 14, 2012

(87) PCT Pub. No.: WO2011/060200
PCT Pub. Date: May 19, 2011

(65) Prior Publication Data
US 2012/0310233 A1    Dec. 6, 2012

Related U.S. Application Data

(60) Provisional application No. 61/260,349, filed on Nov. 11, 2009.

(51) Int. Cl.
*A61B 18/14*    (2006.01)
*A61B 18/18*    (2006.01)
(Continued)

(52) U.S. Cl.
CPC ......... *A61B 18/1492* (2013.01); *A61B 18/1477* (2013.01); *A61B 2018/00011* (2013.01); *A61B 2018/0016* (2013.01); *A61B 2018/0022* (2013.01); *A61B 2018/00214* (2013.01); *A61B 2018/00267* (2013.01); *A61B 2018/00434* (2013.01); *A61B 2018/00541* (2013.01); *A61B 2018/1435* (2013.01);
(Continued)

(58) Field of Classification Search
None
See application file for complete search history.

(56) References Cited

U.S. PATENT DOCUMENTS 612,724 A    10/1898    Hamilton
1,155,169 A    9/1915    Starkweather
(Continued)

FOREIGN PATENT DOCUMENTS

CA    2419228    8/2004
CN    101115448 A    1/2008
(Continued)

OTHER PUBLICATIONS

Abbott, "Present Concepts Relative to Autonomic Nerve Surgery in the Treatment of Pulmonary Disease," *American Journal of Surgery* 90:479-489, 1955.
(Continued)

*Primary Examiner* — Brian T Gedeon
(74) *Attorney, Agent, or Firm* — Patterson Thuente Pedersen, P.A.

(57) ABSTRACT

Systems, delivery devices, and methods to treat to ablate, damage, or otherwise affect tissue. The treatment systems are capable of delivering a coolable ablation assembly that ablates targeted tissue without damaging non-targeted tissue. The coolable ablation assembly damages nerve tissue to temporarily or permanently decrease nervous system input. The system, delivery devices, and methods can damage tissue and manage scarring and stenosis.

21 Claims, 29 Drawing Sheets

(51) Int. Cl.
  *A61B 18/00* (2006.01)
  *A61N 7/02* (2006.01)
  *A61N 7/00* (2006.01)

(52) U.S. Cl.
  CPC ........ *A61B 2018/1467* (2013.01); *A61N 7/022* (2013.01); *A61N 2007/003* (2013.01)

(56) References Cited

U.S. PATENT DOCUMENTS

| | | |
|---|---|---|
| 1,207,479 A | 12/1916 | Bisgaard |
| 1,216,183 A | 2/1917 | Swingle |
| 1,695,107 A | 12/1928 | Kahl |
| 2,072,346 A | 3/1937 | Smith |
| 2,279,714 A | 4/1942 | Meyerhof et al. |
| 3,320,957 A | 5/1967 | Sokolik |
| 3,568,659 A | 3/1971 | Karnegis |
| 3,667,476 A | 6/1972 | Muller |
| 3,692,029 A | 9/1972 | Adair |
| 3,918,449 A | 11/1975 | Pistor ........................ 128/218 R |
| 3,946,745 A | 3/1976 | Hsiang-Lai et al. .......... 128/421 |
| 3,949,743 A | 4/1976 | Shanbrom .................. 128/173.1 |
| 3,995,617 A | 12/1976 | Watkins et al. |
| 4,078,864 A | 3/1978 | Howell |
| 4,095,602 A | 6/1978 | Leveen |
| 4,116,589 A | 9/1978 | Rishton |
| 4,129,129 A | 12/1978 | Amrine |
| 4,154,246 A | 5/1979 | Leveen |
| 4,277,168 A | 7/1981 | Oku |
| 4,305,402 A | 12/1981 | Katims ........................ 128/741 |
| 4,351,330 A | 9/1982 | Scarberry ................ 128/207.15 |
| 4,461,283 A | 7/1984 | Doi |
| 4,502,490 A | 3/1985 | Evans et al. |
| 4,503,855 A | 3/1985 | Maslanka |
| 4,503,863 A | 3/1985 | Katims ........................ 128/741 |
| 4,512,762 A | 4/1985 | Spears |
| 4,522,212 A | 6/1985 | Gelinas et al. |
| 4,557,272 A | 12/1985 | Carr |
| 4,565,200 A | 1/1986 | Cosman ........................ 128/642 |
| 4,567,882 A | 2/1986 | Heller |
| 4,573,481 A | 3/1986 | Bullara ........................ 128/784 |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,643,186 A | 2/1987 | Rosen et al. ................ 128/303.1 |
| 4,646,737 A | 3/1987 | Hussein et al. |
| 4,649,924 A | 3/1987 | Taccardi |
| 4,649,935 A | 3/1987 | Charmillot et al. ........... 128/783 |
| 4,658,836 A | 4/1987 | Turner ........................ 128/804 |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don Michael et al. |
| 4,709,698 A | 12/1987 | Johnston et al. |
| 4,739,759 A | 4/1988 | Rexroth et al. |
| 4,754,065 A | 6/1988 | Levenson et al. |
| 4,754,752 A | 7/1988 | Ginsburg et al. |
| 4,765,322 A | 8/1988 | Charmillot et al. ........... 128/783 |
| 4,765,959 A | 8/1988 | Fukasawa |
| 4,767,402 A | 8/1988 | Kost et al. ........................ 604/22 |
| 4,772,112 A | 9/1988 | Zider et al. |
| 4,773,899 A | 9/1988 | Spears |
| 4,779,614 A | 10/1988 | Moise |
| 4,784,135 A | 11/1988 | Blum et al. |
| 4,790,305 A | 12/1988 | Zoltan et al. |
| 4,799,479 A | 1/1989 | Spears |
| 4,802,492 A | 2/1989 | Grunstein |
| 4,808,164 A | 2/1989 | Hess ................ 604/95 |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,881,542 A | 11/1989 | Schmidt et al. .......... 128/207.14 |
| 4,895,557 A | 1/1990 | Moise et al. |
| 4,902,129 A | 2/1990 | Siegmund et al. |
| 4,904,472 A | 2/1990 | Belardinelli et al. ......... 514/263 |
| 4,906,229 A | 3/1990 | Wampler |
| 4,907,589 A | 3/1990 | Cosman |
| 4,908,012 A | 3/1990 | Moise et al. |
| 4,920,978 A | 5/1990 | Colvin |
| 4,944,722 A | 7/1990 | Carriker et al. |
| 4,945,910 A | 8/1990 | Budyko et al. ................ 128/421 |
| 4,955,377 A | 9/1990 | Lennox et al. ................ 128/401 |
| 4,967,765 A | 11/1990 | Turner et al. |
| 4,969,865 A | 11/1990 | Hwang et al. |
| 4,976,709 A | 12/1990 | Sand |
| 4,985,014 A | 1/1991 | Orejola |
| 4,989,604 A | 2/1991 | Fang ............................ 128/421 |
| 4,991,603 A | 2/1991 | Cohen et al. |
| 4,992,474 A | 2/1991 | Skidmore et al. ............. 514/653 |
| 5,005,559 A | 4/1991 | Blanco et al. |
| 5,007,908 A | 4/1991 | Rydell ............................ 606/47 |
| 5,009,636 A | 4/1991 | Wortley et al. |
| 5,009,936 A | 4/1991 | Yamanaka et al. |
| 5,010,892 A | 4/1991 | Colvin et al. |
| 5,019,075 A | 5/1991 | Spears et al. |
| 5,027,829 A | 7/1991 | Larsen |
| 5,030,645 A | 7/1991 | Kollonitsch |
| 5,036,848 A | 8/1991 | Hewson |
| 5,053,033 A | 10/1991 | Clarke |
| 5,054,486 A | 10/1991 | Yamada ........................ 128/421 |
| 5,056,519 A | 10/1991 | Vince |
| 5,056,529 A | 10/1991 | de Groot ........................ 128/754 |
| 5,057,107 A | 10/1991 | Parins et al. ...................... 606/48 |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,106,360 A | 4/1992 | Ishiwara et al. |
| 5,107,830 A | 4/1992 | Younes |
| 5,107,835 A | 4/1992 | Thomas .................... 128/419 R |
| 5,109,846 A | 5/1992 | Thomas ........................ 128/421 |
| 5,114,423 A | 5/1992 | Kasprzyk et al. |
| 5,116,864 A | 5/1992 | March et al. |
| 5,117,828 A | 6/1992 | Metzger et al. ................ 128/642 |
| 5,123,413 A | 6/1992 | Hasegawa et al. ........ 128/419 G |
| 5,126,375 A | 6/1992 | Skidmore et al. ............. 514/651 |
| 5,135,480 A | 8/1992 | Bannon et al. .................. 604/20 |
| 5,135,517 A | 8/1992 | McCoy |
| 5,139,029 A | 8/1992 | Fishman et al. ............... 128/743 |
| 5,151,100 A | 9/1992 | Abele et al. ...................... 606/28 |
| 5,152,286 A | 10/1992 | Sitko et al. ...................... 128/422 |
| 5,165,420 A | 11/1992 | Strickland |
| 5,167,223 A | 12/1992 | Koros et al. |
| 5,170,802 A | 12/1992 | Mehra |
| 5,170,803 A | 12/1992 | Hewson et al. |
| 5,174,288 A | 12/1992 | Bardy et al. |
| 5,188,602 A | 2/1993 | Nichols |
| 5,190,540 A | 3/1993 | Lee .................. 606/28 |
| 5,191,883 A | 3/1993 | Lennox et al. |
| 5,213,576 A | 5/1993 | Abiuso et al. |
| 5,215,103 A | 6/1993 | Desai |
| 5,224,491 A | 7/1993 | Mehra |
| 5,225,445 A | 7/1993 | Skidmore et al. ............. 514/651 |
| 5,231,996 A | 8/1993 | Bardy et al. |
| 5,232,444 A | 8/1993 | Just et al. |
| 5,234,456 A | 8/1993 | Silvestrini |
| 5,239,982 A | 8/1993 | Trauthen |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,286,254 A | 2/1994 | Shapland et al. ................ 604/21 |
| 5,292,331 A | 3/1994 | Boneau |
| 5,293,869 A | 3/1994 | Edwards et al. |

(56) References Cited

U.S. PATENT DOCUMENTS

| | | | |
|---|---|---|---|
| 5,309,910 A | 5/1994 | Edwards et al. | |
| 5,311,866 A | 5/1994 | Kagan et al. | |
| 5,313,943 A | 5/1994 | Houser et al. | |
| 5,324,255 A | 6/1994 | Passafaro et al. | 604/22 |
| 5,324,284 A | 6/1994 | Imran | |
| 5,343,936 A | 9/1994 | Beatenbough et al. | |
| 5,344,398 A | 9/1994 | Hara | 604/96 |
| 5,345,936 A | 9/1994 | Pomeranz et al. | |
| 5,348,554 A | 9/1994 | Imran et al. | 606/41 |
| 5,366,443 A | 11/1994 | Eggers et al. | |
| 5,368,591 A | 11/1994 | Lennox et al. | |
| 5,370,644 A | 12/1994 | Langberg | |
| 5,370,675 A | 12/1994 | Edwards et al. | 607/101 |
| 5,370,679 A | 12/1994 | Atlee, III | |
| 5,372,603 A | 12/1994 | Acker et al. | 606/194 |
| 5,374,287 A | 12/1994 | Rubin | |
| 5,379,765 A | 1/1995 | Kajiwara et al. | |
| 5,383,917 A | 1/1995 | Desai et al. | |
| 5,393,207 A | 2/1995 | Maher et al. | |
| 5,394,880 A | 3/1995 | Atlee, III | |
| 5,396,887 A | 3/1995 | Imran | |
| 5,400,778 A | 3/1995 | Jonson et al. | |
| 5,400,783 A | 3/1995 | Pomeranz et al. | |
| 5,405,362 A | 4/1995 | Kramer et al. | 607/5 |
| 5,405,366 A | 4/1995 | Fox et al. | 607/50 |
| 5,411,025 A | 5/1995 | Webster, Jr. | |
| 5,415,166 A | 5/1995 | Imran | |
| 5,415,656 A | 5/1995 | Tihon et al. | |
| 5,417,687 A | 5/1995 | Nardella et al. | |
| 5,422,362 A | 6/1995 | Vincent et al. | |
| 5,423,744 A | 6/1995 | Gencheff et al. | |
| 5,423,811 A | 6/1995 | Imran et al. | |
| 5,425,023 A | 6/1995 | Haraguchi et al. | |
| 5,425,703 A | 6/1995 | Feiring | |
| 5,425,811 A | 6/1995 | Mashita | |
| 5,431,696 A | 7/1995 | Atlee, III | |
| 5,433,730 A | 7/1995 | Alt | |
| 5,437,665 A | 8/1995 | Munro | |
| 5,443,470 A | 8/1995 | Stern et al. | |
| 5,454,782 A | 10/1995 | Perkins | |
| 5,454,840 A | 10/1995 | Krakovsky et al. | 607/39 |
| 5,456,667 A | 10/1995 | Ham et al. | |
| 5,458,596 A | 10/1995 | Lax et al. | |
| 5,465,717 A | 11/1995 | Imran et al. | |
| 5,470,352 A | 11/1995 | Rappaport | |
| 5,471,982 A | 12/1995 | Edwards et al. | |
| 5,474,530 A | 12/1995 | Passafaro et al. | |
| 5,478,309 A | 12/1995 | Sweezer et al. | |
| 5,478,578 A | 12/1995 | Arnold et al. | 424/499 |
| 5,496,271 A | 3/1996 | Burton et al. | 604/54 |
| 5,496,304 A | 3/1996 | Chasan | 606/1 |
| 5,496,311 A | 3/1996 | Abele et al. | |
| 5,496,312 A | 3/1996 | Klicek | |
| 5,500,011 A | 3/1996 | Desai | |
| 5,505,728 A | 4/1996 | Ellman et al. | |
| 5,505,730 A | 4/1996 | Edwards | |
| 5,507,791 A | 4/1996 | Sitko | |
| 5,509,419 A | 4/1996 | Edwards et al. | |
| 5,522,862 A | 6/1996 | Testerman et al. | |
| 5,531,779 A | 7/1996 | Dahl et al. | |
| 5,540,681 A | 7/1996 | Strul et al. | |
| 5,540,730 A | 7/1996 | Terry, Jr. et al. | 607/40 |
| 5,545,161 A | 8/1996 | Imran | |
| 5,545,193 A | 8/1996 | Fleischman et al. | |
| 5,547,469 A | 8/1996 | Rowland et al. | |
| 5,549,559 A | 8/1996 | Eshel | |
| 5,549,655 A | 8/1996 | Erickson | |
| 5,549,661 A | 8/1996 | Kordis et al. | |
| RE35,330 E | 9/1996 | Malone et al. | |
| 5,553,611 A | 9/1996 | Budd et al. | |
| 5,558,073 A | 9/1996 | Pomeranz et al. | |
| 5,562,608 A | 10/1996 | Sekins et al. | 604/20 |
| 5,571,074 A | 11/1996 | Buckman, Jr. et al. | |
| 5,571,088 A | 11/1996 | Lennox et al. | 604/96 |
| 5,574,059 A | 11/1996 | Regunathan et al. | |
| 5,578,072 A | 11/1996 | Barone et al. | |
| 5,582,609 A | 12/1996 | Swanson et al. | |
| 5,588,432 A | 12/1996 | Crowley | |
| 5,588,812 A | 12/1996 | Taylor et al. | |
| 5,595,183 A | 1/1997 | Swanson et al. | |
| 5,598,848 A | 2/1997 | Swanson et al. | |
| 5,599,345 A | 2/1997 | Edwards et al. | |
| 5,601,088 A | 2/1997 | Swanson et al. | |
| 5,605,157 A | 2/1997 | Panescu et al. | |
| 5,607,419 A | 3/1997 | Amplatz et al. | |
| 5,607,462 A | 3/1997 | Imran | |
| 5,620,438 A | 4/1997 | Amplatz et al. | |
| 5,620,463 A | 4/1997 | Drolet | 607/3 |
| 5,623,940 A | 4/1997 | Daikuzono | |
| 5,624,392 A | 4/1997 | Saab | |
| 5,624,439 A | 4/1997 | Edwards et al. | |
| 5,626,618 A | 5/1997 | Ward et al. | |
| 5,630,425 A | 5/1997 | Panescu et al. | |
| 5,630,794 A | 5/1997 | Lax et al. | |
| 5,630,813 A | 5/1997 | Kieturakis | |
| 5,634,471 A | 6/1997 | Fairfax et al. | |
| 5,641,326 A | 6/1997 | Adams | |
| 5,647,870 A | 7/1997 | Kordis et al. | |
| 5,658,278 A | 8/1997 | Imran et al. | 606/41 |
| 5,658,322 A | 8/1997 | Fleming | 607/50 |
| 5,658,549 A | 8/1997 | Akehurst et al. | 424/45 |
| 5,660,175 A | 8/1997 | Dayal | 128/207.15 |
| 5,662,108 A | 9/1997 | Budd et al. | |
| 5,669,930 A | 9/1997 | Igarashi | |
| 5,669,932 A | 9/1997 | Fischell et al. | |
| 5,674,472 A | 10/1997 | Akehurst et al. | 424/45 |
| 5,678,535 A | 10/1997 | DiMarco | |
| 5,680,860 A | 10/1997 | Imran | |
| 5,681,280 A | 10/1997 | Rusk et al. | |
| 5,681,308 A | 10/1997 | Edwards et al. | |
| 5,687,723 A | 11/1997 | Avitall | |
| 5,688,267 A | 11/1997 | Panescu et al. | |
| 5,690,692 A | 11/1997 | Fleming | 607/50 |
| 5,693,078 A | 12/1997 | Desai et al. | |
| 5,694,934 A | 12/1997 | Edelman | |
| 5,695,471 A | 12/1997 | Wampler | |
| 5,699,799 A | 12/1997 | Xu et al. | |
| 5,702,386 A | 12/1997 | Stern et al. | |
| 5,707,218 A | 1/1998 | Maher et al. | |
| 5,707,336 A | 1/1998 | Rubin | |
| 5,707,352 A | 1/1998 | Sekins et al. | |
| 5,707,400 A | 1/1998 | Terry, Jr. et al. | 607/44 |
| 5,722,401 A | 3/1998 | Pietroski et al. | |
| 5,722,403 A | 3/1998 | McGee et al. | |
| 5,722,416 A | 3/1998 | Swanson et al. | |
| 5,725,525 A | 3/1998 | Kordis | |
| 5,727,569 A | 3/1998 | Benetti et al. | |
| 5,728,094 A | 3/1998 | Edwards | |
| 5,730,128 A | 3/1998 | Pomeranz et al. | |
| 5,730,704 A | 3/1998 | Avitall | |
| 5,730,726 A | 3/1998 | Klingenstein | |
| 5,730,741 A | 3/1998 | Horzewski et al. | |
| 5,733,319 A | 3/1998 | Neilson et al. | |
| 5,735,846 A | 4/1998 | Panescu et al. | |
| 5,740,808 A | 4/1998 | Panescu et al. | |
| 5,741,248 A | 4/1998 | Stern et al. | |
| 5,746,224 A | 5/1998 | Edwards | |
| 5,752,518 A | 5/1998 | McGee et al. | |
| 5,755,714 A | 5/1998 | Murphy-Chutorian | |
| 5,755,753 A | 5/1998 | Knowlton | |
| 5,759,158 A | 6/1998 | Swanson | |
| 5,765,568 A | 6/1998 | Sweezer, Jr. et al. | |
| 5,766,605 A | 6/1998 | Sanders et al. | 424/239.1 |
| 5,769,846 A | 6/1998 | Edwards et al. | |
| 5,772,590 A | 6/1998 | Webster, Jr. | |
| 5,779,669 A | 7/1998 | Haissaguerre et al. | |
| 5,779,698 A | 7/1998 | Clayman et al. | |
| 5,782,239 A | 7/1998 | Webster, Jr. | |
| 5,782,797 A | 7/1998 | Schweich, Jr. et al. | |
| 5,782,827 A | 7/1998 | Gough et al. | |
| 5,782,848 A | 7/1998 | Lennox | |
| 5,782,899 A | 7/1998 | Imran | |
| 5,792,064 A | 8/1998 | Panescu et al. | |
| 5,795,303 A | 8/1998 | Swanson et al. | |

(56) References Cited

U.S. PATENT DOCUMENTS

| | | |
|---|---|---|
| 5,800,375 A | 9/1998 | Sweezer et al. |
| 5,800,486 A | 9/1998 | Thome et al. ............... 607/105 |
| 5,807,306 A | 9/1998 | Shapland et al. |
| 5,810,757 A | 9/1998 | Sweezer, Jr. et al. |
| 5,810,807 A | 9/1998 | Ganz et al. |
| 5,814,078 A | 9/1998 | Zhou et al. ..................... 607/1 |
| 5,817,028 A | 10/1998 | Anderson |
| 5,817,073 A | 10/1998 | Krespi ........................ 604/272 |
| 5,820,554 A | 10/1998 | Davis et al. |
| 5,820,589 A | 10/1998 | Torgerson et al. ............ 604/93 |
| 5,823,189 A | 10/1998 | Kordis |
| 5,827,277 A | 10/1998 | Edwards |
| 5,833,651 A | 11/1998 | Donovan et al. |
| 5,836,874 A | 11/1998 | Swanson et al. |
| 5,836,905 A | 11/1998 | Lemelson et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,843,088 A | 12/1998 | Barra et al. .................. 606/108 |
| 5,846,238 A | 12/1998 | Jackson et al. |
| 5,848,969 A | 12/1998 | Panescu et al. |
| 5,848,972 A | 12/1998 | Triedman et al. |
| 5,849,026 A | 12/1998 | Zhou et al. ..................... 607/90 |
| 5,855,577 A | 1/1999 | Murphy-Chutorian et al. |
| 5,860,974 A | 1/1999 | Abele ........................... 606/41 |
| 5,863,291 A | 1/1999 | Schaer |
| 5,865,791 A | 2/1999 | Whayne et al. |
| 5,868,740 A | 2/1999 | Leveen et al. |
| 5,871,443 A | 2/1999 | Edwards et al. |
| 5,871,483 A | 2/1999 | Jackson et al. ................ 606/41 |
| 5,871,523 A | 2/1999 | Fleischman et al. |
| 5,873,852 A | 2/1999 | Vigil et al. |
| 5,873,865 A | 2/1999 | Horzewski et al. |
| 5,876,340 A | 3/1999 | Tu et al. |
| 5,876,399 A | 3/1999 | Chia et al. |
| 5,881,727 A | 3/1999 | Edwards |
| 5,882,346 A | 3/1999 | Pomeranz et al. |
| 5,891,027 A | 4/1999 | Tu et al. ..................... 600/374 |
| 5,891,135 A | 4/1999 | Jackson et al. |
| 5,891,136 A | 4/1999 | McGee et al. |
| 5,891,138 A | 4/1999 | Tu et al. |
| 5,891,182 A | 4/1999 | Fleming ........................ 607/50 |
| 5,893,847 A | 4/1999 | Kordis |
| 5,893,887 A | 4/1999 | Jayaraman |
| 5,897,554 A | 4/1999 | Chia et al. |
| 5,899,882 A | 5/1999 | Waksman et al. |
| 5,902,268 A | 5/1999 | Saab ............................. 604/96 |
| 5,904,651 A | 5/1999 | Swanson et al. |
| 5,904,711 A | 5/1999 | Flom et al. |
| 5,906,636 A | 5/1999 | Casscells, III et al. |
| 5,908,445 A | 6/1999 | Whayne et al. |
| 5,908,446 A | 6/1999 | Imran |
| 5,908,839 A | 6/1999 | Levitt et al. |
| 5,911,218 A | 6/1999 | DiMarco ................. 128/200.24 |
| 5,916,235 A | 6/1999 | Guglielmi |
| 5,919,147 A | 7/1999 | Jain |
| 5,919,172 A | 7/1999 | Golba, Jr. |
| 5,924,424 A | 7/1999 | Stevens et al. |
| 5,928,228 A | 7/1999 | Kordis et al. |
| 5,931,806 A | 8/1999 | Shimada ........................ 604/24 |
| 5,931,835 A | 8/1999 | Mackey |
| 5,935,079 A | 8/1999 | Swanson et al. |
| 5,941,869 A | 8/1999 | Patterson et al. |
| 5,951,494 A | 9/1999 | Wang et al. |
| 5,951,546 A | 9/1999 | Lorentzen |
| 5,954,661 A | 9/1999 | Greenspon et al. |
| 5,954,662 A | 9/1999 | Swanson et al. |
| 5,954,717 A | 9/1999 | Behl et al. |
| 5,956,501 A | 9/1999 | Brown .................... 395/500.32 |
| 5,957,919 A | 9/1999 | Laufer ........................... 606/28 |
| 5,957,961 A | 9/1999 | Maguire et al. |
| 5,964,223 A | 10/1999 | Baran ..................... 128/207.14 |
| 5,964,753 A | 10/1999 | Edwards |
| 5,964,796 A | 10/1999 | Imran |
| 5,971,983 A | 10/1999 | Lesh |
| 5,972,026 A | 10/1999 | Laufer et al. .................... 607/96 |
| 5,976,175 A | 11/1999 | Hirano et al. |
| 5,976,709 A | 11/1999 | Kageyama et al. |
| 5,979,456 A | 11/1999 | Magovern |
| 5,980,563 A | 11/1999 | Tu et al. |
| 5,984,917 A | 11/1999 | Fleischman et al. |
| 5,984,971 A | 11/1999 | Faccioli et al. |
| 5,989,545 A | 11/1999 | Foster et al. ............... 424/183.1 |
| 5,991,650 A | 11/1999 | Swanson et al. |
| 5,992,419 A | 11/1999 | Sterzer et al. |
| 5,993,462 A | 11/1999 | Pomeranz et al. |
| 5,995,873 A | 11/1999 | Rhodes ......................... 607/46 |
| 5,997,534 A | 12/1999 | Tu et al. |
| 5,999,855 A | 12/1999 | DiMarco |
| 6,001,054 A | 12/1999 | Regulla et al. |
| 6,003,517 A | 12/1999 | Sheffield et al. |
| 6,004,269 A | 12/1999 | Crowley et al. |
| 6,006,134 A | 12/1999 | Hill et al. ......................... 607/9 |
| 6,006,755 A | 12/1999 | Edwards |
| 6,008,211 A | 12/1999 | Robinson et al. |
| 6,009,877 A | 1/2000 | Edwards |
| 6,010,500 A | 1/2000 | Sherman et al. |
| 6,014,579 A | 1/2000 | Pomeranz et al. |
| 6,016,437 A | 1/2000 | Tu et al. ..................... 600/374 |
| 6,023,638 A | 2/2000 | Swanson |
| 6,024,740 A | 2/2000 | Lesh et al. |
| 6,029,091 A | 2/2000 | De La Rama et al. |
| 6,033,397 A | 3/2000 | Laufer et al. .................... 606/27 |
| 6,036,687 A | 3/2000 | Laufer et al. |
| 6,036,689 A | 3/2000 | Tu et al. |
| 6,039,731 A | 3/2000 | Taylor et al. |
| 6,043,273 A | 3/2000 | Duhaylongsod ............... 514/478 |
| 6,045,549 A | 4/2000 | Smethers et al. |
| 6,045,550 A | 4/2000 | Simpson et al. |
| 6,050,992 A | 4/2000 | Nichols |
| 6,052,607 A | 4/2000 | Edwards et al. |
| 6,053,172 A | 4/2000 | Hovda et al. |
| 6,053,909 A | 4/2000 | Shadduck |
| 6,056,744 A | 5/2000 | Edwards |
| 6,056,745 A | 5/2000 | Panescu et al. |
| 6,056,769 A | 5/2000 | Epstein et al. |
| 6,060,454 A | 5/2000 | Duhaylongsod ................ 514/26 |
| 6,063,078 A | 5/2000 | Wittkampf |
| 6,063,768 A | 5/2000 | First ............................. 514/14 |
| 6,071,280 A | 6/2000 | Edwards et al. |
| 6,071,281 A | 6/2000 | Burnside et al. |
| 6,071,282 A | 6/2000 | Fleischman |
| 6,081,749 A | 6/2000 | Ingle et al. |
| 6,083,249 A | 7/2000 | Familoni ......................... 607/40 |
| 6,083,255 A | 7/2000 | Laufer et al. .................... 607/96 |
| 6,087,394 A | 7/2000 | Duhaylongsod ............... 514/478 |
| 6,090,104 A | 7/2000 | Webster, Jr. |
| 6,091,995 A | 7/2000 | Ingle et al. |
| 6,092,528 A | 7/2000 | Edwards |
| 6,097,985 A | 8/2000 | Kasevich et al. ............... 607/102 |
| 6,101,412 A | 8/2000 | Duhaylongsod ................. 607/2 |
| 6,102,886 A | 8/2000 | Lundquist et al. |
| 6,106,524 A | 8/2000 | Eggers et al. |
| 6,117,101 A | 9/2000 | Diederich et al. |
| 6,123,702 A | 9/2000 | Swanson et al. |
| 6,123,703 A | 9/2000 | Tu et al. |
| 6,123,718 A | 9/2000 | Tu et al. |
| 6,125,301 A | 9/2000 | Capel ............................. 607/74 |
| 6,127,410 A | 10/2000 | Duhaylongsod ............... 514/478 |
| 6,129,726 A | 10/2000 | Edwards et al. ................ 606/41 |
| 6,135,997 A | 10/2000 | Laufer et al. |
| 6,139,527 A | 10/2000 | Laufer et al. |
| 6,139,571 A | 10/2000 | Fuller et al. |
| 6,139,845 A | 10/2000 | Donovan ................... 424/236.1 |
| 6,141,589 A | 10/2000 | Duhaylongsod ................ 607/10 |
| 6,142,993 A | 11/2000 | Whayne et al. |
| 6,143,013 A | 11/2000 | Samson et al. |
| 6,143,277 A | 11/2000 | Ashurst et al. ................. 424/45 |
| 6,149,647 A | 11/2000 | Tu et al. |
| 6,152,143 A | 11/2000 | Edwards |
| 6,152,899 A | 11/2000 | Farley et al. |
| 6,152,953 A | 11/2000 | Hipskind ...................... 607/109 |
| 6,159,194 A | 12/2000 | Eggers et al. |

(56) References Cited

U.S. PATENT DOCUMENTS

| | | | |
|---|---|---|---|
| 6,163,716 A | 12/2000 | Edwards et al. | |
| 6,174,323 B1 | 1/2001 | Biggs et al. | 606/232 |
| 6,179,833 B1 | 1/2001 | Taylor | |
| 6,183,468 B1 | 2/2001 | Swanson et al. | |
| 6,197,013 B1 | 3/2001 | Reed et al. | |
| 6,198,970 B1 | 3/2001 | Freed et al. | 607/42 |
| 6,200,311 B1 | 3/2001 | Danek et al. | |
| 6,200,332 B1 | 3/2001 | Del Giglio | |
| 6,200,333 B1 | 3/2001 | Laufer | 607/96 |
| 6,203,562 B1 | 3/2001 | Ohkubo | 606/204 |
| 6,210,355 B1* | 4/2001 | Edwards et al. | 604/22 |
| 6,210,367 B1 | 4/2001 | Carr | |
| 6,212,432 B1 | 4/2001 | Matsuura | 607/76 |
| 6,212,433 B1 | 4/2001 | Behl | |
| 6,214,002 B1 | 4/2001 | Fleischman et al. | |
| 6,216,043 B1 | 4/2001 | Swanson et al. | |
| 6,216,044 B1 | 4/2001 | Kordis | |
| 6,216,704 B1 | 4/2001 | Ingle et al. | |
| 6,217,576 B1 | 4/2001 | Tu et al. | |
| 6,226,543 B1 | 5/2001 | Gilboa et al. | |
| 6,230,052 B1 | 5/2001 | Wolff et al. | 607/2 |
| 6,231,595 B1 | 5/2001 | Dobak, III | |
| 6,235,024 B1 | 5/2001 | Tu | |
| 6,240,307 B1 | 5/2001 | Beatty et al. | |
| 6,241,727 B1 | 6/2001 | Tu et al. | |
| 6,245,065 B1 | 6/2001 | Panescu et al. | |
| 6,251,368 B1 | 6/2001 | Akehurst et al. | 424/45 |
| 6,253,762 B1 | 7/2001 | Britto | 128/200.14 |
| 6,254,598 B1 | 7/2001 | Edwards et al. | 606/41 |
| 6,254,599 B1 | 7/2001 | Lesh et al. | 606/41 |
| 6,258,083 B1 | 7/2001 | Daniel et al. | 606/15 |
| 6,258,087 B1 | 7/2001 | Edwards et al. | 606/41 |
| 6,264,653 B1 | 7/2001 | Falwell | |
| 6,265,379 B1 | 7/2001 | Donovan | 514/14 |
| 6,269,813 B1 | 8/2001 | Fitzgerald et al. | |
| 6,270,476 B1 | 8/2001 | Santoianni et al. | |
| 6,273,886 B1 | 8/2001 | Edwards et al. | 606/34 |
| 6,273,907 B1 | 8/2001 | Laufer | 607/96 |
| 6,283,987 B1 | 9/2001 | Laird et al. | |
| 6,283,988 B1 | 9/2001 | Laufer et al. | 607/96 |
| 6,283,989 B1 | 9/2001 | Laufer et al. | 607/96 |
| 6,287,304 B1 | 9/2001 | Eggers et al. | |
| 6,296,639 B1 | 10/2001 | Truckai et al. | |
| 6,299,633 B1 | 10/2001 | Laufer | 607/96 |
| 6,302,870 B1 | 10/2001 | Jacobsen et al. | 604/272 |
| 6,303,509 B1 | 10/2001 | Chen et al. | 438/706 |
| 6,306,423 B1 | 10/2001 | Donovan et al. | 424/423 |
| 6,315,173 B1 | 11/2001 | Di Giovanni et al. | 222/402.2 |
| 6,315,778 B1 | 11/2001 | Gambale et al. | |
| 6,317,615 B1 | 11/2001 | KenKnight et al. | |
| 6,322,559 B1 | 11/2001 | Daulton et al. | |
| 6,322,584 B2 | 11/2001 | Ingle et al. | |
| 6,325,798 B1 | 12/2001 | Edwards et al. | 606/41 |
| 6,327,503 B1 | 12/2001 | Familoni | 607/40 |
| 6,338,727 B1 | 1/2002 | Noda et al. | |
| 6,338,836 B1 | 1/2002 | Kuth et al. | |
| 6,341,236 B1 | 1/2002 | Osorio et al. | 607/45 |
| 6,346,104 B2 | 2/2002 | Daly et al. | |
| 6,355,031 B1 | 3/2002 | Edwards et al. | |
| 6,356,786 B1 | 3/2002 | Rezai et al. | 607/45 |
| 6,356,787 B1 | 3/2002 | Rezai et al. | 607/45 |
| 6,357,447 B1 | 3/2002 | Swanson et al. | |
| 6,358,245 B1 | 3/2002 | Edwards et al. | |
| 6,358,926 B2 | 3/2002 | Donovan | 514/14 |
| 6,361,554 B1 | 3/2002 | Brisken | 623/1.1 |
| 6,363,937 B1 | 4/2002 | Hovda et al. | 128/898 |
| 6,366,814 B1 | 4/2002 | Boveja et al. | 607/45 |
| 6,379,352 B1 | 4/2002 | Reynolds et al. | |
| 6,383,509 B1 | 5/2002 | Donovan et al. | 424/423 |
| 6,394,956 B1 | 5/2002 | Chandrasekaran et al. | |
| 6,402,744 B2 | 6/2002 | Edwards et al. | 606/41 |
| 6,405,732 B1 | 6/2002 | Edwards et al. | 128/898 |
| 6,409,723 B1 | 6/2002 | Edwards | |
| 6,411,852 B1 | 6/2002 | Danek et al. | 607/42 |
| 6,414,018 B1 | 7/2002 | Duhaylongsod | 514/478 |
| 6,416,511 B1 | 7/2002 | Lesh et al. | |
| 6,416,740 B1 | 7/2002 | Unger | |
| 6,423,058 B1 | 7/2002 | Edwards et al. | 606/41 |
| 6,423,105 B1 | 7/2002 | Iijima et al. | |
| 6,424,864 B1 | 7/2002 | Matsuura | 607/3 |
| 6,425,877 B1 | 7/2002 | Edwards | 604/21 |
| 6,425,887 B1 | 7/2002 | McGuckin et al. | 604/272 |
| 6,425,895 B1 | 7/2002 | Swanson et al. | |
| 6,432,092 B2 | 8/2002 | Miller | 604/272 |
| 6,436,130 B1 | 8/2002 | Philips et al. | |
| 6,438,423 B1 | 8/2002 | Rezai et al. | 607/46 |
| 6,440,128 B1 | 8/2002 | Edwards et al. | 606/41 |
| 6,440,129 B1 | 8/2002 | Simpson | |
| 6,442,435 B2 | 8/2002 | King et al. | |
| 6,447,505 B2 | 9/2002 | McGovern et al. | 606/41 |
| 6,447,785 B1 | 9/2002 | Donovan | 424/239.1 |
| 6,448,231 B2 | 9/2002 | Graham | 514/21 |
| 6,451,013 B1* | 9/2002 | Bays et al. | 606/27 |
| 6,458,121 B1 | 10/2002 | Rosenstock et al. | |
| 6,460,545 B2 | 10/2002 | Kordis | |
| 6,464,680 B1 | 10/2002 | Brisken et al. | 604/501 |
| 6,464,697 B1 | 10/2002 | Edwards et al. | 606/41 |
| 6,475,160 B1 | 11/2002 | Sher | 600/556 |
| 6,480,746 B1 | 11/2002 | Ingle et al. | |
| 6,485,416 B1 | 11/2002 | Platt et al. | 600/300 |
| 6,488,673 B1 | 12/2002 | Laufer et al. | 604/516 |
| 6,488,679 B1 | 12/2002 | Swanson et al. | |
| 6,491,710 B2 | 12/2002 | Satake | 606/191 |
| 6,493,589 B1 | 12/2002 | Medhkour et al. | |
| 6,494,880 B1 | 12/2002 | Swanson et al. | |
| 6,496,737 B2 | 12/2002 | Rudie et al. | 607/101 |
| 6,496,738 B2 | 12/2002 | Carr | |
| 6,506,399 B2 | 1/2003 | Donovan | 424/423 |
| 6,510,969 B2 | 1/2003 | Di Giovanni et al. | 222/402.2 |
| 6,514,246 B1 | 2/2003 | Swanson et al. | |
| 6,514,290 B1 | 2/2003 | Loomas | 623/23.65 |
| 6,519,488 B2 | 2/2003 | KenKnight et al. | |
| 6,522,913 B2 | 2/2003 | Swanson et al. | |
| 6,524,555 B1 | 2/2003 | Ashurst et al. | 424/45 |
| 6,526,320 B2 | 2/2003 | Mitchell | |
| 6,526,976 B1 | 3/2003 | Baran | 128/207.14 |
| 6,529,756 B1 | 3/2003 | Phan et al. | |
| 6,532,388 B1 | 3/2003 | Hill et al. | 607/2 |
| 6,533,780 B1 | 3/2003 | Laird et al. | |
| 6,536,427 B2 | 3/2003 | Davies et al. | 128/203.15 |
| 6,544,226 B1 | 4/2003 | Gaiser et al. | |
| 6,544,262 B2 | 4/2003 | Fleischman | |
| 6,546,928 B1 | 4/2003 | Ashurst et al. | 128/200.23 |
| 6,546,932 B1 | 4/2003 | Nahon et al. | 128/898 |
| 6,546,934 B1 | 4/2003 | Ingle et al. | |
| 6,547,776 B1 | 4/2003 | Gaiser et al. | 604/506 |
| 6,547,788 B1 | 4/2003 | Maguire et al. | |
| 6,549,808 B1 | 4/2003 | Gisel et al. | 607/53 |
| 6,551,274 B2 | 4/2003 | Heiner | |
| 6,551,310 B1 | 4/2003 | Ganz et al. | 606/41 |
| 6,558,333 B2 | 5/2003 | Gilboa et al. | |
| 6,558,378 B2 | 5/2003 | Sherman et al. | |
| 6,558,381 B2 | 5/2003 | Ingle et al. | |
| 6,562,034 B2 | 5/2003 | Edwards et al. | 606/41 |
| 6,572,612 B2 | 6/2003 | Stewart et al. | |
| 6,575,623 B2 | 6/2003 | Werneth | |
| 6,575,969 B1 | 6/2003 | Rittman, III et al. | |
| 6,582,427 B1 | 6/2003 | Goble et al. | |
| 6,582,430 B2 | 6/2003 | Hall | |
| 6,587,718 B2 | 7/2003 | Talpade | |
| 6,587,719 B1 | 7/2003 | Barrett et al. | 607/2 |
| 6,587,731 B1 | 7/2003 | Ingle et al. | |
| 6,589,235 B2 | 7/2003 | Wong et al. | |
| 6,589,238 B2 | 7/2003 | Edwards et al. | |
| 6,593,130 B1 | 7/2003 | Sen et al. | |
| 6,599,311 B1 | 7/2003 | Biggs et al. | 606/232 |
| 6,601,581 B1 | 8/2003 | Babaev | 128/200.16 |
| 6,603,996 B1 | 8/2003 | Beatty et al. | |
| 6,610,054 B1 | 8/2003 | Edwards et al. | |
| 6,610,083 B2 | 8/2003 | Keller et al. | |
| 6,610,713 B2 | 8/2003 | Tracey | 514/343 |
| 6,613,002 B1 | 9/2003 | Clark et al. | |
| 6,613,045 B1 | 9/2003 | Laufer et al. | |
| 6,620,159 B2 | 9/2003 | Hegde | |

(56) References Cited

U.S. PATENT DOCUMENTS

| | | | |
|---|---|---|---|
| 6,620,415 B2 | 9/2003 | Donovan | 424/239.1 |
| 6,622,047 B2 | 9/2003 | Barrett et al. | 607/45 |
| 6,623,742 B2 | 9/2003 | Voet | 424/236.1 |
| 6,626,855 B1 | 9/2003 | Weng et al. | 601/3 |
| 6,626,903 B2 | 9/2003 | McGuckin, Jr. et al. | |
| 6,629,535 B2 | 10/2003 | Ingle et al. | |
| 6,629,951 B2 | 10/2003 | Laufer et al. | 604/96.01 |
| 6,632,440 B1 | 10/2003 | Quinn et al. | 424/239.1 |
| 6,633,779 B1 | 10/2003 | Danek et al. | 607/42 |
| 6,634,363 B1 | 10/2003 | Laufer et al. | 128/898 |
| 6,635,054 B2 | 10/2003 | Fjield et al. | |
| 6,635,056 B2 | 10/2003 | Kadhiresan et al. | |
| 6,638,273 B1 | 10/2003 | Farley et al. | |
| 6,640,119 B1 | 10/2003 | Budd et al. | |
| 6,640,120 B1 | 10/2003 | Swanson et al. | |
| 6,645,200 B1 | 11/2003 | Koblish et al. | |
| 6,645,496 B2 | 11/2003 | Aoki et al. | 424/184.1 |
| 6,647,617 B1 | 11/2003 | Beatty et al. | |
| 6,648,881 B2 | 11/2003 | KenKnight et al. | |
| 6,649,161 B1 | 11/2003 | Donovan | 424/94.5 |
| 6,652,517 B1 | 11/2003 | Hall et al. | |
| 6,652,548 B2 | 11/2003 | Evans et al. | |
| 6,656,960 B2 | 12/2003 | Puskas | 514/345 |
| 6,658,279 B2 | 12/2003 | Swanson et al. | |
| 6,663,622 B1 | 12/2003 | Foley et al. | |
| 6,666,858 B2 | 12/2003 | Lafontaine | |
| 6,669,693 B2 | 12/2003 | Friedman | |
| 6,673,068 B1 | 1/2004 | Berube | |
| 6,673,070 B2 | 1/2004 | Edwards et al. | |
| 6,675,047 B1 | 1/2004 | Konoplev et al. | 607/50 |
| 6,676,686 B2 | 1/2004 | Naganuma | 607/1 |
| 6,681,136 B2 | 1/2004 | Schuler et al. | 607/44 |
| 6,692,492 B2 | 2/2004 | Simpson et al. | |
| 6,692,494 B1 | 2/2004 | Cooper et al. | 606/46 |
| 6,699,180 B2 | 3/2004 | Kobayashi | |
| 6,699,243 B2 | 3/2004 | West et al. | |
| 6,708,064 B2 | 3/2004 | Rezai | 607/45 |
| 6,711,436 B1 | 3/2004 | Duhaylongsod | 607/9 |
| 6,712,074 B2 | 3/2004 | Edwards et al. | 128/898 |
| 6,712,812 B2 | 3/2004 | Roschak et al. | 606/41 |
| 6,712,814 B2 | 3/2004 | Edwards et al. | |
| 6,714,822 B2 | 3/2004 | King et al. | |
| 6,719,685 B2 | 4/2004 | Fujikura et al. | |
| 6,719,694 B2 | 4/2004 | Weng et al. | 600/439 |
| 6,723,053 B2 | 4/2004 | Ackerman et al. | |
| 6,723,091 B2 | 4/2004 | Goble et al. | |
| 6,728,562 B1 | 4/2004 | Budd et al. | |
| 6,735,471 B2 | 5/2004 | Hill et al. | |
| 6,735,475 B1 | 5/2004 | Whitehurst et al. | 607/46 |
| 6,740,321 B1 | 5/2004 | Donovan | 424/94.6 |
| 6,743,197 B1 | 6/2004 | Edwards | 604/103.01 |
| 6,743,413 B1 | 6/2004 | Schultz et al. | 424/45 |
| 6,749,604 B1 | 6/2004 | Eggers et al. | |
| 6,749,606 B2 | 6/2004 | Keast et al. | 606/41 |
| 6,752,765 B1 | 6/2004 | Strobel et al. | 600/536 |
| 6,755,026 B2 | 6/2004 | Wallach | |
| 6,755,849 B1 | 6/2004 | Gowda et al. | 607/89 |
| 6,767,347 B2 | 7/2004 | Sharkey et al. | |
| 6,767,544 B2 | 7/2004 | Brooks et al. | 424/247.1 |
| 6,770,070 B1 | 8/2004 | Balbierz | |
| 6,772,013 B1 | 8/2004 | Ingle et al. | |
| 6,773,711 B2 | 8/2004 | Voet et al. | 424/239.1 |
| 6,776,991 B2 | 8/2004 | Naumann | 424/239.1 |
| 6,777,423 B2 | 8/2004 | Banholzer et al. | 514/291 |
| 6,778,854 B2 | 8/2004 | Puskas | 607/2 |
| 6,780,183 B2 | 8/2004 | Jimenez et al. | |
| 6,786,889 B1 | 9/2004 | Musbach et al. | |
| 6,802,843 B2 | 10/2004 | Truckai et al. | |
| 6,805,131 B2 | 10/2004 | Kordis | |
| 6,819,956 B2 | 11/2004 | DiLorenzo | 607/45 |
| 6,826,420 B1 | 11/2004 | Beatty et al. | |
| 6,826,421 B1 | 11/2004 | Beatty et al. | |
| 6,827,931 B1 | 12/2004 | Donovan | 424/94.63 |
| 6,836,688 B2 | 12/2004 | Ingle et al. | |
| 6,837,888 B2 | 1/2005 | Ciarrocca et al. | |
| 6,838,429 B2 | 1/2005 | Paslin | 514/2 |
| 6,838,434 B2 | 1/2005 | Voet | 514/2 |
| 6,838,471 B2 | 1/2005 | Tracey | 514/343 |
| 6,840,243 B2 | 1/2005 | Deem et al. | |
| 6,841,156 B2 | 1/2005 | Aoki et al. | 424/184.1 |
| 6,843,998 B1 | 1/2005 | Steward et al. | 424/236.1 |
| 6,846,312 B2 | 1/2005 | Edwards et al. | |
| 6,847,849 B2 | 1/2005 | Mamo et al. | 607/117 |
| 6,849,073 B2 | 2/2005 | Hoey et al. | |
| 6,852,091 B2 | 2/2005 | Edwards et al. | |
| 6,852,110 B2 | 2/2005 | Roy et al. | |
| 6,861,058 B2 | 3/2005 | Aoki et al. | 424/184.1 |
| 6,866,662 B2 | 3/2005 | Fuimaono et al. | |
| 6,871,092 B2 | 3/2005 | Piccone | 607/3 |
| 6,872,206 B2 | 3/2005 | Edwards et al. | 606/41 |
| 6,872,397 B2 | 3/2005 | Aoki et al. | 424/239.1 |
| 6,878,156 B1 | 4/2005 | Noda | |
| 6,881,213 B2 | 4/2005 | Ryan et al. | |
| 6,885,888 B2 | 4/2005 | Rezai | 607/9 |
| 6,890,347 B2 | 5/2005 | Machold et al. | |
| 6,893,436 B2 | 5/2005 | Woodard et al. | |
| 6,893,438 B2 | 5/2005 | Hall et al. | |
| 6,893,439 B2 | 5/2005 | Fleischman | |
| 6,895,267 B2 | 5/2005 | Panescu et al. | |
| 6,904,303 B2 | 6/2005 | Phan et al. | |
| 6,908,462 B2 | 6/2005 | Joye et al. | |
| 6,908,928 B2 | 6/2005 | Banholzer et al. | 514/291 |
| 6,913,616 B2 | 7/2005 | Hamilton et al. | 607/89 |
| 6,917,834 B2 | 7/2005 | Koblish et al. | |
| 6,934,583 B2 | 8/2005 | Weinberg et al. | 607/9 |
| 6,937,896 B1 | 8/2005 | Kroll | 607/9 |
| 6,937,903 B2 | 8/2005 | Schuler et al. | 607/42 |
| 6,939,309 B1 | 9/2005 | Beatty et al. | |
| 6,939,345 B2 | 9/2005 | KenKnight et al. | |
| 6,939,346 B2 | 9/2005 | Kannenberg et al. | |
| 6,947,785 B1 | 9/2005 | Beatty et al. | |
| 6,954,977 B2 | 10/2005 | Maguire et al. | |
| 6,957,106 B2 | 10/2005 | Schuler et al. | 607/44 |
| 6,961,622 B2 | 11/2005 | Gilbert | 607/148 |
| 6,970,742 B2 | 11/2005 | Mann et al. | 607/23 |
| RE38,912 E | 12/2005 | Walz et al. | 424/46 |
| 6,971,395 B2 | 12/2005 | Edwards et al. | |
| 6,974,224 B2 | 12/2005 | Thomas-Benedict | 362/103 |
| 6,974,456 B2 | 12/2005 | Edwards et al. | |
| 6,974,578 B1 | 12/2005 | Aoki et al. | 424/239.1 |
| 6,978,168 B2 | 12/2005 | Beatty et al. | |
| 6,978,174 B2 | 12/2005 | Gelfand et al. | 607/3 |
| 6,990,370 B1 | 1/2006 | Beatty et al. | |
| 6,994,706 B2 | 2/2006 | Chornenky et al. | |
| 6,997,189 B2 | 2/2006 | Biggs et al. | 128/898 |
| 7,004,942 B2 | 2/2006 | Laird et al. | |
| 7,022,088 B2 | 4/2006 | Keast et al. | 601/2 |
| 7,022,105 B1 | 4/2006 | Edwards | 604/103.01 |
| 7,027,869 B2 | 4/2006 | Danek et al. | 607/42 |
| 7,043,307 B1 | 5/2006 | Zelickson et al. | |
| 7,070,800 B2 | 7/2006 | Bechtold-Peters et al. | 424/434 |
| 7,072,720 B2 | 7/2006 | Puskas | |
| 7,083,614 B2 | 8/2006 | Fjield et al. | |
| 7,101,368 B2 | 9/2006 | Lafontaine | |
| 7,101,387 B2 | 9/2006 | Garabedian et al. | 607/105 |
| 7,104,987 B2 | 9/2006 | Biggs et al. | 606/34 |
| 7,104,990 B2 | 9/2006 | Jenkins et al. | |
| 7,112,198 B2 | 9/2006 | Satake | 606/41 |
| 7,118,568 B2 | 10/2006 | Hassett et al. | |
| 7,122,031 B2 | 10/2006 | Edwards et al. | |
| 7,122,033 B2 | 10/2006 | Wood | |
| 7,125,407 B2 | 10/2006 | Edwards et al. | |
| 7,131,445 B2 | 11/2006 | Amoah | |
| 7,142,910 B2 | 11/2006 | Puskas | 607/2 |
| 7,150,745 B2 | 12/2006 | Stern et al. | |
| 7,162,303 B2 | 1/2007 | Levin et al. | 607/44 |
| 7,165,551 B2 | 1/2007 | Edwards et al. | |
| 7,167,757 B2 | 1/2007 | Ingle et al. | |
| 7,175,644 B2 | 2/2007 | Cooper et al. | 606/191 |
| 7,179,257 B2 | 2/2007 | West et al. | 606/41 |
| 7,186,251 B2 | 3/2007 | Malecki et al. | |
| 7,187,964 B2 | 3/2007 | Khoury | |
| 7,187,973 B2 | 3/2007 | Hauck | |
| 7,189,208 B1 | 3/2007 | Beatty et al. | |

(56) References Cited

U.S. PATENT DOCUMENTS

| | | |
|---|---|---|
| 7,198,635 B2 | 4/2007 | Danek et al. .................. 607/96 |
| 7,200,445 B1 | 4/2007 | Dalbec et al. ................ 607/101 |
| 7,229,469 B1 | 6/2007 | Witzel et al. |
| 7,238,357 B2 | 7/2007 | Barron ...................... 424/239.1 |
| 7,241,295 B2 | 7/2007 | Maguire ....................... 606/41 |
| 7,255,693 B1 | 8/2007 | Johnston et al. |
| RE39,820 E | 9/2007 | Banholzer et al. ............ 514/291 |
| 7,264,002 B2 | 9/2007 | Danek et al. .................. 128/898 |
| 7,266,414 B2 | 9/2007 | Cornelius et al. |
| 7,273,055 B2 | 9/2007 | Danek et al. .................. 128/898 |
| 7,289,843 B2 | 10/2007 | Beatty et al. |
| 7,291,146 B2 | 11/2007 | Steinke et al. |
| 7,292,890 B2 | 11/2007 | Whitehurst et al. ............ 607/45 |
| 7,309,707 B2 | 12/2007 | Bender et al. ................. 514/291 |
| 7,310,552 B2 | 12/2007 | Puskas .............................. 607/2 |
| RE40,045 E | 2/2008 | Palmer ............................ 424/43 |
| 7,326,207 B2 | 2/2008 | Edwards |
| 7,344,535 B2 | 3/2008 | Stern et al. |
| 7,371,231 B2 | 5/2008 | Rioux et al. |
| 7,393,330 B2 | 7/2008 | Keast et al. ........................ 601/2 |
| 7,393,350 B2 | 7/2008 | Maurice |
| 7,394,976 B2 | 7/2008 | Entenman et al. |
| 7,402,172 B2 | 7/2008 | Chin et al. |
| 7,422,563 B2 | 9/2008 | Roschak et al. .................. 601/2 |
| 7,422,584 B2 | 9/2008 | Loomas et al. .................. 606/32 |
| 7,425,212 B1 | 9/2008 | Danek et al. ..................... 606/47 |
| 7,430,449 B2 | 9/2008 | Aldrich et al. ................... 607/40 |
| 7,462,162 B2 | 12/2008 | Phan et al. ......................... 604/8 |
| 7,462,179 B2 | 12/2008 | Edwards et al. |
| 7,473,273 B2 | 1/2009 | Campbell |
| 7,477,945 B2 | 1/2009 | Rezai et al. |
| 7,483,755 B2 | 1/2009 | Ingle et al. |
| 7,493,160 B2 | 2/2009 | Weber et al. |
| 7,494,661 B2 | 2/2009 | Sanders ...................... 424/239.1 |
| 7,507,234 B2 | 3/2009 | Utley et al. |
| 7,507,238 B2 | 3/2009 | Edwards et al. |
| 7,517,320 B2 | 4/2009 | Wibowo et al. ................ 600/529 |
| 7,530,979 B2 | 5/2009 | Ganz et al. |
| 7,532,938 B2 | 5/2009 | Machado et al. |
| 7,542,802 B2 | 6/2009 | Danek et al. ..................... 607/42 |
| 7,553,307 B2 | 6/2009 | Bleich et al. ....................... 606/1 |
| 7,556,624 B2 | 7/2009 | Laufer et al. .................... 604/514 |
| 7,559,890 B2 | 7/2009 | Wallace et al. |
| 7,572,245 B2 | 8/2009 | Herweck et al. |
| 7,585,296 B2 | 9/2009 | Edwards et al. |
| 7,588,549 B2 | 9/2009 | Eccleston |
| 7,594,925 B2 | 9/2009 | Danek et al. ..................... 607/96 |
| 7,608,275 B2 | 10/2009 | Deem et al. |
| 7,613,515 B2 | 11/2009 | Knudson et al. |
| 7,617,005 B2 | 11/2009 | Demarais et al. |
| 7,620,451 B2 | 11/2009 | Demarais et al. |
| 7,628,789 B2 | 12/2009 | Soltesz et al. .................... 606/41 |
| 7,632,268 B2 | 12/2009 | Edwards et al. |
| 7,641,632 B2 | 1/2010 | Noda et al. |
| 7,641,633 B2 | 1/2010 | Laufer et al. ..................... 604/114 |
| 7,648,500 B2 | 1/2010 | Edwards et al. ................. 606/41 |
| 7,653,438 B2 | 1/2010 | Deem et al. |
| 7,684,865 B2 | 3/2010 | Aldrich et al. ................... 607/40 |
| 7,689,290 B2 | 3/2010 | Ingle et al. |
| 7,691,079 B2 | 4/2010 | Gobel |
| RE41,334 E | 5/2010 | Beatty et al. |
| 7,708,712 B2 | 5/2010 | Phan et al. ......................... 604/8 |
| 7,708,768 B2 | 5/2010 | Danek et al. ..................... 607/96 |
| 7,711,430 B2 | 5/2010 | Errico et al. ..................... 607/42 |
| 7,717,948 B2 | 5/2010 | Demarais et al. |
| 7,722,538 B2 | 5/2010 | Khoury |
| 7,725,188 B2 | 5/2010 | Errico et al. ..................... 607/23 |
| 7,734,355 B2 | 6/2010 | Cohen et al. ................... 607/118 |
| 7,734,535 B1 | 6/2010 | Burns ............................. 705/37 |
| 7,740,017 B2 | 6/2010 | Danek et al. .................. 128/898 |
| 7,740,631 B2 | 6/2010 | Bleich et al. ..................... 606/79 |
| 7,742,795 B2 | 6/2010 | Stone et al. |
| 7,747,324 B2 | 6/2010 | Errico et al. ..................... 607/42 |
| 7,756,583 B2 | 7/2010 | Demarais et al. |
| 7,765,010 B2 | 7/2010 | Chornenky et al. |
| 7,770,584 B2 | 8/2010 | Danek et al. .................. 128/898 |
| 7,783,358 B2 | 8/2010 | Aldrich et al. ................... 607/40 |
| 7,815,590 B2 | 10/2010 | Cooper ............................... 604/8 |
| 7,826,881 B1 | 11/2010 | Beatty et al. |
| 7,831,288 B1 | 11/2010 | Beatty et al. |
| 7,837,676 B2 | 11/2010 | Sinelnikov et al. |
| 7,837,679 B2 | 11/2010 | Biggs et al. ..................... 606/34 |
| 7,841,986 B2 | 11/2010 | He et al. |
| 7,844,338 B2 | 11/2010 | Knudson et al. |
| 7,853,331 B2 | 12/2010 | Kaplan et al. .................... 607/99 |
| 7,854,734 B2 | 12/2010 | Biggs et al. ..................... 606/34 |
| 7,854,740 B2 | 12/2010 | Carney |
| 7,869,879 B2 | 1/2011 | Errico et al. ..................... 607/23 |
| 7,869,880 B2 | 1/2011 | Errico et al. ..................... 607/42 |
| 7,873,417 B2 | 1/2011 | Demarais et al. |
| 7,877,146 B2 | 1/2011 | Rezai et al. |
| 7,904,159 B2 | 3/2011 | Errico et al. ..................... 607/23 |
| 7,906,124 B2 | 3/2011 | Laufer et al. ................. 424/239.1 |
| 7,914,448 B2 | 3/2011 | Bob et al. |
| 7,921,855 B2 | 4/2011 | Danek et al. .................. 128/898 |
| 7,930,012 B2 | 4/2011 | Beatty et al. |
| 7,931,647 B2 | 4/2011 | Wizeman et al. ................ 606/41 |
| 7,937,143 B2 | 5/2011 | Demarais et al. |
| 7,938,123 B2 | 5/2011 | Danek et al. .................. 128/898 |
| 7,949,407 B2 | 5/2011 | Kaplan et al. .................. 607/101 |
| 7,967,782 B2 | 6/2011 | Laufer et al. |
| 7,985,187 B2 | 7/2011 | Wibowo et al. ................ 600/529 |
| 7,992,572 B2 | 8/2011 | Danek et al. .................. 128/898 |
| 7,993,336 B2 | 8/2011 | Jackson et al. |
| 8,002,740 B2 | 8/2011 | Willink et al. ............... 604/96.01 |
| 8,007,495 B2 | 8/2011 | McDaniel et al. |
| 8,010,197 B2 | 8/2011 | Errico et al. ..................... 607/42 |
| 8,012,149 B2 | 9/2011 | Jackson et al. |
| 8,041,428 B2 | 10/2011 | Errico et al. ..................... 607/44 |
| 8,046,085 B2 | 10/2011 | Knudson et al. |
| 8,052,668 B2 | 11/2011 | Sih |
| 8,088,127 B2 | 1/2012 | Mayse et al. |
| 8,099,167 B1 | 1/2012 | Errico et al. ..................... 607/42 |
| 8,105,817 B2 | 1/2012 | Deem et al. |
| 8,128,595 B2 | 3/2012 | Walker et al. |
| 8,128,617 B2 | 3/2012 | Bencini et al. |
| 8,131,371 B2 | 3/2012 | Demarals et al. |
| 8,133,497 B2 | 3/2012 | Deem et al. |
| 8,152,803 B2 | 4/2012 | Edwards et al. |
| 8,172,827 B2 | 5/2012 | Deem et al. |
| 8,204,598 B2 | 6/2012 | Errico et al. |
| 8,208,998 B2 | 6/2012 | Beatty et al. |
| 8,209,034 B2 | 6/2012 | Simon et al. |
| 8,216,216 B2 | 7/2012 | Warnking et al. |
| 8,226,638 B2 | 7/2012 | Mayse et al. |
| 8,229,564 B2 | 7/2012 | Rezai |
| 8,231,621 B2 | 7/2012 | Hutchins et al. |
| 8,233,988 B2 | 7/2012 | Errico et al. |
| 8,251,992 B2 | 8/2012 | Utley et al. |
| 8,267,094 B2 | 9/2012 | Danek et al. |
| 8,295,902 B2 | 10/2012 | Salahieh et al. |
| 8,303,581 B2 | 11/2012 | Arts et al. |
| 8,313,484 B2 | 11/2012 | Edwards et al. |
| 8,328,798 B2 | 12/2012 | Witzel et al. |
| 8,338,164 B2 | 12/2012 | Deem et al. |
| 8,347,891 B2 | 1/2013 | Demarais et al. |
| 8,357,118 B2 | 1/2013 | Orr |
| 8,364,237 B2 | 1/2013 | Stone et al. |
| 8,371,303 B2 | 2/2013 | Schaner et al. |
| 8,377,055 B2 | 2/2013 | Jackson et al. |
| 8,483,831 B1 | 7/2013 | Hlavka et al. |
| 8,489,192 B1 | 7/2013 | Hlavka et al. |
| 8,731,672 B2 | 5/2014 | Hlavka et al. |
| 8,740,895 B2 | 6/2014 | Mayse et al. |
| 8,777,943 B2 | 7/2014 | Mayse et al. |
| 8,808,280 B2 | 8/2014 | Mayse et al. |
| 8,821,489 B2 | 9/2014 | Mayse et al. |
| 2001/0020151 A1 | 9/2001 | Reed et al. |
| 2001/0044596 A1 | 11/2001 | Jaafar ...................... 604/103.01 |
| 2002/0002387 A1 | 1/2002 | Naganuma ....................... 607/1 |
| 2002/0010495 A1 | 1/2002 | Freed et al. ..................... 607/42 |
| 2002/0016344 A1 | 2/2002 | Tracey ........................... 514/343 |
| 2002/0042564 A1 | 4/2002 | Cooper et al. ................ 600/407 |
| 2002/0042565 A1 | 4/2002 | Cooper et al. ................ 600/407 |

(56) References Cited

U.S. PATENT DOCUMENTS

| | | |
|---|---|---|
| 2002/0049370 A1 | 4/2002 | Laufer et al. .................. 600/300 |
| 2002/0072738 A1 | 6/2002 | Edwards et al. ................. 606/41 |
| 2002/0082197 A1 | 6/2002 | Aoki et al. ......................... 514/2 |
| 2002/0087153 A1 | 7/2002 | Roschak et al. ................. 606/27 |
| 2002/0087208 A1 | 7/2002 | Koblish et al. ................. 607/113 |
| 2002/0091379 A1 | 7/2002 | Danek et al. .................... 606/32 |
| 2002/0107512 A1 | 8/2002 | Edwards |
| 2002/0107515 A1 | 8/2002 | Edwards et al. ................. 606/41 |
| 2002/0111386 A1 | 8/2002 | Sekins et al. ................... 514/759 |
| 2002/0111619 A1 | 8/2002 | Keast et al. ...................... 606/41 |
| 2002/0111620 A1 | 8/2002 | Cooper et al. ................... 606/41 |
| 2002/0115991 A1 | 8/2002 | Edwards |
| 2002/0116030 A1 | 8/2002 | Rezai ................................. 607/9 |
| 2002/0143302 A1 | 10/2002 | Hinchliffe et al. ............. 604/272 |
| 2002/0143326 A1 | 10/2002 | Foley et al. |
| 2002/0143373 A1 | 10/2002 | Courtnage et al. .............. 607/91 |
| 2002/0151888 A1 | 10/2002 | Edwards et al. ................. 606/41 |
| 2002/0183682 A1 | 12/2002 | Darvish et al. .................. 604/20 |
| 2002/0198512 A1 | 12/2002 | Seward ............................ 604/522 |
| 2002/0198570 A1 | 12/2002 | Puskas ............................. 607/40 |
| 2002/0198574 A1 | 12/2002 | Gumpert .......................... 607/58 |
| 2003/0018344 A1 | 1/2003 | Kaji et al. ...................... 606/130 |
| 2003/0023287 A1 | 1/2003 | Edwards et al. ............... 607/101 |
| 2003/0027752 A1 | 2/2003 | Steward et al. .................. 514/12 |
| 2003/0050591 A1 | 3/2003 | Patrick McHale ........... 604/4.01 |
| 2003/0050631 A1 | 3/2003 | Mody et al. |
| 2003/0065371 A1 | 4/2003 | Satake |
| 2003/0069570 A1 | 4/2003 | Witzel et al. |
| 2003/0070676 A1 | 4/2003 | Cooper et al. ............. 128/200.24 |
| 2003/0074039 A1 | 4/2003 | Puskas ............................ 607/118 |
| 2003/0093069 A1 | 5/2003 | Panescu et al. |
| 2003/0093128 A1 | 5/2003 | Freed et al. ...................... 607/42 |
| 2003/0125786 A1 | 7/2003 | Gliner et al. |
| 2003/0130657 A1 | 7/2003 | Tom et al. ........................ 606/47 |
| 2003/0144572 A1 | 7/2003 | Oschman et al. ............... 600/16 |
| 2003/0153905 A1 | 8/2003 | Edwards et al. |
| 2003/0159700 A1 | 8/2003 | Laufer et al. .................. 128/898 |
| 2003/0181949 A1 | 9/2003 | Whale ............................... 607/2 |
| 2003/0187430 A1 | 10/2003 | Vorisek |
| 2003/0195593 A1 | 10/2003 | Ingle et al. |
| 2003/0195604 A1 | 10/2003 | Ingle et al. |
| 2003/0202990 A1 | 10/2003 | Donovan et al. ............. 424/239.1 |
| 2003/0208103 A1 | 11/2003 | Sonnenschein et al. |
| 2003/0211121 A1 | 11/2003 | Donovan .................... 424/247.1 |
| 2003/0216791 A1 | 11/2003 | Schuler et al. .................. 607/44 |
| 2003/0216792 A1 | 11/2003 | Levin et al. ..................... 607/48 |
| 2003/0216891 A1 | 11/2003 | Wegener ........................ 702/188 |
| 2003/0225443 A1 | 12/2003 | Kiran et al. |
| 2003/0233099 A1 | 12/2003 | Danaek et al. .................. 606/96 |
| 2003/0236455 A1 | 12/2003 | Swanson et al. |
| 2004/0006268 A1 | 1/2004 | Gilboa et al. |
| 2004/0009180 A1 | 1/2004 | Donovan .................... 424/184.1 |
| 2004/0010289 A1 | 1/2004 | Biggs et al. ....................... 607/2 |
| 2004/0010290 A1 | 1/2004 | Schroeppel et al. .............. 607/3 |
| 2004/0028676 A1 | 2/2004 | Klein et al. ..................... 424/125 |
| 2004/0029849 A1 | 2/2004 | Schatzberg et al. ............ 514/179 |
| 2004/0030368 A1 | 2/2004 | Kemeny et al. ................. 607/88 |
| 2004/0031494 A1 | 2/2004 | Danek et al. |
| 2004/0044390 A1 | 3/2004 | Szeles ............................. 607/142 |
| 2004/0059383 A1 | 3/2004 | Puskas .............................. 607/1 |
| 2004/0073201 A1 | 4/2004 | Cooper et al. ................... 606/14 |
| 2004/0073206 A1 | 4/2004 | Foley et al. |
| 2004/0073278 A1 | 4/2004 | Pachys ............................. 607/88 |
| 2004/0082948 A1 | 4/2004 | Stewart et al. |
| 2004/0086531 A1 | 5/2004 | Barron ......................... 424/239.1 |
| 2004/0087936 A1 | 5/2004 | Stern et al. |
| 2004/0088030 A1 | 5/2004 | Jung, Jr. ......................... 607/109 |
| 2004/0088036 A1 | 5/2004 | Gilbert ............................ 607/148 |
| 2004/0091880 A1 | 5/2004 | Wiebusch et al. .................. 435/6 |
| 2004/0106954 A1 | 6/2004 | Whitehurst et al. .............. 607/3 |
| 2004/0116981 A1 | 6/2004 | Mazar ............................... 607/60 |
| 2004/0122488 A1 | 6/2004 | Mazar et al. ..................... 607/60 |
| 2004/0122489 A1 | 6/2004 | Mazar et al. ..................... 607/60 |
| 2004/0127942 A1 | 7/2004 | Yomtov et al. .................... 607/3 |
| 2004/0127958 A1 | 7/2004 | Mazar et al. ..................... 607/60 |
| 2004/0142005 A1 | 7/2004 | Brooks et al. ............... 424/239.1 |
| 2004/0147921 A1 | 7/2004 | Edwards et al. |
| 2004/0147969 A1 | 7/2004 | Mann et al. ...................... 607/17 |
| 2004/0147988 A1 | 7/2004 | Stephens ........................ 607/108 |
| 2004/0151741 A1 | 8/2004 | Borodic ...................... 424/239.1 |
| 2004/0153056 A1 | 8/2004 | Muller et al. |
| 2004/0162584 A1 | 8/2004 | Hill et al. |
| 2004/0162597 A1 | 8/2004 | Hamilton et al. ............... 607/89 |
| 2004/0167509 A1 | 8/2004 | Taimisto ........................... 606/41 |
| 2004/0167580 A1 | 8/2004 | Mann et al. ..................... 607/17 |
| 2004/0172075 A1 | 9/2004 | Shafer et al. ...................... 607/9 |
| 2004/0172080 A1 | 9/2004 | Stadler et al. .................... 607/17 |
| 2004/0172084 A1 | 9/2004 | Knudson et al. ................ 607/40 |
| 2004/0175399 A1 | 9/2004 | Schiffman .................. 424/239.1 |
| 2004/0176803 A1 | 9/2004 | Whelan et al. .................... 607/2 |
| 2004/0176805 A1 | 9/2004 | Whelan et al. .................... 607/2 |
| 2004/0182399 A1 | 9/2004 | Danek et al. ................... 128/898 |
| 2004/0186435 A1 | 9/2004 | Seward ....................... 604/164.12 |
| 2004/0204747 A1 | 10/2004 | Kemeny et al. ................. 607/94 |
| 2004/0213813 A1 | 10/2004 | Ackerman .................. 424/239.1 |
| 2004/0213814 A1 | 10/2004 | Ackerman .................. 424/239.1 |
| 2004/0215235 A1 | 10/2004 | Jackson et al. |
| 2004/0215289 A1 | 10/2004 | Fukui ............................... 607/48 |
| 2004/0215296 A1 | 10/2004 | Ganz et al. |
| 2004/0220556 A1 | 11/2004 | Cooper et al. ..................... 606/1 |
| 2004/0220621 A1 | 11/2004 | Zhou et al. ........................ 607/2 |
| 2004/0226556 A1 | 11/2004 | Deem et al. |
| 2004/0230251 A1 | 11/2004 | Schuler et al. .................. 607/42 |
| 2004/0230252 A1 | 11/2004 | Kullok et al. .................... 607/48 |
| 2004/0243118 A1 | 12/2004 | Ayers et al. |
| 2004/0243182 A1 | 12/2004 | Cohen et al. ...................... 607/2 |
| 2004/0248188 A1 | 12/2004 | Sanders .......................... 435/7.1 |
| 2004/0249401 A1 | 12/2004 | Rabiner et al. |
| 2004/0249416 A1 | 12/2004 | Yun et al. .......................... 607/2 |
| 2004/0253274 A1 | 12/2004 | Voet ............................ 424/239.1 |
| 2005/0004609 A1 | 1/2005 | Stahmann et al. .............. 607/17 |
| 2005/0004631 A1 | 1/2005 | Benedict ......................... 607/88 |
| 2005/0010263 A1 | 1/2005 | Schauerte ........................ 607/48 |
| 2005/0010270 A1 | 1/2005 | Laufer ............................. 607/88 |
| 2005/0015117 A1 | 1/2005 | Gerber ............................. 607/39 |
| 2005/0019346 A1 | 1/2005 | Boulis ......................... 424/190.1 |
| 2005/0021092 A1 | 1/2005 | Yun et al. .......................... 607/3 |
| 2005/0049615 A1 | 3/2005 | Cooper et al. ................. 606/140 |
| 2005/0055020 A1 | 3/2005 | Skarda |
| 2005/0056292 A1 | 3/2005 | Cooper .......................... 128/898 |
| 2005/0059153 A1 | 3/2005 | George et al. .................. 435/446 |
| 2005/0060041 A1 | 3/2005 | Phan et al. ..................... 623/23.7 |
| 2005/0060042 A1 | 3/2005 | Phan et al. ..................... 623/23.7 |
| 2005/0060044 A1 | 3/2005 | Roschak et al. ............. 623/23.65 |
| 2005/0065553 A1 | 3/2005 | Ben Ezra et al. .................. 607/2 |
| 2005/0065562 A1 | 3/2005 | Rezai ................................. 607/9 |
| 2005/0065567 A1 | 3/2005 | Lee et al. ......................... 607/17 |
| 2005/0065573 A1 | 3/2005 | Rezai ................................ 607/42 |
| 2005/0065574 A1 | 3/2005 | Rezai ................................ 607/45 |
| 2005/0065575 A1 | 3/2005 | Dobak ............................. 607/45 |
| 2005/0065584 A1 | 3/2005 | Schiff et al. |
| 2005/0074461 A1 | 4/2005 | Donovan .................... 424/184.1 |
| 2005/0076909 A1 | 4/2005 | Stahmann et al. ........ 128/204.23 |
| 2005/0080461 A1 | 4/2005 | Stahmann et al. .............. 607/17 |
| 2005/0085801 A1 | 4/2005 | Cooper et al. ................... 606/14 |
| 2005/0090722 A1 | 4/2005 | Perez ............................. 600/315 |
| 2005/0096529 A1 | 5/2005 | Cooper et al. ................. 600/407 |
| 2005/0096644 A1 | 5/2005 | Hall et al. |
| 2005/0107783 A1 | 5/2005 | Tom et al. ........................ 606/47 |
| 2005/0107829 A1 | 5/2005 | Edwards et al. .................. 607/2 |
| 2005/0107853 A1 | 5/2005 | Krespi et al. .................... 607/89 |
| 2005/0125044 A1 | 6/2005 | Tracey ............................. 607/45 |
| 2005/0137518 A1 | 6/2005 | Biggs et al. ....................... 604/8 |
| 2005/0137611 A1 | 6/2005 | Escudero et al. .............. 606/108 |
| 2005/0137715 A1 | 6/2005 | Phan et al. ................... 623/23.65 |
| 2005/0143788 A1 | 6/2005 | Yun et al. ......................... 607/46 |
| 2005/0149146 A1 | 7/2005 | Boveja et al. ................... 607/58 |
| 2005/0152924 A1 | 7/2005 | Voet ............................ 424/239.1 |
| 2005/0153885 A1 | 7/2005 | Yun et al. ......................... 514/12 |
| 2005/0159736 A9 | 7/2005 | Danek et al. .................... 606/32 |
| 2005/0165456 A1 | 7/2005 | Mann et al. ..................... 607/30 |
| 2005/0171396 A1 | 8/2005 | Pankratov et al. |
| 2005/0177144 A1 | 8/2005 | Phan et al. ...................... 606/14 |
| 2005/0177192 A1 | 8/2005 | Rezai et al. ....................... 607/3 |

(56) References Cited

U.S. PATENT DOCUMENTS

| | | |
|---|---|---|
| 2005/0182288 A1 | 8/2005 | Zabara .................... 600/14 |
| 2005/0182393 A1 | 8/2005 | Abboud et al. |
| 2005/0183732 A1 | 8/2005 | Edwards ............... 128/898 |
| 2005/0187579 A1 | 8/2005 | Danek et al. ............. 607/1 |
| 2005/0193279 A1 | 9/2005 | Daners |
| 2005/0203503 A1 | 9/2005 | Edwards et al. |
| 2005/0222628 A1 | 10/2005 | Krakousky ................ 607/3 |
| 2005/0222635 A1 | 10/2005 | Krakovsky ............... 607/39 |
| 2005/0222651 A1 | 10/2005 | Jung ...................... 607/104 |
| 2005/0228054 A1 | 10/2005 | Tatton .................... 514/656 |
| 2005/0228459 A1 | 10/2005 | Levin et al. .............. 607/40 |
| 2005/0228460 A1 | 10/2005 | Levin et al. .............. 607/40 |
| 2005/0234523 A1 | 10/2005 | Levin et al. .............. 607/42 |
| 2005/0238693 A1 | 10/2005 | Whyte .................... 424/439 |
| 2005/0240176 A1 | 10/2005 | Oral et al. |
| 2005/0240241 A1 | 10/2005 | Yun et al. ................. 607/42 |
| 2005/0245992 A1 | 11/2005 | Persen et al. ............ 607/60 |
| 2005/0251128 A1 | 11/2005 | Amoah |
| 2005/0251213 A1 | 11/2005 | Freeman .................. 607/5 |
| 2005/0255317 A1 | 11/2005 | Bavaro et al. |
| 2005/0256028 A1 | 11/2005 | Yun et al. ................. 514/2 |
| 2005/0261747 A1 | 11/2005 | Schuler et al. ........... 607/42 |
| 2005/0267536 A1 | 12/2005 | Freeman et al. ......... 607/5 |
| 2005/0277993 A1 | 12/2005 | Mower ..................... 607/9 |
| 2005/0283197 A1 | 12/2005 | Daum et al. ............. 607/17 |
| 2006/0015151 A1 | 1/2006 | Aldrich ................... 607/40 |
| 2006/0058692 A1 | 3/2006 | Beatty et al. |
| 2006/0058693 A1 | 3/2006 | Beatty et al. |
| 2006/0058780 A1 | 3/2006 | Edwards et al. ......... 606/40 |
| 2006/0062808 A1 | 3/2006 | Laufer et al. ............ 424/239.1 |
| 2006/0079887 A1 | 4/2006 | Buysse et al. |
| 2006/0084884 A1 | 4/2006 | Beatty et al. |
| 2006/0084966 A1 | 4/2006 | Maguire et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0089637 A1 | 4/2006 | Werneth et al. |
| 2006/0095032 A1 | 5/2006 | Jackson et al. |
| 2006/0100666 A1 | 5/2006 | Wilkinson et al. ...... 607/1 |
| 2006/0106361 A1 | 5/2006 | Muni et al. .............. 604/500 |
| 2006/0111755 A1 | 5/2006 | Stone et al. .............. 607/42 |
| 2006/0116749 A1 | 6/2006 | Willink et al. ........... 623/1.11 |
| 2006/0135953 A1 | 6/2006 | Kania et al. |
| 2006/0135984 A1 | 6/2006 | Kramer et al. .......... 606/192 |
| 2006/0135998 A1 | 6/2006 | Libbus et al. ............ 607/2 |
| 2006/0137698 A1 | 6/2006 | Danek et al. ............. 128/898 |
| 2006/0142801 A1 | 6/2006 | Demarais et al. ....... 607/2 |
| 2006/0167498 A1 | 7/2006 | DiLorenzo ............... 607/2 |
| 2006/0178703 A1 | 8/2006 | Huston et al. ........... 607/2 |
| 2006/0206150 A1 | 9/2006 | Demarais et al. ....... 607/3 |
| 2006/0212076 A1 | 9/2006 | Demarais et al. ....... 607/2 |
| 2006/0212078 A1 | 9/2006 | Demarais et al. ....... 607/3 |
| 2006/0222667 A1 | 10/2006 | Deem et al. .............. 424/239.1 |
| 2006/0225742 A1 | 10/2006 | Deem et al. |
| 2006/0235474 A1 | 10/2006 | Demarais ................. 607/2 |
| 2006/0241523 A1 | 10/2006 | Sinelnikov et al. |
| 2006/0247617 A1 | 11/2006 | Danek et al. ............ 606/41 |
| 2006/0247618 A1 | 11/2006 | Kaplan et al. ........... 606/41 |
| 2006/0247619 A1 | 11/2006 | Kaplan et al. ........... 606/41 |
| 2006/0247683 A1 | 11/2006 | Danek et al. ............. 607/2 |
| 2006/0247726 A1 | 11/2006 | Biggs et al. .............. 607/42 |
| 2006/0247727 A1 | 11/2006 | Biggs et al. .............. 607/42 |
| 2006/0247746 A1 | 11/2006 | Danek et al. ............. 607/115 |
| 2006/0254600 A1 | 11/2006 | Danek et al. ............. 128/898 |
| 2006/0259028 A1 | 11/2006 | Utley et al. .............. 606/41 |
| 2006/0259029 A1 | 11/2006 | Utley et al. .............. 606/41 |
| 2006/0259030 A1 | 11/2006 | Utley et al. .............. 606/41 |
| 2006/0265014 A1 | 11/2006 | Demarais et al. ....... 607/2 |
| 2006/0265015 A1 | 11/2006 | Demarais et al. ....... 607/2 |
| 2006/0271111 A1 | 11/2006 | Demarais et al. ....... 607/2 |
| 2006/0276807 A1 | 12/2006 | Keast et al. .............. 606/140 |
| 2006/0276852 A1 | 12/2006 | Demarais et al. ....... 607/44 |
| 2006/0278243 A1 | 12/2006 | Danek et al. ............. 128/898 |
| 2006/0278244 A1 | 12/2006 | Danek et al. ............. 128/898 |
| 2006/0280772 A1 | 12/2006 | Roschak et al. ......... 424/426 |
| 2006/0280773 A1 | 12/2006 | Roschak et al. ......... 424/426 |
| 2006/0282071 A1 | 12/2006 | Utley et al. |
| 2006/0287679 A1 | 12/2006 | Stone ...................... 607/2 |
| 2007/0021803 A1 | 1/2007 | Deem et al. .............. 607/46 |
| 2007/0025919 A1 | 2/2007 | Deem et al. |
| 2007/0027496 A1 | 2/2007 | Parnis et al. ............. 607/42 |
| 2007/0032788 A1 | 2/2007 | Edwards et al. |
| 2007/0043342 A1 | 2/2007 | Kleinberger |
| 2007/0055328 A1 | 3/2007 | Mayse et al. |
| 2007/0060954 A1 | 3/2007 | Cameron et al. ........ 607/2 |
| 2007/0060990 A1 | 3/2007 | Satake .................... 607/101 |
| 2007/0062545 A1 | 3/2007 | Danek et al. ............. 128/898 |
| 2007/0066957 A1 | 3/2007 | Demarais et al. ....... 604/500 |
| 2007/0074719 A1 | 4/2007 | Danek et al. ............. 128/200.24 |
| 2007/0083194 A1 | 4/2007 | Kunis et al. |
| 2007/0083197 A1 | 4/2007 | Danek et al. ............. 606/47 |
| 2007/0083239 A1 | 4/2007 | Demarais et al. |
| 2007/0093802 A1 | 4/2007 | Danek et al. ............. 606/41 |
| 2007/0093809 A1 | 4/2007 | Edwards et al. ........ 606/41 |
| 2007/0100390 A1 | 5/2007 | Danaek et al. ........... 607/42 |
| 2007/0102011 A1 | 5/2007 | Danek et al. ............. 128/898 |
| 2007/0106292 A1 | 5/2007 | Kaplan et al. ........... 606/41 |
| 2007/0106296 A1 | 5/2007 | Laufer et al. ............ 606/50 |
| 2007/0106337 A1 | 5/2007 | Errico et al. ............. 607/40 |
| 2007/0106338 A1 | 5/2007 | Errico ..................... 607/42 |
| 2007/0106339 A1 | 5/2007 | Errico et al. ............. 607/42 |
| 2007/0106348 A1 | 5/2007 | Laufer ..................... 607/88 |
| 2007/0112349 A1 | 5/2007 | Danek et al. ............. 606/45 |
| 2007/0118184 A1 | 5/2007 | Danek et al. ............. 607/42 |
| 2007/0118190 A1 | 5/2007 | Danek et al. ............. 607/96 |
| 2007/0123922 A1 | 5/2007 | Cooper et al. ........... 606/191 |
| 2007/0123958 A1 | 5/2007 | Laufer ..................... 607/93 |
| 2007/0123961 A1 | 5/2007 | Danek et al. ............. 607/101 |
| 2007/0129720 A1 | 6/2007 | Demarais et al. ....... 606/41 |
| 2007/0129760 A1 | 6/2007 | Demarais et al. ....... 607/2 |
| 2007/0129761 A1 | 6/2007 | Demarais et al. ....... 607/3 |
| 2007/0135875 A1 | 6/2007 | Demarais et al. ....... 607/96 |
| 2007/0173899 A1 | 7/2007 | Levin et al. .............. 607/40 |
| 2007/0191902 A1 | 8/2007 | Errico et al. ............. 607/42 |
| 2007/0197896 A1 | 8/2007 | Moll et al. ............... 600/407 |
| 2007/0203549 A1 | 8/2007 | Demarais et al. ....... 607/72 |
| 2007/0225768 A1 | 9/2007 | Dobak, III ............... 607/2 |
| 2007/0232896 A1 | 10/2007 | Gilboa et al. |
| 2007/0239256 A1 | 10/2007 | Weber et al. |
| 2007/0244479 A1 | 10/2007 | Beatty et al. |
| 2007/0250050 A1 | 10/2007 | Lafontaine |
| 2007/0255270 A1 | 11/2007 | Carney |
| 2007/0255304 A1 | 11/2007 | Roschak et al. ......... 606/185 |
| 2007/0265639 A1 | 11/2007 | Danek et al. ............. 606/130 |
| 2007/0265687 A1 | 11/2007 | Deem et al. .............. 607/72 |
| 2007/0267011 A1 | 11/2007 | Deem et al. .............. 128/200.23 |
| 2008/0004596 A1 | 1/2008 | Yun et al. |
| 2008/0021274 A1 | 1/2008 | Bayer et al. |
| 2008/0021369 A1 | 1/2008 | Deem et al. .............. 604/20 |
| 2008/0051839 A1 | 2/2008 | Libbus et al. ............ 607/2 |
| 2008/0086107 A1 | 4/2008 | Roschak ................... 604/506 |
| 2008/0097422 A1 | 4/2008 | Edwards et al. |
| 2008/0097424 A1 | 4/2008 | Wizeman et al. ....... 606/41 |
| 2008/0125772 A1 | 5/2008 | Stone et al. |
| 2008/0147137 A1 | 6/2008 | Cohen et al. ............. 607/17 |
| 2008/0154258 A1 | 6/2008 | Chang et al. |
| 2008/0161801 A1 | 7/2008 | Steinke et al. |
| 2008/0183248 A1 | 7/2008 | Rezai et al. .............. 607/62 |
| 2008/0188912 A1 | 8/2008 | Stone et al. |
| 2008/0188913 A1 | 8/2008 | Stone et al. |
| 2008/0194956 A1 | 8/2008 | Aldrich et al. ........... 600/439 |
| 2008/0208305 A1 | 8/2008 | Rezai et al. |
| 2008/0213331 A1 | 9/2008 | Gelfand et al. .......... 424/422 |
| 2008/0234564 A1 | 9/2008 | Beatty et al. |
| 2008/0243112 A1 | 10/2008 | De Neve .................. 606/28 |
| 2008/0255449 A1 | 10/2008 | Warnking et al. |
| 2008/0255642 A1 | 10/2008 | Zarins et al. ............. 607/99 |
| 2008/0262489 A1 | 10/2008 | Steinke ..................... 606/33 |
| 2008/0275445 A1 | 11/2008 | Kelly et al. |
| 2008/0302359 A1 | 12/2008 | Loomas et al. .......... 128/200.24 |
| 2008/0306570 A1 | 12/2008 | Rezai et al. .............. 607/42 |
| 2008/0312543 A1 | 12/2008 | Laufer et al. ............ 600/486 |
| 2008/0312725 A1 | 12/2008 | Penner ..................... 607/119 |
| 2008/0319350 A1 | 12/2008 | Wallace et al. |

(56) References Cited

U.S. PATENT DOCUMENTS

| | | | |
|---|---|---|---|
| 2009/0018473 A1 | 1/2009 | Aldrich et al. ............... 601/2 |
| 2009/0018538 A1 | 1/2009 | Webster et al. ............ 606/41 |
| 2009/0030477 A1 | 1/2009 | Jarrard ....................... 607/42 |
| 2009/0036948 A1 | 2/2009 | Levin et al. ................. 607/44 |
| 2009/0043301 A1* | 2/2009 | Jarrard et al. .............. 606/41 |
| 2009/0043302 A1 | 2/2009 | Ford et al. .................. 606/41 |
| 2009/0048593 A1 | 2/2009 | Ganz et al. |
| 2009/0060953 A1 | 3/2009 | Sandars ................. 424/239.1 |
| 2009/0062873 A1 | 3/2009 | Wu et al. ....................... 607/2 |
| 2009/0069797 A1 | 3/2009 | Danek et al. ............... 606/33 |
| 2009/0076409 A1 | 3/2009 | Wu et al. .................... 600/547 |
| 2009/0076491 A1 | 3/2009 | Roschak et al. ............ 606/21 |
| 2009/0112203 A1 | 4/2009 | Danek et al. ............... 606/33 |
| 2009/0124883 A1 | 5/2009 | Wibowo et al. ............ 600/407 |
| 2009/0131765 A1 | 5/2009 | Roschak et al. ............ 600/301 |
| 2009/0131928 A1 | 5/2009 | Edwards et al. ............ 606/33 |
| 2009/0131930 A1 | 5/2009 | Gelbart et al. |
| 2009/0143678 A1 | 6/2009 | Keast et al. ................ 600/439 |
| 2009/0143705 A1 | 6/2009 | Danek et al. ................. 601/3 |
| 2009/0143776 A1 | 6/2009 | Danek et al. ............... 606/21 |
| 2009/0143831 A1 | 6/2009 | Huston et al. ................ 607/2 |
| 2009/0155336 A1 | 6/2009 | Rezai ....................... 424/423 |
| 2009/0177192 A1 | 7/2009 | Rioux et al. |
| 2009/0192505 A1 | 7/2009 | Askew et al. |
| 2009/0192508 A1 | 7/2009 | Laufer et al. ............... 606/41 |
| 2009/0204005 A1 | 8/2009 | Keast et al. ................ 600/461 |
| 2009/0204119 A1 | 8/2009 | Bleich et al. ............... 606/79 |
| 2009/0227885 A1 | 9/2009 | Lowery et al. |
| 2009/0227980 A1 | 9/2009 | Kangas et al. |
| 2009/0232850 A1 | 9/2009 | Manack et al. ........... 424/239.1 |
| 2009/0248011 A1 | 10/2009 | Hlavka et al. .............. 606/41 |
| 2009/0254079 A1 | 10/2009 | Edwards et al. |
| 2009/0254142 A1 | 10/2009 | Edwards et al. |
| 2009/0259274 A1 | 10/2009 | Simon et al. ............... 607/40 |
| 2009/0275840 A1 | 11/2009 | Roschak et al. ............ 600/467 |
| 2009/0275878 A1 | 11/2009 | Cambier et al. ............ 604/21 |
| 2009/0281593 A9 | 11/2009 | Errico et al. ................ 607/42 |
| 2009/0287087 A1 | 11/2009 | Gwerder et al. ............ 600/463 |
| 2009/0306644 A1 | 12/2009 | Mayse et al. |
| 2009/0318904 A9 | 12/2009 | Cooper et al. ................ 606/1 |
| 2009/0319002 A1 | 12/2009 | Simon ......................... 607/45 |
| 2010/0003282 A1 | 1/2010 | Deem et al. ............... 424/238.1 |
| 2010/0004648 A1 | 1/2010 | Edwards et al. |
| 2010/0010564 A1 | 1/2010 | Simon ......................... 607/45 |
| 2010/0016709 A1 | 1/2010 | Gilboa et al. |
| 2010/0042089 A1 | 2/2010 | Soltesz et al. |
| 2010/0049031 A1 | 2/2010 | Fruland et al. |
| 2010/0049186 A1 | 2/2010 | Ingle et al. |
| 2010/0049188 A1 | 2/2010 | Nelson et al. |
| 2010/0057178 A1 | 3/2010 | Simon ......................... 607/117 |
| 2010/0063495 A1 | 3/2010 | Edwards et al. |
| 2010/0070004 A1 | 3/2010 | Hlavka et al. .............. 607/62 |
| 2010/0076518 A1 | 3/2010 | Hlavka et al. .............. 607/42 |
| 2010/0087783 A1 | 4/2010 | Weber et al. |
| 2010/0087809 A1 | 4/2010 | Edwards et al. |
| 2010/0094231 A1 | 4/2010 | Bleich et al. ............... 604/274 |
| 2010/0114087 A1 | 5/2010 | Edwards et al. |
| 2010/0116279 A9 | 5/2010 | Cooper ....................... 128/898 |
| 2010/0125239 A1 | 5/2010 | Perry et al. |
| 2010/0130892 A1 | 5/2010 | Warnking |
| 2010/0137860 A1 | 6/2010 | Demarais et al. ........... 606/41 |
| 2010/0145427 A1 | 6/2010 | Gliner et al. |
| 2010/0152835 A1 | 6/2010 | Orr |
| 2010/0160906 A1 | 6/2010 | Jarrard ....................... 606/33 |
| 2010/0160996 A1 | 6/2010 | Simon et al. ............... 607/44 |
| 2010/0174340 A1 | 7/2010 | Simon ......................... 607/40 |
| 2010/0179424 A1 | 7/2010 | Warnking et al. |
| 2010/0185190 A1 | 7/2010 | Danek et al. ............... 606/29 |
| 2010/0191089 A1 | 7/2010 | Stebler et al. |
| 2010/0204689 A1 | 8/2010 | Danek et al. ............... 606/27 |
| 2010/0222851 A1 | 9/2010 | Deem et al. |
| 2010/0228318 A1 | 9/2010 | Errico et al. ................ 607/42 |
| 2010/0241188 A1 | 9/2010 | Errico et al. ................ 607/42 |
| 2010/0249873 A1 | 9/2010 | Errico ......................... 607/40 |
| 2010/0256629 A1 | 10/2010 | Wylie et al. |
| 2010/0256630 A1 | 10/2010 | Hamilton, Jr. et al. |
| 2010/0268222 A1 | 10/2010 | Danek et al. ............... 606/41 |
| 2010/0298905 A1 | 11/2010 | Simon ......................... 607/40 |
| 2010/0305463 A1 | 12/2010 | Macklem et al. ............ 600/529 |
| 2010/0318020 A1 | 12/2010 | Atanasoska et al. |
| 2010/0331776 A1 | 12/2010 | Salahieh et al. |
| 2011/0004148 A1 | 1/2011 | Ishii |
| 2011/0015548 A1 | 1/2011 | Aldrich et al. ............... 601/2 |
| 2011/0028898 A1 | 2/2011 | Clark, III et al. |
| 2011/0046432 A1 | 2/2011 | Simon et al. ............... 600/14 |
| 2011/0060380 A1 | 3/2011 | Gelfand et al. ............. 607/42 |
| 2011/0079230 A1 | 4/2011 | Danek et al. ............... 128/898 |
| 2011/0093032 A1 | 4/2011 | Boggs, II et al. ........... 607/42 |
| 2011/0098762 A1 | 4/2011 | Rezai |
| 2011/0112400 A1 | 5/2011 | Emery et al. ............... 600/439 |
| 2011/0112521 A1 | 5/2011 | Delonzor et al. |
| 2011/0118725 A1 | 5/2011 | Mayse et al. |
| 2011/0125203 A1 | 5/2011 | Simon et al. ................. 607/2 |
| 2011/0125213 A1 | 5/2011 | Simon et al. ............... 607/42 |
| 2011/0130708 A1 | 6/2011 | Perry et al. |
| 2011/0137284 A1 | 6/2011 | Arora et al. |
| 2011/0144630 A1 | 6/2011 | Loeb |
| 2011/0146673 A1 | 6/2011 | Keast et al. ............... 128/200.24 |
| 2011/0146674 A1 | 6/2011 | Roschak ................... 128/200.24 |
| 2011/0152855 A1 | 6/2011 | Mayse et al. |
| 2011/0152967 A1 | 6/2011 | Simon et al. ............... 607/45 |
| 2011/0152974 A1 | 6/2011 | Rezai et al. |
| 2011/0166499 A1 | 7/2011 | Demarais et al. |
| 2011/0166565 A1 | 7/2011 | Wizeman et al. ........... 606/33 |
| 2011/0172655 A1 | 7/2011 | Biggs et al. ................. 606/34 |
| 2011/0172658 A1 | 7/2011 | Gelbart et al. |
| 2011/0178569 A1 | 7/2011 | Parnis et al. |
| 2011/0184330 A1 | 7/2011 | Laufer et al. ................. 604/8 |
| 2011/0190569 A1 | 8/2011 | Simon et al. ............... 600/26 |
| 2011/0196288 A1 | 8/2011 | Kaplan et al. ............... 604/28 |
| 2011/0202098 A1 | 8/2011 | Demarais et al. |
| 2011/0224768 A1 | 9/2011 | Edwards |
| 2011/0230701 A1 | 9/2011 | Simon et al. ................. 600/9 |
| 2011/0230938 A1 | 9/2011 | Simon et al. ............... 607/63 |
| 2011/0245756 A1 | 10/2011 | Arora et al. |
| 2011/0251592 A1 | 10/2011 | Biggs et al. ................. 604/514 |
| 2011/0257622 A1 | 10/2011 | Salahieh et al. |
| 2011/0257647 A1 | 10/2011 | Mayse et al. |
| 2011/0263960 A1 | 10/2011 | Mitchell |
| 2011/0264086 A1 | 10/2011 | Ingle |
| 2011/0270249 A1 | 11/2011 | Utley et al. |
| 2011/0276107 A1 | 11/2011 | Simon et al. ............... 607/46 |
| 2011/0276112 A1 | 11/2011 | Simon et al. ............... 607/72 |
| 2011/0282229 A1 | 11/2011 | Danek et al. ............... 600/538 |
| 2011/0282418 A1 | 11/2011 | Saunders et al. |
| 2011/0301587 A1 | 12/2011 | Deem et al. |
| 2011/0301664 A1 | 12/2011 | Rezai ......................... 607/42 |
| 2011/0301679 A1 | 12/2011 | Rezai et al. |
| 2011/0306851 A1 | 12/2011 | Wang |
| 2011/0306904 A1 | 12/2011 | Jacobson et al. |
| 2011/0306997 A9 | 12/2011 | Roschak et al. ............ 606/185 |
| 2011/0319958 A1 | 12/2011 | Simon et al. ............... 607/42 |
| 2012/0004656 A1 | 1/2012 | Jackson et al. |
| 2012/0015019 A1 | 1/2012 | Pacetti et al. |
| 2012/0016256 A1 | 1/2012 | Mabary et al. |
| 2012/0016358 A1 | 1/2012 | Mayse et al. |
| 2012/0016363 A1 | 1/2012 | Mayse et al. |
| 2012/0016364 A1 | 1/2012 | Mayse et al. |
| 2012/0029261 A1 | 2/2012 | Deem et al. |
| 2012/0029500 A1 | 2/2012 | Jenson |
| 2012/0029512 A1 | 2/2012 | Willard et al. |
| 2012/0029591 A1 | 2/2012 | Simon et al. ............... 607/42 |
| 2012/0029601 A1 | 2/2012 | Simon et al. ............... 607/72 |
| 2012/0041412 A1 | 2/2012 | Roth et al. |
| 2012/0041509 A1 | 2/2012 | Knudson et al. |
| 2012/0071870 A1 | 3/2012 | Salahieh et al. |
| 2012/0078096 A1 | 3/2012 | Krolik et al. |
| 2012/0083734 A1 | 4/2012 | Ayres et al. |
| 2012/0089078 A1 | 4/2012 | Deem et al. |
| 2012/0089138 A1 | 4/2012 | Edwards et al. |
| 2012/0101326 A1 | 4/2012 | Simon et al. |
| 2012/0101413 A1 | 4/2012 | Beetel et al. |
| 2012/0109278 A1 | 5/2012 | Sih |
| 2012/0143132 A1 | 6/2012 | Orlowski |

(56) References Cited

U.S. PATENT DOCUMENTS

| | | |
|---|---|---|
| 2012/0143177 A1 | 6/2012 | Avitall |
| 2012/0143179 A1 | 6/2012 | Avitall |
| 2012/0143181 A1 | 6/2012 | Demarais et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0158101 A1 | 6/2012 | Stone et al. |
| 2012/0165803 A1 | 6/2012 | Bencini et al. |
| 2012/0184801 A1 | 7/2012 | Simon et al. |
| 2012/0185020 A1 | 7/2012 | Simon et al. |
| 2012/0191081 A1 | 7/2012 | Markowitz |
| 2012/0191082 A1 | 7/2012 | Markowitz |
| 2012/0197100 A1 | 8/2012 | Razavi et al. |
| 2012/0197246 A1 | 8/2012 | Mauch |
| 2012/0197251 A1 | 8/2012 | Edwards et al. |
| 2012/0203067 A1 | 8/2012 | Higgins et al. |
| 2012/0203216 A1 | 8/2012 | Mayse et al. |
| 2012/0203222 A1 | 8/2012 | Mayse et al. |
| 2012/0209118 A1 | 8/2012 | Warnking |
| 2012/0209259 A1 | 8/2012 | Danek et al. |
| 2012/0209261 A1 | 8/2012 | Mayse et al. |
| 2012/0209296 A1 | 8/2012 | Mayse et al. |
| 2012/0221087 A1 | 8/2012 | Parnis et al. |
| 2012/0232436 A1 | 9/2012 | Warnking |
| 2012/0245415 A1 | 9/2012 | Emura et al. |
| 2012/0253442 A1 | 10/2012 | Gliner et al. |
| 2012/0259263 A1 | 10/2012 | Celermajer et al. |
| 2012/0259269 A1 | 10/2012 | Meyer |
| 2012/0259326 A1 | 10/2012 | Brannan et al. |
| 2012/0265280 A1 | 10/2012 | Errico et al. |
| 2012/0289952 A1 | 11/2012 | Utley et al. |
| 2012/0290035 A1 | 11/2012 | Levine et al. |
| 2012/0294424 A1 | 11/2012 | Chin et al. |
| 2012/0296329 A1 | 11/2012 | Ng |
| 2012/0302909 A1 | 11/2012 | Mayse et al. |
| 2012/0310233 A1 | 12/2012 | Dimmer et al. |
| 2012/0316552 A1 | 12/2012 | Mayse et al. |
| 2012/0316559 A1 | 12/2012 | Mayse et al. |
| 2012/0330298 A1 | 12/2012 | Ganz et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0035576 A1 | 2/2013 | O'Grady et al. |
| 2013/0123751 A1 | 5/2013 | Deem et al. |
| 2013/0289555 A1 | 10/2013 | Mayse et al. |
| 2013/0289556 A1 | 10/2013 | Mayse et al. |
| 2013/0296647 A1 | 11/2013 | Mayse et al. |
| 2013/0303948 A1 | 11/2013 | Deem et al. |
| 2013/0310822 A1 | 11/2013 | Mayse et al. |
| 2013/0345700 A1 | 12/2013 | Hlavka et al. |
| 2014/0186341 A1 | 7/2014 | Mayse |
| 2014/0236148 A1 | 8/2014 | Hlavka et al. |
| 2014/0257271 A1 | 9/2014 | Mayse et al. |
| 2014/0276792 A1 | 9/2014 | Kaveckis et al. |

FOREIGN PATENT DOCUMENTS

| | | |
|---|---|---|
| CN | 101115448 B | 5/2010 |
| DE | 19952505 A1 | 5/2001 |
| EP | 189329 A3 | 6/1987 |
| EP | 286145 A2 | 10/1988 |
| EP | 280225 A3 | 3/1989 |
| EP | 286145 A3 | 10/1990 |
| EP | 282225 B1 | 6/1992 |
| EP | 0 643 982 | 3/1995 |
| EP | 908713 A1 | 4/1999 |
| EP | 1 143 864 | 10/2001 |
| EP | 1 271 384 | 1/2003 |
| EP | 1 281 366 | 2/2003 |
| EP | 908150 B1 | 5/2003 |
| EP | 1 326 549 | 7/2003 |
| EP | 768091 B1 | 7/2003 |
| EP | 1326548 | 7/2003 |
| EP | 1 400 204 | 3/2004 |
| EP | 1297795 B1 | 8/2005 |
| EP | 1 588 662 | 10/2005 |
| FR | 2659240 B1 | 7/1997 |
| GB | 2233293 A | 1/1991 |
| RU | 2053814 | 2/1996 |
| SU | 545358 T | 2/1977 |
| WO | 89/11311 | 11/1989 |
| WO | 93/01862 | 2/1993 |
| WO | 93/16632 | 9/1993 |
| WO | 94/07446 | 4/1994 |
| WO | 95/01075 | 1/1995 |
| WO | 9502370 A2 | 1/1995 |
| WO | 9510322 A1 | 4/1995 |
| WO | 9604860 A1 | 2/1996 |
| WO | 9610961 A1 | 4/1996 |
| WO | 97/25917 | 7/1997 |
| WO | 9732532 A1 | 9/1997 |
| WO | 9733715 A1 | 9/1997 |
| WO | 9737715 A1 | 10/1997 |
| WO | 9740751 A1 | 11/1997 |
| WO | 98/18391 | 5/1998 |
| WO | 9844854 A1 | 10/1998 |
| WO | 9852480 A1 | 11/1998 |
| WO | 9856234 A1 | 12/1998 |
| WO | 9856324 A1 | 12/1998 |
| WO | 9903413 A1 | 1/1999 |
| WO | 9858681 A3 | 3/1999 |
| WO | 9913779 A2 | 3/1999 |
| WO | 9932040 A1 | 7/1999 |
| WO | 99/42047 | 8/1999 |
| WO | 9964109 A1 | 12/1999 |
| WO | 00/10598 | 3/2000 |
| WO | 0051510 A1 | 9/2000 |
| WO | 00/62699 | 10/2000 |
| WO | 00/66017 | 11/2000 |
| WO | 01/00114 | 1/2001 |
| WO | 0103642 A1 | 1/2001 |
| WO | 01/70114 | 9/2001 |
| WO | 01/89526 | 11/2001 |
| WO | 0205720 A1 | 1/2002 |
| WO | 0205868 A2 | 1/2002 |
| WO | 0232333 A1 | 4/2002 |
| WO | 0232334 A1 | 4/2002 |
| WO | 03/073358 | 9/2003 |
| WO | 03/088820 | 10/2003 |
| WO | 2004/078252 | 9/2004 |
| WO | 2004/082736 | 9/2004 |
| WO | 2004/101028 | 11/2004 |
| WO | 2005/006963 | 1/2005 |
| WO | 2005/006964 | 1/2005 |
| WO | 2006/053308 | 5/2006 |
| WO | 2006/053309 | 5/2006 |
| WO | 2006/116198 | 11/2006 |
| WO | WO 2007/001981 A2 | 1/2007 |
| WO | 2007/058780 A9 | 5/2007 |
| WO | 2007/061982 | 5/2007 |
| WO | 2007/092062 A1 | 8/2007 |
| WO | 2007/094828 A3 | 8/2007 |
| WO | 2007/143665 | 12/2007 |
| WO | 2008/005953 | 1/2008 |
| WO | 2008/024220 | 2/2008 |
| WO | 2008/051706 | 5/2008 |
| WO | 2008/063935 | 5/2008 |
| WO | 2009/009236 | 1/2009 |
| WO | 2009/015278 | 1/2009 |
| WO | 2009082433 A2 | 7/2009 |
| WO | 2009/126383 A3 | 10/2009 |
| WO | 2009137819 A1 | 11/2009 |
| WO | 2010/110785 A1 | 9/2010 |
| WO | 2011060200 A1 | 5/2011 |
| WO | WO 2011/060200 A1 | 5/2011 |

OTHER PUBLICATIONS

Ahnert-Hilger et al., "Introduction of Macromolecules into Bovine Adrenal-Medullary Chromaffin Cells and Rat Pheochromocytoma Cells (PC12) by Permeabilization with Streptolysin O: Inhibitory

(56) References Cited

OTHER PUBLICATIONS

Effect of Tetanus Toxin on Catecholamine Secretion," *J. Neurochem* 52(6):1751-1758, Jun. 1989.

Barlaw, "Surgical Treatment of Asthma," *Postgrad Med. Journal* 25:193-196, 1949.

Bester et al., "Recovery of C-Fiber-Induced Extravasation Following Peripheral Nerve Injury in the Rat," *Experimental Neurology* 154:628-636, 1998.

Bigalke et al., "Clostridial Neurotoxins," *Handbook of Experimental Pharmacology* (Aktories, K., and Just, I., eds) 145:407-443, 2000.

Bittner et al., "Isolated Light Chains of Botulinum Neurotoxins Inhibit Exocytosis," *The Journal of Biological Chemistry* 264(18):10354-10360, 1989.

Blindt et al., "Development of a New Biodegradable Intravascular Polymer Stent with Simultaneous Incorporation of Bioactive Substances," *The International Journal of Artificial Organs* 22(12):843-853, 1999.

Bradley et al., "Effect of vagotomy on the breathing pattern and exercise ability in emphysematous patients," *Clinical Science* 62:311-319, 1982.

Breekveldt-Postma et al., "Enhanced persistence with tiotropium compared with other respiratory drugs in COPD," *Respiratory Medicine* 101:1398-1405, 2007.

Brody et al., "Mucociliary clearance after lung denervation and bronchial transection," *J. Applied Physiology* 32(2):160-164, 1972.

Buzzi, "Diphtheria Toxin Treatment of Human Advanced Cancer," *Cancer Research* 42:2054-2058, 1982.

Canning et al., "Reflex Mechanisms in Gastroesophageal Reflux Disease and Asthma," *The American Journal of Medicine* 115(3A):45S-48S, 2003.

Canning et al., "Reflex Mechanisms in Gastroesophageal Reflux Disease and Asthma," *Am J Med.* 115(Suppl 3A):45S-48S, 2003. (Abstract only.).

Canning, "Reflex regulation of airway smooth muscle tone," *J Appl. Physiol.* (101):971-985, 2006.

Chaddock et al. "Expression and Purification of Catalytically Active, Non-Toxic Endopeptidase Derivatives of *Clostridium botulinum* Toxin Type A," *Protein Expression and Purification* 25(2):219-228, Jul. 2002.
Chang, "Cell poration and cell fusion using an oscillating electric field," *Biophys. J.* 56:641-652, 1989.
Chernyshova et al., "The Effect of Low-Energy Laser Radiation in the Infrared Spectrum on Bronchial Patency in Children With Bronchial Asthma," *Vopr Kurortol, Fizioter Lech Fiz Kult* 2:11-14, 1995.
Crimi et al., "Protective effects of inhaled ipratropium bromide on bronchoconstriction induced by adenosine and methacholine in asthma," *Eur Respir J* 5:560-565, 1992.
Dimitrov-Szokodi et al., "Lung Denervation in the Therapy of Intractable Bronchial Asthma," *J. Thoracic Surg.* 33(2):166-184, Feb. 1957.
Donohue et al., "A 6-Month, Placebo-Controlled Study Comparing Lung Function and Health Status Changes in COPD Patients Treated With Tiotropium or Salmeterol," *Chest* 122:47-55, 2002.
De Paiva et al., "Light chain of botulinum neurotoxin is active in mammalian motor nerve terminals when delivered via liposomes," *FEBS Lett.* 17:277(1-2): 171-174, Dec. 1990.
Feshenko et al., "Clinico-morphological comparisons in the laser therapy of chronic bronchitis patients," *Lik Sprava.* (10-12):75-79, 1993. (+ English abstract, 1 Page).
Friedman et al., "Healthcare Costs with Tiotropium Plus Usual Care versus Usual Care Alone Following 1 Year of Treatment in Patients with Chronic Obstructive Pulmonary Disorder (COPD),"*Pharmacoeconomics* 22(10:741-749, 2004.
Gelb et al., "Laser in treatment of lung cancer," *Chest* 86(5):662-666, 1984.
George et al., "Factors Associated With Medication Nonadherence in Patients With COPD," *Chest* 128:3198-3204, 2005.
Gerasin et al., "Endobronchial electrosurgery," *Chest* 93:270-274, 1988.
Gibson et al., "Gastroesophageal Reflux Treatment for Asthma in Adults and Children," *Cochrane Database Syst. Rev.* 2:CD001496, 2003. (Abstract only.).
Glanville et al., "Bronchial responsiveness after human heart-lung transplantation," *Chest* 97(6):1360-1366, 1990.
Glanville et al., "Bronchial responsiveness to exercise after human cardiopulmonary transplantation," *Chest* 96(2):81-286, 1989.
Gosens et al., "Muscarinic receptor signaling in the pathophysiology of asthma and COPD," *Respiratory Research* 7(73):1-15, 2006.
Groeben et al. "High Thoracic Epidural Anesthesia Does Not Alter Airway Resistance and Attenuates the Response to an Inhalational Provocation Test in Patients with Bronchial Hyperreactivity," *Anesthesiology* 81(4):868-874, 1994.
Guarini et al., "Efferent Vagal Fibre Stimulation Blunts Nuclear Factor-kB Activation and Protects Against Hypovolemic Hemmorrhagic Shock," *Circulation* 107:1189-1194, 2003.
Guzmán et al., "Bioeffects Caused by Changes in Acoustic Cavitation Bubble Density and Cell Concentration: A Unified Explanation Based on Cell-to-Bubble Ratio and Blast Radius," *Ultrasound in Med. & Biol.* 29(8):1211-1222, 2003.
Hainsworth et al., "Afferent lung denervation by brief inhalation of steam," *Journal of Applied Physiology* (34)5: 708-714, 1972.
Harding, "Recent Clinical Investigations Examining the Association of Asthma and Gastroesophageal Reflux," *Am J Med.* 115(Suppl 3A):39S-44S, 2003. (Abstract only.).
Hiraga, "Experimental surgical therapy of bronchial asthma. The effect of denervation in dogs," *Nihon Kyobu Shikkan Gakkai Zasshi* 19(1):46-56, 1981.
Hoffmann et al., "Inhibition of Histamine-Induced Bronchoconstriction in Guinea Pig and Swine by Pulsed Electrical Vagus Nerve Stimulation," *Neuromodulation: Technology at the Neural Interface*:1-9, 2009.
Hooper et al., "Endobronchial electrocautery," *Chest* 87(6):12-714, 1985.
Ivanyuta OM, et al., "Effect of Low-Power Laser Irradiation of Bronchia Mucosa on the State of Systemic and Local Immunity in Patients with Chronic Bronchitis," *Problemy Tuberkuleza* 6:26-29, 1991.
Jammes et al., "Assessment of the Pulmonary Origin of Bronchoconstrictor Vagal Tone," *J. Physiol.* 291: 305-316, 1979.
Jiang et al., "Effects of Antireflux Treatment on Bronchial Hyper-responsiveness and Lung Function in Asthmatic Patients with Gastroesophageal Reflux Disease," *World J Gastroenterol.* 9:1123-1125, 2003. (Abstract only.).
Khmel'kova et al., "Does laser irridation affect bronchial obstruction?," *Probl Tuberk* 3:41-42, 1995. (Abstract only.).
Khoshoo et al., "Role of Gastroesophageal Reflux in Older Children with Persistent Asthma," *Chest* 123:1008-1013, 2003. (Abstract only.).
Kiljander, "The Role of Proton Pump Inhibitors in the Management of Gastroesophageal Reflux Disease-Related Asthma and Chronic Cough," *Am J Med.* 115(Suppl 3A):65S-71S, 2003. (Abstract only.).
Kistner et al., "Reductive Cleavage of Tetanus Toxin and Botulinum Neurotoxin A by the Thioredoxin System from Brain," *Naunyn-Schmiedebergs Arch Pharmacol* 345(2):227-234, Feb. 1992.
Kliachkin et al., "Bronchoscopy in the treatment of bronchial asthma of infectious allergic origin," *Ter Arkh* 54(4):76-79, 1982.
Korochkin et al., "Use of a Helium-Neon Laser in Combined Treatment of Bronchial Asthma," *New Developments in Diagnostics and Treatment*, 1990, 9 pgs.
Korpela et al., "Comparison of Tissue Reactions in the Tracheal Mucosa Surrounding a Bioabsorbable and Silicone Airway Stents," *Annals of Thoracic Surgery* 66:1772-1776, 1998.
Kreitman, "Taming ricin toxin," *Nature Biotechnology* 21:372-374, 2003.
Kuntz, "The Autonomic Nervous System in Relation to the Thoracic Viscera," *Chest* 10:1-18, 1944.
Lennerz et al., "Electrophysiological characterization of vagal afferents relevant to mucosal nociception in the rat upper oesophagus," *J. Physiol.* 582(1):229-242, 2007.
Levin, "The Treatment of Bronchial Asthma by Dorsal Sympathectomy," *Annals of Surgery* 102(2):161-170, 1935.

(56) References Cited

OTHER PUBLICATIONS

Liou et al., "Causative and Contributive Factors to Asthmas Severity and Patterns of Medication Use in Patients Seeking Specialized Asthma Care," Chest 124:1781-1788, 2003. (Abstract only.).
Løkke et al., "Developing COPD: a 25 year follow up study of the general population," Thorax 61:935-939, 2006.
Maesen et al., "Tiotropium bromide, a new long-acting antimuscarinic bronchodilator: a pharmacodynamic study in patients with chronic obstructive pulmonary disease (COPD)," Eur. Respi. J. 8:1506-1513, 1995.
Magnussen et al., "Effect of Inhaled Ipratropium Bromide on the Airway Response to Methacholine, Histamine, and Exercise in Patients with Mild Bronchial Asthma," Respiration 59:42-47, 1992.
Maltais et al, "Improvements in Symptom-Limited Exercise Performance Over 8 h With Once-Daily Tiotropium in Patients With COPD," Chest 128:1168-1178, 2005.
Mathew et al., "Gastro-oesophageal reflux and bronchial asthma: current status and future directions," Postgrad Med. J. 80:701-705, 2004.
McKay et al., "Autocrine regulation of asthmatic airway inflammation: role of airway smooth muscle," Respir Res 3(11):1-13, 2002.
Mehta et al., "Effect of endobronchial radiation therapy on malignant bronchial obstruction," Chest 97(3):662-665, 1990.
Meshalkin et al., "Partial denervation of the pulmonary hilus as one of the methods of surgical treatment of bronchial asthma," Grudn Khir 1:109-111, 1975.
Moore, Keith L., Clinically Oriented Anatomy, $2^{nd}$ ed., Williams & Wilkins, Baltimore, 1985, pp. 85 and 87. (Abstract only.).
Netter, Frank H., The Ciba Collection of Medical Illustrations: vol. 7, Respiratory System, CIBA-GEIGY Corporation, West Caldwell, 1979, p. 23, section 1. (Abstract only.).
Ochs, Matthias et al., Fisherman, Alfred P., et al. (eds), Functional Design of the Human Lung for Gas Exchange, $4^{th}$ ed., McGraw Hill Medical, New York, 2008, Chap. 2, "Fisherman's Pulmonary Diseases and Disorders." (Abstract only.).
O'Connor et al., "Prolonged Effect of Tiotropium Bromide on Methacholine-induced Bronchoconstriction in Asthma," Am. J. Respir. Crit. Care Med. 154:876-880, 1996.
Ovcharenko et al., "Endobronchial use of low-frequency ultrasound and ultraviolet laser radiation in the complex treatment of patients with suppurative bronchial diseases," Probl Tuberk 3:40-42, 1997. (Abstract only.).
Overholt, "Glomectomy for Asthma," Dis Chest 40:605-610, 1961.
Peters et al., "Tiotropium Bromide Step-Up Therapy for Adults with Uncontrolled Asthma," New England Journal of Medicine 363(18):1715-1726, Oct. 28, 2010.
Petrou, et al., "Bronchoscopic Diathermy Resection and Stent Insertion: a Cost Effective Treatment for Tracheobronchial Obstruction," Thorax 48:1156-1159, 1993.
Provotorov VM, et al., "Clinical Efficacy of Treatment of Patients with Non-Specific Pulmonary Diseases by Using Low-Power Laser Irradiation and Performing Intrapulmonary Drug Administration," Terapevichesky Arkhiv 62:18-23, 1991.
Raj, "Editorial," Pain Practice 4(1S):S1-S3, 2004.
Ramirez et al., "Sympathetomy in Bronchial Asthma," J. A. M A. 84 (26):2002-2003, 1925.
Rienhoff et al., "Treatment of Intractable Bronchial Asthma by Bilateral Resection of the Posterior Pulmonary Plexus," Arch Surg 37(3):456-469, 1938.
Savchenko et al., "Adaptation of regulatory physiological systems in surgical treatment of patients with bronchial asthma," Klin Med (Mosk) 74(7):38-39, 1996.
Sengupta, "Part 1 Oral cavity, pharynx and esophagus—Esophageal sensory physiology," GI Motility online:17 pages, 2006.
Sepulveda et al., "Treatment of Asthmatic Bronchoconstriction by Percutaneous Low Voltage Vagal Nerve Stimulation: Case Report," Internet Journal of Asthma, Allergy, and Immunology 7(2):3 pages, 2009.
Shaari et al., "Rhinorrhea is Decreased in Dogs After Nasal Application of Botulinum Toxin," Otolaryngol Head Neck Surg 112(14):566-571, 1992.
Sheski FD, et al., "Cryotherapy, Electrocautery, and Brachytherapy," Clinics in Chest Medicine 20(1):123-138, Mar. 1999.
Sil'vestrov et al., "The Clinico-Pathogenetic Validation and Efficacy of the Use of Low-Energy Laser Irradiation and Glucocorticoids in the Treatment of Bronchial Asthma Patients," Ter Arkh 63(11), 87-92, 1991.
Simonsson et al., "Role of Autonomic Nervous System and the Cough Reflex in the Increased Responsiveness of Airways in Patients with Obstructive Airway Disease," The Journal of Clinical Investigation 46(11): 1812-1818, 1967.
Simpson et al., "Isolation and Characterization of the Botulinum Neurotoxins," Methods Enzymol 165:76-85, 1988.
Smakov, "Denervation of the lung in the treatment of bronchial asthma," Khirurgiia (Mosk) 9:117-120, 1982.
Smakov, "Pathogenetic substantiation of lung denervation in bronchial asthma and it's indications," Khirurgiia (Mosk) 2:67-69, 1999.
Sontag et al., "Asthmatics with Gastroesophageal Reflux: Long-term Results of a Randomized Trial of Medical and Surgical Antireflux Therapies," Am J Gastroenterol. 98:987-999, 2003. (Abstract only.).
Stein, "Possible Mechanisms of Influence of Esophageal Acid on Airway Hyperresponsiveness," Am J Med. 115(Suppl 3A):55S-59S, 2003. (Abstract only.).
Sundaram et al., "An Experimental and Theoretical Analysis of Ultrasound-Induced Permeabilization of Cell Membranes," Biophysical Journal 84:3087-3101, 2003.
Takino et al., "Surgical Removal of the Carotid Body and its Relation to the Carotid Chemoreceptor and Baroreceptor Reflex in Asthmatics," Dis Chest 47:129-138, 1965.
Tashkin et al., "Long-term Treatment Benefits With Tiotropium in COPD Patients With and Without Short-term Bronchodilator Responses," Chest 123: 1441-1449, 2003.
Tsugeno et al., "A Proton-Pump Inhibitor, Rabeprazole, Improves Ventilatory Function in Patients with Asthma Associated with Gastroesophageal Reflux," Scand J Gastroenterol. 38:456-461, 2003. (Abstract only.).
Tsuji et al., "Biodegradable Stents as a Platform to Drug Loading," International Journal of Cardiovascular Interventions 5:13-16, 2003.
Unal et al., "Effect of Botulinum Toxin Type A on Nasal Symptoms in Patients with Allergic Rhinitis: A Double-blind, Placebo-controlled Clinical Trial," Acta Oto-Laryngologica 123(9):1060-0163, Dec. 2003.
Van Boxem Um, et al., "Tissue Effects of Bronchoscopic Electrocautery," Chest 117(3):887-891, Mar. 1999.
van der Velden et al., "Autonomic Innervation of Human Airways: Structure, Function, and Pathophysiology in Asthma," Neuroimmunomodulation 6:145-159, 1999.
Verhein et al., "Neural Control of Airway Inflammation," Current Allergy and Asthma Reports 9:484-490, 2009.
Vincken et al., "Improved health outcomes in patients with COPD during 1 yr's treatment with tiotropium," Eur. Respir. J. 19: 209-216, 2002.
Vorotnev et al., "Treatment of Patients with Chronic Obstructive Bronchitis Using Low Energy Laser at a General Rehabilitation Center," Therapeutic Archive 3:17-19, 1997. (+English translation, 4 pages.).
Wagner et al., "Methacholine causes reflex bronchoconstriction," J. Appl. Physiol. 86:294-297, 1999.
Wahidi et al., "State of the Art: Interventional Pulmonology," Chest 131:261-274, 2007.
Weaver, "Electroporation: A General Phenomenon for Manipulating Cells and Tissues," Journal of Cellular Biochemistry 51(4):426-435, Apr. 1993.
Wirtz et al., "Bilateral Lung Transplantation for Severe Persistent and Difficult Asthma," The Journal of Heart and Lung Transplantation 24(10):1700-1703, 2005.
Laufer, "Method and Apparatus for Treating Smooth Muscles in the Walls of Body Conduits," U.S. Appl. No. 09/095,323, filed Jun. 10, 1998, 25 pages.

(56) References Cited

OTHER PUBLICATIONS

Global Strategy for Asthma Management and Prevention, 2002, 192 Pages Total.
James, et al., "The Mechanics of Airway Narrowing in Asthma," Am. Rev. Respir. Dis., 1989, 139, 242-246.
Janssen L. J., "Asthma therapy: how far have we come, why did we fail and where should we go next?," Eur Respir J, 2009, 33, pp. 11-20.
Kitamura S., "Color Atlas of Clinical Application of Fiberoptic Bronchoscopy," 1990, Year Book Medical Publishers, 17.
Kraft M., "The distal airways: are they Important in asthma?," European Respiratory, 1999, 1403-1417.
Notice of final Rejection, Japanese Patent Application No. 2000-553172, dated Sep. 2, 2008, 5 pages.
PCT International search report for application No. PCT/US00/05412 mailed on Jun. 20, 2000, 2 pages.
PCT International search report for application No. PCT/US00/18197 mailed on Oct. 3, 2000, 1 page.
PCT International search report for application No. PCT/US00/28745 mailed on Mar. 28, 2001, 6 pages.
PCT International search report for application No. PCT/US01/32321 mailed on Jan. 18, 2002, 2 pages.
PCT International search report for application No. PCT/US98/03759 mailed on Jul. 30, 1998, 1 page.
PCT International search report for application No. PCT/US98/26227 mailed on Mar. 25, 1999, 1 page.
PCT International search report for application No. PCT/US99/00232 mailed on Mar. 4, 1999, 1 page.
PCT International search report for application No. PCT/US99/12986 mailed on Sep. 29, 1999, 1 page.
Peter K. Jeffery, "Remodeling in Asthma and Chronic Obstructive Lung Disease," American Journal of Respiratory and Critical Care Medicine, 2001, 164 (10), 13516.
Seow C. Y., et al. "Signal Transduction in Smooth Muscle Historical perspective on airway smooth muscle: the saga of a frustrated cell," J Appl Physiol, 2001, 91, 938-952.
Stephanie A.Shore, "Airway Smooth Muscle in Asthma—Not Just More of the Same." N Engl J Med, 2004, 351 (6), 531-532.
UNSW Embryo-Respiratory System [online] Embryology, 2007, [retrieved on Dec. 10, 2007]. Retrieved from the internet: (URL: http://embryology.med.unsw.edu.au/Refer/respire/select.htm).
Wayne Mitzner, "Airway Smooth Muscle the appendix of the Lung," American Journal of Respiratory and Critical Care Medicine, 2004, 169, 787-790.
Wayne Mitzner, "Bronchial Thermoplasty in Asthma," Allergology International, 2006, 55, 225-234.
Non-Final Office Action for U.S. Appl. No. 11/398,353; Mailed on Aug. 31, 2009; 7 pages.
Non-Final Office Action for U.S. Appl. No. 11/398,353; Mailed on Apr. 27, 2010; 8 pages.
Co-pending U.S. Appl. No. 09/244,173.
Co-pending U.S. Appl. No. 09/095,323.
Simon R. Johnson et al., Synthetic Functions of Airway Smooth Muscle in Asthma, Trends Pharmacol. Sci., Aug. 1997, 18(8), 288-292.
Macklem P.T., Mechanical Factors Determining Maximum Bronchoconstriction, European Respiratory Journal, Jun. 1989, 6, 516s-519s.
James C. Hogg, The Pathology of Asthma, APMIS, Oct. 1997, 105(10), 735-745.
Dierkesmann et al., Indication and Results of Endobronchial Laser Therapy, Lung, 1990, 168, 1095-1102.
Netter F.H., Respiratory System: A Compilation of Paintings Depicting Anatomy and Embryology, Physiology, Pathology, Pathophysiology, and Clinical Features and Treatment of Diseases, In the CIBA Collection of Medical Illustrations M.B. Divertie, ed., Summit New Jersey, 1979, vol. 7, 119-135.
Provotorov et al.; The Clinical Efficacy of Treating Patients with Nonspecific Lung Disease by Using Low-energy Laser Irradiation and Intrapulmonary Drug Administration, ISSN: 0040-3660., Terapevticheskii Arkhiv (USSR), 1991, 63 (12), 18-23.

Wiggs B.R. et al., On the Mechanism of Mucosal Folding in Normal and Asthmatic Airways, J. Appl. Physiol., Dec. 1997, 83(6), 1814-1821.
An, S. S. et al., Airway smooth muscle dynamics; a common pathway of airway obstruction in asthma, European Respiratory Journal, 2007, vol. 29, No. 5, pp. 834-860.
Bel, E, H., Hot Stuff: Bronchial Thermoplasty for Asthma, American Journal of Respiratory and Critical Care Medicine, 2006, vol. 173, pp. 941-942.
Brown, R. H. et al., In vivo evaluation of the effectiveness of bronchial thermoplasty with computed tomography. Journal of Applied Physiology, 2005, vol. 98, pp. 1603-1606.
Brown, R. H. et al., Effect of bronchial thermoplasty on airway distensibility, European Respiratory Journal, vol. 26, No. 2, pp. 277-282.
Chhajed, P., Will There be a Role for Bronchoscopic Radiofrequency Ablation?, 2005, J Bronchol, vol. 12, No. 3, p. 184.
Cox, G., et al, . Early Clinical Experience With Bronchial Thermoplasty for the Treatment of Asthma, 2002, p. 1068.
Cox, G. et al., Asthma Control During the Year After Bronchial Thermoplasty, The New England Journal of Medicine, Mar. 29, 2007, vol. 356, No. 13, pp. 1327-1337.
Cox. G. et al., Bronchial Thermoplasty: One-Year Update, American Thoracic Society Annual Meeting, 2004, p. 1.
Cox, G., et al., Development of a Novel Bronchoscope Therapy for Asthma, Journal of Allergy and Clinical Immunology, 2003, p. 1.
Cox, G., et al., Bronchial Thermoplasty for Asthma, American Journal of Respiratory and Critical Care Medicine, 2006, vol. 173, pp. 965-969.
Cox, G., et al., Bronchial Thermoplasty: Long-Term Follow-up and Patient Satisfaction, 2004, p. 1.
Cox, G., et al., Radiofrequency ablation of airway smooth muscle for sustained treatment of asthma: preliminary investigations, European Respiratory Journal, 2004, 24, pp. 659-663.
Cox, G., et al., Clinical Experience with Bronchial Thermoplasty for the Treatment of Asthma, 2003, Chest 124, p. 106S.
Cox, G., et al., Impact of bronchial thermoplasty on asthma status: interim results from the AIR trial, 2006, European Respiratory Society Annual. Meeting, Munich, Germany, p. 1.
Danek, C. J., et al., Bronchial thermoplasty reduces canine airway responsiveness to local methacholine challenge, 2002, American Thoracic Society Annual Meeting, p. 1.
Danek, C. J., et al., Asthma Intervention Research (AIR) Trial Evaluating Bronchial Thermoplasty™; Early Results, 2002, American Thoracic Society Annual Meeting, p. 1.
Danek, C. J., et al., Reduction in airway hyperesponsiveness to methacholine by the application of RF energy in dogs, J Appl Physiol, 2004, vol. 97, pp. 1946-1933.
Solway, J. et al., Airway Smooth Muscle as a Target for Asthma Therapy, The New England Journal of Medicine, Mar. 29, 2007, 356(13), pp. 1367-1369.
Lavioletts, et al. Asthma Intervention Research (AIR) Trial: Early Safety Assessment of Bronchial Thermoplasty, 2004, p. 1.
Leff et al., Bronchial Thermoplasty Alters Airway Smooth Muscle and Reduces Responsiveness in Dogs; A Possible Procedure for the Treatment of Asthma, American Thoracic Society Annual Meeting, 2002, p. 1.
Lim, E.E. et al., Botulinum Toxin: A Novel Therapeutic Option for Bronchial Asthma?, Medical Hypotheses, 2006, vol. 66, pp. 915-919.
Lombard, et al, Histologic Effects of Bronchial Thermoplasty of Canine and Human Airways, American Thoracic Society Annual Meeting, 2002, p. 1.
Mayse, M. et al., Clinical Pearls for Bronchial Thermoplasty, J Bronchol, Apr. 2007, vol. 14, No. 2, pp. 115-123.
Miller. J. D. et al., A Prospective Feasibility Study of Bronchial Thermoplasty in the Human Airway. 2005. vol. 127, No. 6 pp. 1999-2006.
Miller, J. D. et al., Bronchial Thermoplasty is Well Tolerated by Non-Asthmatic Patients Requiring Lobectomy, 2002, American Thoracic Society Annual Meeting, p. 1.

(56) References Cited

OTHER PUBLICATIONS

Rubin, et al., Bronchial Thermoplasty improves Asthma Status of Moderate to Severe Persistent Asthmatics Over and Above Current Standard-of-Care, 2006, American College of Chest Physicians, 2 pages.
Sterk, P. J., Heterogeneity of Airway Hyperresponsiveness: Time for Unconventional, but Traditional Studies, 2004, The American Pshychoiogical Society, pp. 2017-2018.
Wilson, S. R. et al., Global assessment after bronchial thermoplasty: the patient's perspective, Journal of Outcomes Research, 2006, vol. 10, pp. 37-46.
Toma, T. P., Brave New World for Interventional Bronchoscopy, 2005, Thorax, vol. 60, pp. 180-181.
Trow, T., Clinical Year in Review I, proceedings of the American Thoracic Society, 2006, vol. 3, pp. 553-556.
Wizeman, et al., A Computer Model of Thermal Treatment of Airways by Radiofrequency (RF) Energy Delivery, 2007, American Thoracic Society Annual Meeting, p. 1.
Vasilotta, P. I. et al., "I-R Laser: A New Therapy in Rhino-Sino-Nasal Bronchial Syndrome with Asthmatic Component," American Society for Laser medicine and Surgery abstracts, date unknown, p. 74.
Shesterina. M. V. et al., Effect of laser therapy on immunity in patients with bronchial asthma and pulmonary tuberculosis, 1993, pp. 23-26.
Evis Exera Bronchovideoscope Brochure, Olympus BF-XT160, Olympus, Jun. 15, 2007, 2 pages.
Accad, M., "Single-Step Renal Denervation With the OneShot™ Ablation System," presentation at the Leipzig Interventional Course 2012 in Leipzig, Germany, Jan. 26, 2012, 11 pages.
Bertog, S., "Covidien-Maya: OneShot™," presentation at the 2012 Congenital & Structural Interventions Congress in Frankfurt, Germany, Jun. 28, 2012, 25 pages.
Rocha-Singh, K.J., "Renal Artery Denervation: A Brave New Frontier," *Endovascular Today*, Feb. 2012, pp. 45-53.
Wilson, K.C., et al., "Flexible Bronchoscopy: Indications and Contraindications," UpToDate, Nov. 12, 2010 <www.uptodate.com> [retrieved Sep. 30, 2012], 15 pages.
Laude, G.S., "Pulmonary Manifestations of Gastroesophageal Reflux Disease," *Annals of Thoracic Medicine* 4(3):115-123, Jul.-Sep. 2009.
Awadh, N., et al. "Airway Wall Thickness in Patients With Near Fatal Asthma and Control Groups: Assessment With High Resolution Computed Tomographic Scanning," *Thorax* 53:248-253, 1998.
Castro, M., et al., "Effectiveness and Safety of Bronchial Thermoplasty in the Treatment of Severe Asthma: A Multicenter, Randomized, Double-Blind, Sham-Controlled Clinical Trial," *American Journal of Respiratory and Critical Care Medicine* 181: 116-124, 2010.
Martin, N., et al., "Bronchial Thermoplasty for the Treatment of Asthma," *Current Allergy and Asthma Reports* 9(1):88-95, Jan. 2009.
McEvoy, C.E., et al., "Changing the Landscape: Bronchial Thermoplasty Offers a Novel Approach to Asthma Treatment," *Advance for Managers of Respiratory Care*, pp. 22, 24-25, Oct. 2007.
Michaud, G., et al., "Positioned for Success: Interest in Diagnostic and Therapeutic Bronchoscopy is Growing," *Advance for Managers of Respiratory Care*, pp. 40, 42-43, Jul./Aug. 2008.
O'Sullivan, M.P., et al., "Apoptosis in the Airways: Another Balancing Act in the Epithelial Program," *American Journal of Respiratory Cell and Molecular Biology* 29:3-7, 2003.
Pavord, I.D., et al., "Safety and Efficacy of Bronchial Thermoplasty in Symptomatic, Severe Asthma," *American Journal of Respiratory and Critical Care Medicine* 176:1185-1191, 2007.
Tschumperlin, D.J., et al., "Chronic Effects of Mechanical Force on Airways," *Annual Review of Physiology* 68: 563-83, 2006.
Tschumperlin, D.J., et al., "Mechanical Stimuli to Airway Remodeling," *American Journal of Respiratory and Critical Care Medicine* 164:S90-S94, 2001.
Wechsler, M.E., "Bronchial Thermoplasty for Asthma: A Critical Review of a New Therapy," *Allergy and Asthma Proceedings* 29(4):1-6, Jul.-Aug. 2008.
Co-Pending U.S. Appl. No. 13/523,223, filed Jun. 14, 2012, Edwin J. Hlavka et al.
Preliminary Amendment and Response to Restriction Requirement filed Oct. 22, 2012, in co-pending U.S. Appl. No. 13/523,223, filed Jun. 14, 2012, Edwin J. Hlavka et al.
Co-Pending U.S. Appl. No. 12/372,607, filed Feb. 17, 2009, Edwin J. Hlavka et al.
Amendment After Allowance filed Sep. 17, 2012, in co-pending U.S. Appl. No. 12/372,607, filed Feb. 17, 2009, Edwin J. Hlavka et al.
Montaudon, M., et al., "Assessment of bronchial wall thickness and lumen diameter in human adults using multi-detector computed tomography: comparison with theoretical models," *J. Anat.* 211:579-588, 2007.
Urologix, Inc., "CTC Advance™ Instructions for Use," Targis® System Manual, 2010, 8 pages.
Urologix, Inc., "Cooled ThermoTherapy™," 2012, retrieved on Mar. 3, 2005 from URL=http://www.urologix.com/cllinicians/cooled-thermotherapy.php, 2 pages.
Application and File History of U.S. Appl. No. 12/463,304; Inventor: Martin L. Mayse, et al.; filed May 8, 2009; Issued as U.S. Pat. No. 8,088,127 on Jan. 3, 2012; Systems, Assemblies, and Methods for Treating a Bronchial Tree.
Application and File History of U.S. Appl. No. 13/245,522; Inventor: Martin L. Mayse, et al.; filed Sep. 26, 2011; Issued as U.S. Pat. No. 8,226,638 on Jul. 24, 2012; Systems, Assemblies, and Methods for Treating a Bronchial Tree.
Application and File History of U.S. Appl. No. 13/452,660; Inventor: Martin L. Mayse, et al.; filed Apr. 20, 2012; Issued as U.S. Pat. No. 8,821,489 on Sep. 2, 2014; Systems, Assemblies, and Methods for Treating a Bronchial Tree.
Application and File History of U.S. Appl. No. 13/452,664; Inventor: Martin L. Mayse, et al.; filed Apr. 20, 2012; Issued as U.S. Pat. No. 8,808,280 on Aug. 19, 2014; Systems, Assemblies, and Methods for Treating a Bronchial Tree.
Application and File History of U.S. Appl. No. 13/592,075; Inventor: Martin L. Mayse, et al.; filed Aug. 22, 2012; Systems, Assemblies, and Methods for Treating a Bronchial Tree.
Application and File History of U.S. Appl. No. 13/452,648; Inventor: Martin L. Mayse, et al.; filed Apr. 20, 2012; Systems, Assemblies, and Methods for Treating a Bronchial Tree.
Application and File History of U.S. Appl. No. 13/452,655; Inventor: Martin L. Mayse, et al.; filed Apr. 20, 2012; Systems, Assemblies, and Methods for Treating a Bronchial Tree.
Application and File History of U.S. Appl. No. 12/913,702; Inventor: Martin L. Mayse, et al.; filed Oct. 27, 2010; Delivery Devices With Coolable Energy Emitting Assemblies.
Application and File History of U.S. Appl. No. 13/245,529; Inventor: Martin L. Mayse, et al.; filed Sep. 26, 2011; Delivery Devices With Coolable Energy Emitting Assemblies.
Application and File History of U.S. Appl. No. 13/245,537; Inventor: Martin L. Mayse, et al.; filed Sep. 26, 2011; Delivery Devices With Coolable Energy Emitting Assemblies.
Application and File History of U.S. Appl. No. 13/931,208; Inventor: Martin L. Mayse, et al.; filed Jun. 28, 2013; Issued as U.S. Pat. No. 8,777,943 on Jul. 15, 2014; Delivery Devices With Coolable Energy Emitting Assemblies.
Application and File History of U.S. Appl. No. 13/930,825; Inventor: Martin L. Mayse, et al.; filed Jun. 28, 2013; Issued as U.S. Pat. No. 8,740,895on Jun. 3, 2014; Delivery Devices With Coolable Energy Emitting Assemblies.
Application and File History of U.S. Appl. No. 13/931,246; Inventor: Martin L. Mayse, et al.; filed Jun. 28, 2013; Delivery Devices With Coolable Energy Emitting Assemblies.
English Translation of Office Action from related Japanese application JP 2012-538992, dated Jul. 13, 2014, 2 pgs.
EP Communication dated Jan. 29, 2015 for EP Application No. 14188819.8 filed Nov. 11, 2010, 7 pages.
Office Action dated Mar. 24, 2015 for Japanese Application No. 2012-538992 filed Nov. 11, 2010, 5 pages.
Office Action dated May 14, 2015 for Chinese Application No. 201080060627.6 filed Nov. 11, 2010, 7 pages.

* cited by examiner

SYSTEMS, APPARATUSES, AND METHODS FOR TREATING TISSUE AND CONTROLLING STENOSIS

CROSS-REFERENCE TO RELATED APPLICATION

This application claims the benefit under 35 U.S.C. §119(e) of U.S. Provisional Patent Application No. 61/260,349 filed Nov. 11, 2009. This provisional application is incorporated herein by reference in its entirety.

BACKGROUND

1. Technical Field

The present invention generally relates to systems, apparatuses, and methods for treating tissue, and more particularly, the invention relates to systems, apparatuses, and methods for eliciting a desired response while controlling stenosis.

2. Description of the Related Art

Pulmonary diseases may cause a wide range of problems that adversely affect performance of the lungs. Pulmonary diseases, such as asthma and chronic obstructive pulmonary disease ("COPD"), may lead to increased airflow resistance in the lungs. Mortality, health-related costs, and the size of the population having adverse effects due to pulmonary diseases are all substantial. These diseases often adversely affect quality of life. Symptoms are varied but often include cough; breathlessness; and wheeze. In COPD, for example, breathlessness may be noticed when performing somewhat strenuous activities, such as running, jogging, brisk walking, etc. As the disease progresses, breathlessness may be noticed when performing non-strenuous activities, such as walking. Over time, symptoms of COPD may occur with less and less effort until they are present all of the time, thereby severely limiting a person's ability to accomplish normal tasks.

Pulmonary diseases are often characterized by airway obstruction associated with blockage of an airway lumen, thickening of an airway wall, alteration of structures within or around the airway wall, or combinations thereof. Airway obstruction can significantly decrease the amount of gas exchanged in the lungs resulting in breathlessness. Blockage of an airway lumen can be caused by excessive intraluminal mucus or edema fluid, or both. Thickening of the airway wall may be attributable to excessive contraction of the airway smooth muscle, airway smooth muscle hypertrophy, mucous glands hypertrophy, inflammation, edema, or combinations thereof. Alteration of structures around the airway, such as destruction of the lung tissue itself, can lead to a loss of radial traction on the airway wall and subsequent narrowing of the airway.

Asthma can be characterized by contraction of airway smooth muscle, smooth muscle hypertrophy, excessive mucus production, mucous gland hypertrophy, and/or inflammation and swelling of airways. These abnormalities are the result of a complex interplay of local inflammatory cytokines (chemicals released locally by immune cells located in or near the airway wall), inhaled irritants (e.g., cold air, smoke, allergens, or other chemicals), systemic hormones (chemicals in the blood such as the anti-inflammatory cortisol and the stimulant epinephrine), local nervous system input (nerve cells contained completely within the airway wall that can produce local reflex stimulation of smooth muscle cells and mucous glands), and the central nervous system input (nervous system signals from the brain to smooth muscle cells and mucous glands carried through the vagus nerve). These conditions often cause widespread temporary tissue alterations and initially reversible airflow obstruction that may ultimately lead to permanent tissue alteration and permanent airflow obstruction that make it difficult for the asthma sufferer to breathe. Asthma can further include acute episodes or attacks of additional airway narrowing via contraction of hyper-responsive airway smooth muscle that significantly increases airflow resistance. Asthma symptoms include recurrent episodes of breathlessness (e.g., shortness of breath or dyspnea), wheezing, chest tightness, and cough.

Emphysema is a type of COPD often characterized by the alteration of lung tissue surrounding or adjacent to the airways in the lungs. Emphysema can involve destruction of lung tissue (e.g., alveoli tissue such as the alveolar sacs) that leads to reduced gas exchange and reduced radial traction applied to the airway wall by the surrounding lung tissue. The destruction of alveoli tissue leaves areas of emphysematous lung with overly large airspaces that are devoid of alveolar walls and alveolar capillaries and are thereby ineffective at gas exchange. Air becomes "trapped" in these larger airspaces. This "trapped" air may cause over-inflation of the lung, and in the confines of the chest restricts the in-flow of oxygen rich air and the proper function of healthier tissue. This results in significant breathlessness and may lead to low oxygen levels and high carbon dioxide levels in the blood. This type of lung tissue destruction occurs as part of the normal aging process, even in healthy individuals. Unfortunately, exposure to chemicals or other substances (e.g., tobacco smoke) may significantly accelerate the rate of tissue damage or destruction. Breathlessness may be further increased by airway obstruction. The reduction of radial traction may cause the airway walls to become "floppy" such that the airway walls partially or fully collapse during exhalation. An individual with emphysema may be unable to deliver air out of their lungs due to this airway collapse and airway obstructions during exhalation.

Chronic bronchitis is a type of COPD that can be characterized by contraction of the airway smooth muscle, smooth muscle hypertrophy, excessive mucus production, mucous gland hypertrophy, and inflammation of airway walls. Like asthma, these abnormalities are the result of a complex interplay of local inflammatory cytokines, inhaled irritants, systemic hormones, local nervous system, and the central nervous system. Unlike asthma where respiratory obstruction may be largely reversible, the airway obstruction in chronic bronchitis is primarily chronic and permanent. It is often difficult for a chronic bronchitis sufferer to breathe because of chronic symptoms of shortness of breath, wheezing, and chest tightness, as well as a mucus producing cough.

Different techniques can be used to assess the severity and progression of pulmonary diseases. For example, pulmonary function tests, exercise capacity, and quality of life questionnaires are often used to evaluate subjects. Pulmonary function tests involve objective and reproducible measures of basic physiologic lung parameters, such as total airflow, lung volume, and gas exchange. Indices of pulmonary function tests used for the assessment of obstructive pulmonary diseases include the forced expiratory volume in 1 second (FEV1), the forced vital capacity (FVC), the ratio of the FEV1 to FVC, the total lung capacity (TLC), airway resistance and the testing of arterial blood gases. The FEV1 is the volume of air a patient can exhale during the first second of a forceful exhalation which starts with the lungs completely filled with air. The FEV1 is also the average flow that occurs during the first second of a forceful exhalation. This parameter may be used to evaluate and determine the presence and impact of any airway obstruction. The FVC is the total volume of air a patient can exhale during a forceful exhalation that starts with the lungs completely filled with air. The FEV1/FVC is the fraction of all the air that can be exhaled during a forceful exhalation during the first second. A FEV1/FVC ratio less than 0.7 after the administration of at least one bronchodilator defines the presence of COPD. The TLC is the total amount of air within the lungs when the lungs are completely filled and may increase when air becomes trapped within the lungs of patients with obstructive lung disease. Airway resistance is defined as the pressure gradient between the alveoli and the mouth to the rate of air flow between the alveoli and the mouth. Similarly, resistance of a given airway would be defined as the ratio of the pressure gradient across the given airway to the flow through the airway. Arterial blood gases tests measure the amount of oxygen and the amount of carbon dioxide in the blood and are the most direct method for assessing the ability of the lungs and respiratory system to bring oxygen from the air into the blood and to get carbon dioxide from the blood out of the body.

Exercise capacity tests are objective and reproducible measures of a patient's ability to perform activities. A six minute walk test (6 MWT) is an exercise capacity test in which a patient walks as far as possible over a flat surface in 6 minutes. Another exercise capacity test involves measuring the maximum exercise capacity of a patient. For example, a physician can measure the amount of power the patient can produce while on a cycle ergometer. The patient can breathe 30 percent oxygen and the work load can increase by 5-10 watts every 3 minutes.

Quality of life questionnaires assess a patient's overall health and well being. The St. George's Respiratory Questionnaire is a quality of life questionnaire that includes 75 questions designed to measure the impact of obstructive lung disease on overall health, daily life, and perceived well-being. The efficacy of a treatment for pulmonary diseases can be evaluated using pulmonary function tests, exercise capacity tests, and/or questionnaires. A treatment program can be modified based on the results from these tests and/or questionnaires.

Treatments, such as bronchial thermoplasty, involve destroying smooth muscle tone by ablating the airway wall in a multitude of bronchial branches within the lung thereby eliminating both smooth muscles and nerves in the airway walls of the lung. The treated airways are unable to respond favorably to inhaled irritants, systemic hormones, and both local and central nervous system input. Unfortunately, this destruction of smooth muscle tone and nerves in the airway wall may therefore adversely affect lung performance. For example, inhaled irritants, such as smoke or other noxious substances, normally stimulate lung irritant receptors to produce coughing and contracting of airway smooth muscle. Elimination of nerves in the airway walls removes both local nerve function and central nervous input, thereby eliminating the lung's ability to expel noxious substances with a forceful cough. Elimination of airway smooth muscle tone may eliminate the airways' ability to constrict, thereby allowing deeper penetration of unwanted substances, such as noxious substances, into the lung.

Both asthma and COPD are serious diseases with growing numbers of sufferers. Current management techniques, which include prescription drugs, are neither completely successful nor free from side effects. Additionally, many patients do not comply with their drug prescription dosage regiment. Accordingly, it would be desirable to provide a treatment which improves resistance to airflow without the need for patient compliance.

BRIEF SUMMARY

At least some embodiments are directed to an intraluminal apparatus that denervates hollow organs while preventing, minimizing, or limiting the potential for stenosis. Targeted regions of an organ can be treated without unwanted stenosis that significantly affects organ function. In certain embodiments, the intraluminal apparatus ablates discrete targeted regions spaced apart from one another. Even if stenosis occurs, a continuous stenosis ring extending 360 degrees can be avoided. If the organ is an airway, lesions can be formed without any appreciable increase in airflow resistance.

In some embodiments, a system for treating a subject includes an elongate assembly dimensioned to move along a lumen of an airway. The assembly can attenuate signals transmitted by nerve tissue, such as nerve tissue of nerve trunks, while not irreversibly damaging to any significant extent an inner surface of the airway. In certain embodiments, one or more electrodes output radiofrequency energy to treat a posterior 90 degrees to 180 degrees of an airway circumference to denervate a lung. A cooling systems (e.g., cooling channels) can control the temperature of the electrodes and/or airway tissue while damaging the targeted tissue.

The tissue damage, in some procedures, may be sufficient to cause scarring, but the electrodes can be positioned to reduce, limit, or substantially eliminate appreciable narrowing of the airway lumen due to scar tissue, stenosis, etc. Lesions can be sufficiently spaced apart to prevent thickening of tissue between adjacent lesions. At least some embodiments disclosed herein can ablate substantially the entire circumference of an airway wall without forming a continuous ring of ablated tissue lying in a plane, which is perpendicular to a long axis of the airway.

In some embodiments, a method comprises damaging nerve tissue of a first main bronchus to substantially prevent nervous system signals from traveling to substantially all distal bronchial branches connected to the first main bronchus. Most or all of the bronchial branches distal to the first main bronchus do not receive nervous system signals. The nerve tissue, in certain embodiments, is positioned between a trachea and a lung through which the bronchial branches extend. The method further includes damaging nerve tissue of a second main bronchus to substantially prevent nervous system signals from traveling to substantially all distal bronchial branches connected to the second main bronchus. In certain embodiments, energy is delivered along less than 180° of the posterior airway or a desired portion of the airway circumference. This limits the amount of tissue that is exposed to the emitted energy.

Denervation, in some embodiments, involves the creation of lesions that affect the outside adventitial tissue layers where nerve trunks are anatomically located. In lung denervation, ablating nerve trunks which traverse along the outside of both the right and left main bronchi effectively disconnects airway smooth muscle which lines the inside of the lung airways and mucus producing glands located with the airways from the vagus nerve. When this occurs, airway smooth muscle relaxes and mucus production is decreased. These changes reduce airway obstruction under states of disease, such as COPD and asthma. Reduced airway obstruction makes breathing easier which improves a subject's quality of life and health status.

The nerve tissue can be thermally damaged by increasing a temperature of the nerve tissue to a first temperature (e.g., an ablation temperature) while the wall of the airway is at a second temperature that is less than the first temperature. In some embodiments, a portion of the airway wall positioned radially inward from the nerve tissue can be at the first temperature so as to prevent permanent damage to the portion of the airway wall. The first temperature can be sufficiently high to cause permanent destruction of the nerve tissue. In some embodiments, the nerve tissue is part of a nerve trunk located in connective tissue outside of the airway wall. The smooth muscle and nerve tissue in the airway wall can remain functional to maintain a desired level of smooth muscle tone. The airway can constrict/dilate in response to stimulation (e.g., stimulation caused by inhaled irritants, the local nervous system, or systemic hormones). In other embodiments, the nerve tissue is part of a nerve branch or nerve fibers in the airway wall. In yet other embodiments, both nerve tissue of the nerve trunk and nerve tissue of nerve branches/fibers are simultaneously or sequentially damaged. Various types of activatable elements, such as ablation elements, can be utilized to output the energy.

Some embodiments take advantage of large airway anatomy. Airway nerve trunks of the vagus nerve often reside along the posterior half of the main bronchial airways. The posterior area of the main airways (i.e. tracheal, right and left main bronchus) does not have cartilage. The cartilage rings of these airways are not fully circumferential and only soft tissue is present along their posterior. Further, damaging nerve tissue from airway nerve trunks which reside on the posterior half of the airways can be accomplished by creating lesions that are less (e.g., significantly less) than the 360 degrees of the airway circumference. For example, treating 180 degrees, 150 degrees, or 130 degrees of airway circumference may be all that is required to effectively denervate the airway. Since the lesion has an arc length significantly less than 360 degrees, airway stenosis can be greatly reduced or prevented.

Electrodes can have complex shapes, including arcuate shapes, polygonal shapes, or have any other shapes or configurations. The electrodes can be V-shaped, U-shaped, L-shaped, T-shaped, W-shaped, straight, curved, or combinations thereof. In some embodiments, an electrode assembly has a zigzag configuration, a serpentine configuration, a wound or coiled configuration, a corkscrew configuration, a helical configuration, z-shaped configuration, combinations thereof, or the like. A corkscrew-shaped electrode assembly can have independently operatable electrodes that form a discontinuous or continuous generally corkscrew-shaped lesion.

Another embodiment includes a continuous electrode assembly capable of creating a generally corkscrew-shaped lesion along a part or all of the airway circumference. Scars that have less surface area for the same circumferential region are less likely to generate tissue webs that can form stenosis. At least some embodiments can treat narrow target regions to form corresponding narrow lesions. A knife edge electrode assembly can perform such treatments to further reduce scar tissue.

Yet another embodiment relies on nerves, arteries, and veins tending to travel in groups throughout the human anatomy. Ultrasound or other type of energy can be used to determine the location of the bronchial arteries or veins which travel in close proximity to airway nerve trunks prior to performing airway denervation. After determining the locations of the blood vessels, the airway area in proximity to the blood vessels is treated with energy to ablate the airway nerve trunks. This technique minimizes or limits the volume of treated tissue to reduce or eliminate the risk for stenosis.

In some procedures, a catheter shapes at least one lesion at a desired depth. For example, one or more corkscrew-shaped or helical-shaped lesions can be formed in one bronchial airway wall and an arcuate lesion can be formed in another airway wall to denervate different portions of a bronchial tree. The lesions can be located along an inner surface of an airway or deep within the airway wall, or along an outer surface of the airway.

An energy delivery device, in some embodiments, comprises a catheter shaft and an ablation assembly coupled to the catheter shaft. The ablation assembly includes a cooling element movable from a collapsed state to an expanded state and an intercartilaginous energy emitter including a plurality of electrodes circumferentially offset from one another about a longitudinal axis of the ablation assembly. The electrodes are configured to delivery energy to a plurality of target regions of an airway that are spaced apart from one another with respect to the longitudinal axis of the airway. The energy emitter and the cooling element are configured to cooperate to form intercartilaginous lesions which are spaced apart from surface tissue of the airway and positioned between cartilaginous rings of the airway.

In certain embodiments, an intraluminal delivery device comprises an ablation assembly including an expandable device and a plurality of ablation elements and/or electrodes. The electrodes are spaced apart about a circumference of the expandable member and capable of outputting energy to discrete target regions to form lesions at the target regions. At least a portion of a first lesion is axially spaced apart from and circumferentially adjacent to or overlapping a second lesion.

In some embodiment, a method of treating a subject comprises positioning an ablation assembly with respect to an airway and outputting energy from the ablation assembly to axially spaced apart target regions of the airway. The profiles of the target regions overlap when viewed in a direction along a long axis of the airway.

In yet other embodiments, a method of treating a subject comprises moving an energy emitter of a delivery device along an airway. At least one electrode of the energy emitter is positioned between cartilaginous rings of the airway. Energy is delivered from the electrode to target regions at axially separated locations along a long axis of the airway to form inter-cartilaginous lesions.

Some methods of treating tissue comprise positioning an ablation assembly in a lumen of an airway and delivering energy to tissue of the airway using at least one electrode of the ablation assembly positioned near an inner surface of the airway. Energy is delivered to damage target regions axially separated along the airway such that portions of the target regions defining maximum cross-sectional widths of the target regions are separated from the inner surface of the airway.

A delivery device, in some embodiments, comprises a catheter shaft and an ablation assembly coupled to the catheter shaft. The ablation assembly includes a deployable element movable from a collapsed state to an expanded state. An energy emitter is capable of emitting energy to produce lesions that have ends axially displaced from one another along an axial length of a body structure when the expandable member is in the deployed state.

A delivery device can produce one or more lesions that are continuous or discontinuous. The lesions can have different shapes, including arcuate shapes, spiral shapes, helical shapes, wavy shapes, serpentine shapes, or combinations thereof. For producing continuous lesions, an ablation assembly can have electrodes spaced close together to form generally continuous lesions. Alternatively, the ablation assembly can have a long electrode or energy emitter that has corresponding spiral shapes, helical shapes, serpentine shapes, or the like. In other embodiments, electrodes can be spaced apart a sufficient distance to form discontinuous lesions. The pattern, spacing, and size of the lesions can be selected to treat target regions.

In certain embodiments, lesions can be simultaneously formed at different locations along the airway wall. In some procedures, oblique lesions can be formed at opposite sides of the airway. An entire lesion can be positioned between cartilaginous rings to avoid damaging the rings. In other embodiments, lesions can traverse tracheal or cartilaginous rings.

BRIEF DESCRIPTION OF THE DRAWINGS

In the Figures, identical reference numbers identify similar elements or acts.

DETAILED DESCRIPTION

Figure 1:
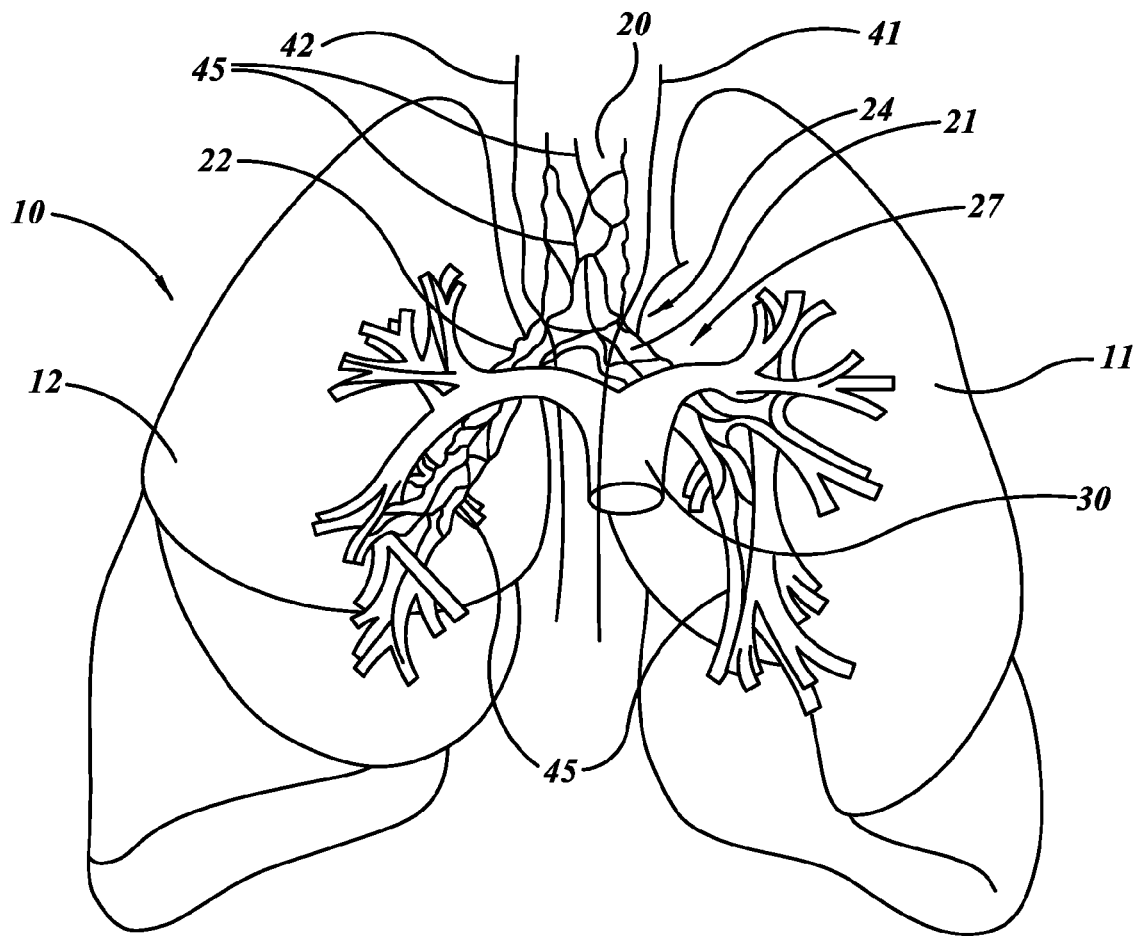
FIG. 1 is an illustration of lungs, blood vessels, and nerves near to and in the lungs.

FIG. 1 illustrates human lungs 10 having a left lung 11 and a right lung 12. A trachea 20 extends downwardly from the nose and mouth and divides into a left main bronchus 21 and a right main bronchus 22. The left main bronchus 21 and right main bronchus 22 each branch to form lobar, segmental bronchi, and sub-segmental bronchi, which have successively smaller diameters and shorter lengths in the outward direction (i.e., the distal direction). A main pulmonary artery 30 originates at a right ventricle of the heart and passes in front of a lung root 24. At the lung root 24, the artery 30 branches into a left and right pulmonary artery, which in turn branch to form a network of branching blood vessels. These blood vessels can extend alongside airways of a bronchial tree 27. The bronchial tree 27 includes the left main bronchus 21, the right main bronchus 22, bronchioles, and alveoli. Vagus nerves 41, 42 extend alongside the trachea 20 and branch to form nerve trunks 45.

The left and right vagus nerves 41, 42 originate in the brainstem, pass through the neck, and descend through the chest on either side of the trachea 20. The vagus nerves 41, 42 spread out into nerve trunks 45 that include the anterior and posterior pulmonary plexuses that wrap around the trachea 20, the left main bronchus 21, and the right main bronchus 22. The nerve trunks 45 also extend along and outside of the branching airways of the bronchial tree 27. Nerve trunks 45 are the main stem of a nerve, comprising a bundle of nerve fibers bound together by a tough sheath of connective tissue.

The primary function of the lungs 10 is to exchange oxygen from air into the blood and to exchange carbon dioxide from the blood to the air. The process of gas exchange begins when oxygen rich air is pulled into the lungs 10. Contraction of the diaphragm and intercostal chest wall muscles cooperate to decrease the pressure within the chest to cause the oxygen rich air to flow through the airways of the lungs 10. For example, air passes through the mouth and nose, the trachea 20, then through the bronchial tree 27. The air is ultimately delivered to the alveolar air sacs for the gas exchange process.

Oxygen poor blood is pumped from the right side of the heart through the pulmonary artery 30 and is ultimately delivered to alveolar capillaries. This oxygen poor blood is rich in carbon dioxide waste. Thin semi-permeable membranes separate the oxygen poor blood in capillaries from the oxygen rich air in the alveoli. These capillaries wrap around and extend between the alveoli. Oxygen from the air diffuses through the membranes into the blood, and carbon dioxide from the blood diffuses through the membranes to the air in the alveoli. The newly oxygen enriched blood then flows from the alveolar capillaries through the branching blood vessels of the pulmonary venous system to the heart. The heart pumps the oxygen rich blood throughout the body. The oxygen spent air in the lung is exhaled when the diaphragm and intercostal muscles relax and the lungs and chest wall elastically return to the normal relaxed states. In this manner, air can flow through the branching bronchioles, the bronchi 21, 22, and the trachea 20 and is ultimately expelled through the mouth and nose.

Figure 2:
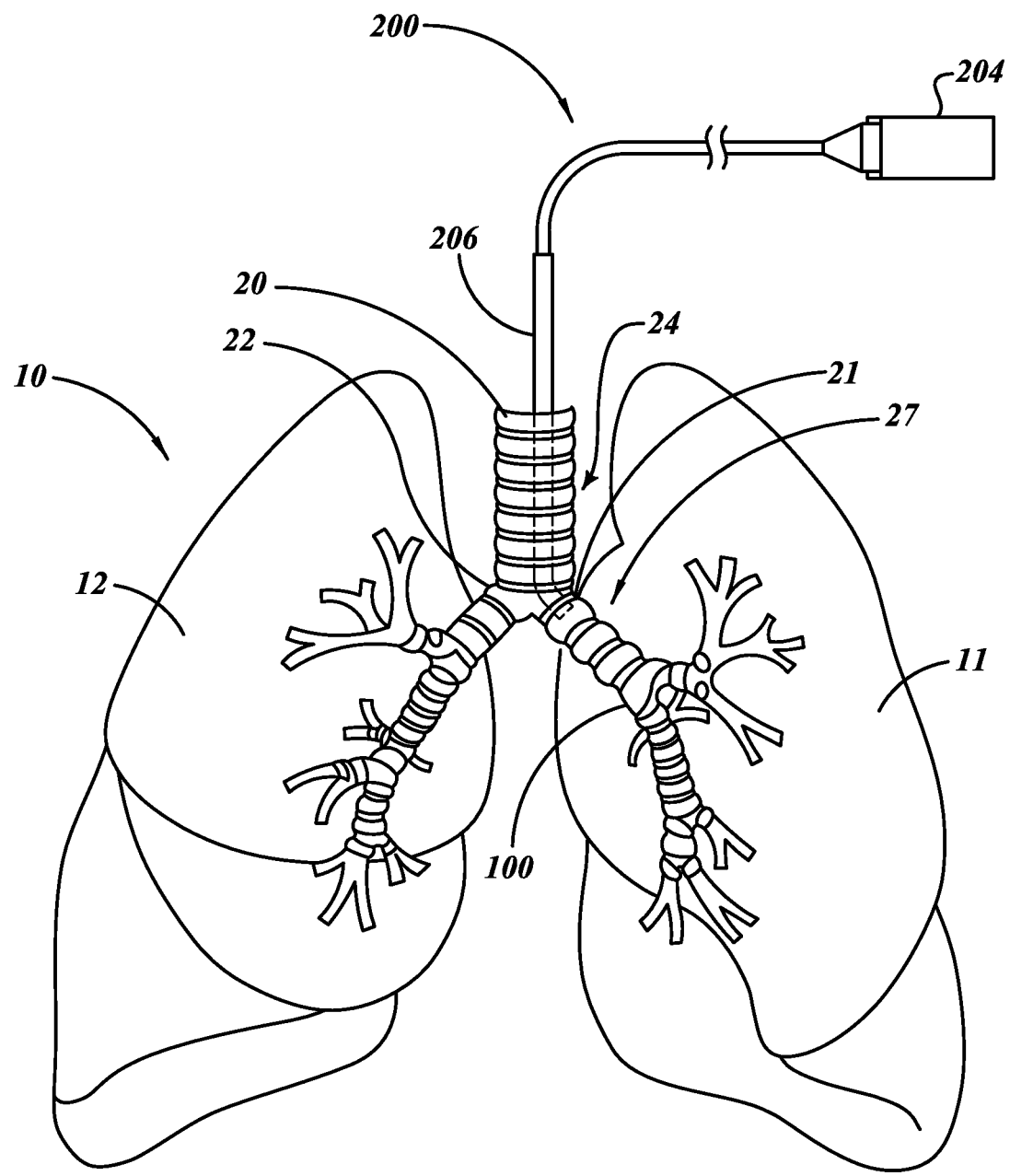
FIG. 2 is an illustration of an intraluminal treatment system positioned within a left main bronchus according to one embodiment.

FIG. 2 shows a treatment system 200 capable of performing treatments to adjust air flow during expiration or inhalation, or both. To decrease airflow resistance to increase gas exchange, the treatment system 200 can be used to enlarge (e.g., dilate) airways. In some procedures, nerve tissue (e.g., nerve tissue) of a nerve trunk (inside or outside of the lungs), can be affected to dilate airways. The nervous system provides communication between the brain and the lungs 10 using electrical and chemical signals. A network of nerve tissue of the autonomic nervous system senses and regulates activity of the respiratory system and the vasculature system. Nerve tissue includes fibers that use chemical and electrical signals to transmit sensory and motor information from one body part to another. For example, the nerve tissue can transmit motor information in the form of nervous system input, such as a signal that causes contraction of muscles or other responses. The fibers can be made up of neurons. The nerve tissue can be surrounded by connective tissue, i.e., epineurium. The autonomic nervous system includes a sympathetic system and a parasympathetic system. The sympathetic nervous system is largely involved in "excitatory" functions during periods of stress. The parasympathetic nervous system is largely involved in "vegetative" functions during periods of energy conservation. The sympathetic and parasympathetic nervous systems are simultaneously active and generally have reciprocal effects on organ systems. While innervation of the blood vessels originates from both systems, innervation of the airways is largely parasympathetic in nature and travels between the lung and the brain in the right vagus nerve 42 and the left vagus nerve 41.

Any number of procedures can be performed on one or more of these nerve trunks 45 to affect the portion of the lung associated with those nerve trunks. Because some of the nerve tissue in the network of nerve trunks 45 coalesce into other nerves (e.g., nerves connected to the esophagus, nerves though the chest and into the abdomen, and the like), specific sites can be targeted to minimize, limit, or substantially eliminate unwanted damage of non-targeted nerves or structures. Some fibers of anterior and posterior pulmonary plexuses coalesce into small nerve trunks which extend along the outer surfaces of the trachea 20 and the branching bronchi and bronchioles as they travel outward into the lungs 10. Along the branching bronchi, these small nerve trunks continually ramify with each other and send fibers into the walls of the airways.

The treatment system 200 can affect specific nerve tissue, such as vagus nerve tissue, associated with particular sites of interest. Vagus nerve tissue includes efferent fibers and afferent fibers oriented parallel to one another within a nerve branch. The efferent nerve tissue transmits signals from the brain to airway effector cells, mostly airway smooth muscle cells and mucus producing cells. The afferent nerve tissue transmits signals from airway sensory receptors, which respond to irritants, and stretch to the brain. While efferent nerve tissue innervates smooth muscle cells all the way from the trachea 20 to the terminal bronchioles, the afferent fiber innervation is largely limited to the trachea 20 and larger bronchi. There is a constant, baseline tonic activity of the efferent vagus nerve tissues to the airways which causes a baseline level of smooth muscle contraction and mucous secretion. The treatment system 200 can affect the efferent and/or the afferent tissues to control airway smooth muscle (e.g., innervate smooth muscle), mucous secretion, nervous mediated inflammation, and tissue fluid content (e.g., edema). The contraction of airway smooth muscle, excess mucous secretion, inflammation, and airway wall edema associated with pulmonary diseases often results in relatively high airflow resistance causing reduced gas exchange and decreased lung performance.

In certain procedures, nerve tissue is ablated to attenuate the transmission of signals traveling along the vagus nerves 41, 42 that cause or mediate muscle contractions, mucus production, inflammation, edema, and the like. Attenuation can include, without limitation, hindering, limiting, blocking, and/or interrupting the transmission of signals. For example, the attenuation can include decreasing signal amplitude of nerve signals or weakening the transmission of nerve signals. Decreasing or stopping nervous system input to distal airways can alter airway smooth muscle tone, airway mucus production, airway inflammation, and the like, thereby controlling airflow into and out of the lungs 10. Decreasing or stopping sensory input from the airways and lungs to local effector cells or to the central nervous system can also decrease reflex bronchoconstriction, reflex mucous production, release of inflammatory mediators, and nervous system input to other cells in the lungs or organs in the body that may cause airway wall edema. In some embodiments, the nervous system input can be decreased to correspondingly decrease airway smooth muscle tone. In some embodiments, the airway mucus production can be decreased a sufficient amount to cause a substantial decrease in coughing and/or in airflow resistance. In some embodiments, the airway inflammation can be decreased a sufficient amount to cause a substantial decrease in airflow resistance and ongoing inflammatory injury to the airway wall. Signal attenuation may allow the smooth muscles to relax, prevent, limit, or substantially eliminate mucus production by mucous producing cells, and decrease inflammation. In this manner, healthy and/or diseased airways can be altered to adjust lung function. After treatment, various types of questionnaires or tests can be used to assess the subject's response to the treatment. If needed or desired, additional procedures can be performed to reduce the frequency of coughing, decrease breathlessness, decrease wheezing, and the like.

Main bronchi 21, 22 (i.e., airway generation 1) of FIGS. 1 and 2 can be treated to affect distal portions of the bronchial tree 27. In some embodiments, the left and right main bronchi 21, 22 are treated at locations along the left and right lung roots 24 and outside of the left and right lungs 11, 12. Treatment sites can be distal to where vagus nerve branches connect to the trachea and the main bronchi 21, 22 and proximal to the lungs 11, 12. A single treatment session involving two therapy applications can be used to treat most of or the entire bronchial tree 27. Substantially all of the bronchial branches extending into the lungs 11, 12 may be affected to provide a high level of therapeutic effectiveness. Because the bronchial arteries in the main bronchi 21, 22 have relatively large diameters and high heat sinking capacities, the bronchial arteries may be protected from unintended damage due to the treatment.

Figure 3:
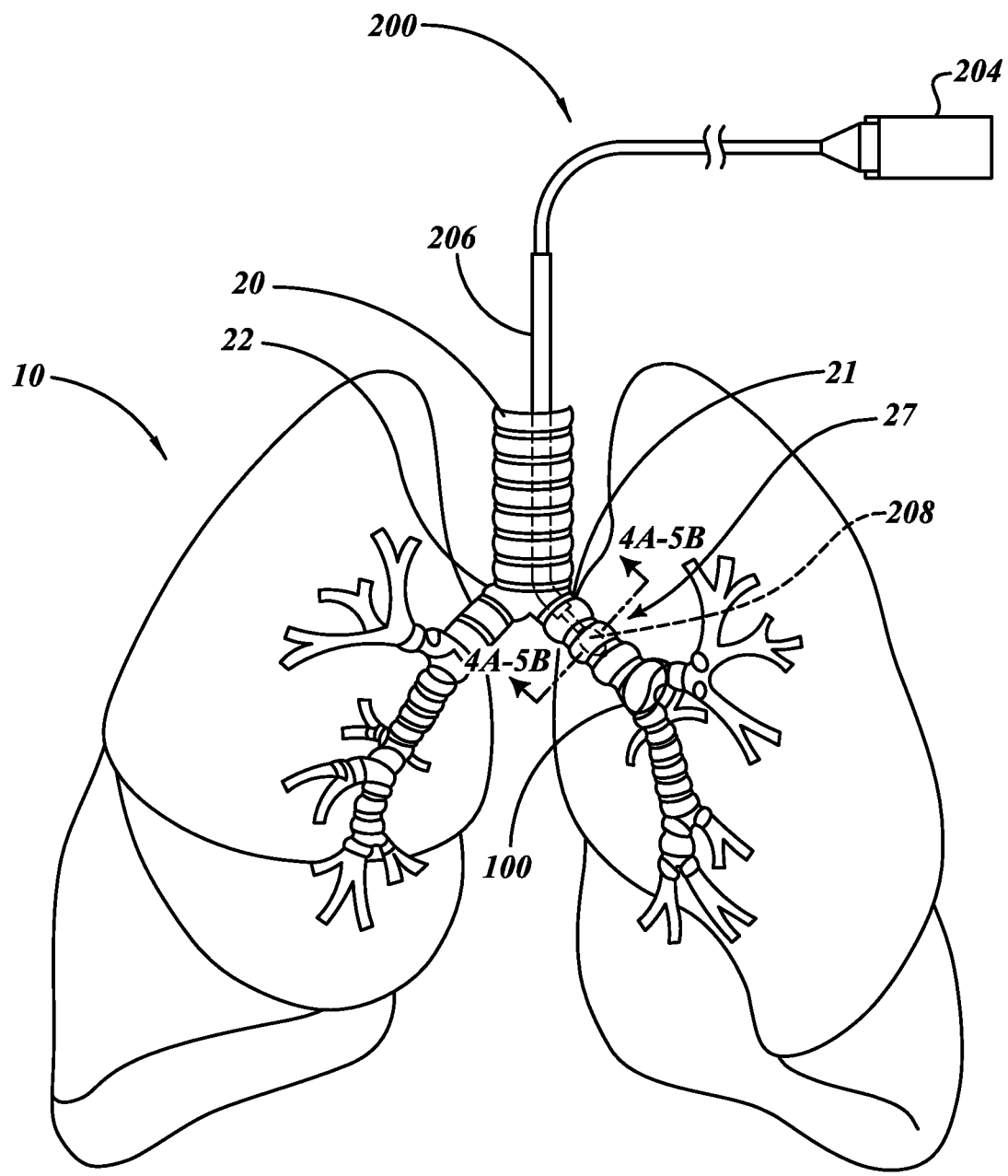
FIG. 3 is an illustration of a delivery device extending from an access apparatus positioned in the left main bronchus.

FIG. 3 shows a delivery device in the form of a catheter system 204 extending through an access apparatus 206. The catheter system 204 can treat airways of the main bronchi 21, 22, as well as airways that are distal to the main bronchi 21, 22. An ablation assembly 208 can be positioned outside the lung within the right or left main bronchi, the lobar bronchii, or the intermediate bronchus. The intermediate bronchus is formed by a portion of the right main bronchus and the origin of the middle and lower lobar bronchii. The ablation assembly 208 can also be positioned in high generation airways (e.g., airway generations>2) to affect remote distal portions of the bronchial tree 27.

The catheter system 204 can be navigated through tortuous airways to perform a wide range of different procedures, such as, for example, denervation of a portion of a lobe, an entire lobe, multiple lobes, or one lung or both lungs. In some embodiments, the lobar bronchi are treated to denervate lung lobes. For example, one or more treatment sites along a lobar bronchus may be targeted to denervate an entire lobe connected to that lobar bronchus. Left lobar bronchi can be treated to affect the left superior lobe and/or the left inferior lobe. Right lobar bronchi can be treated to affect the right superior lobe, the right middle lobe, and/or the right inferior lobe. Lobes can be treated concurrently or sequentially. In some embodiments, a physician can treat one lobe. Based on the effectiveness of the treatment, the physician can concurrently or sequentially treat additional lobe(s). In this manner, different isolated regions of the bronchial tree can be treated.

Each segmental bronchus may be treated by delivering energy to a single treatment site along each segmental bronchus. For example, energy can be delivered to each segmental bronchus of the right lung. In some procedures, ten applications of energy can treat most of or substantially all of the right lung. In some procedures, most or substantially all of both lungs are treated using less than thirty-six different applications of energy. Depending on the anatomical structure of the bronchial tree, segmental bronchi can often be denervated using one or two applications of energy.

Function of other tissue or anatomical features, such as the mucous glands, cilia, smooth muscle, body vessels (e.g., blood vessels), and the like can be maintained when nerve tissue is ablated. Nerve tissue includes nerve cells, nerve fibers, dendrites, and supporting tissue, such as neuroglia. Nerve cells transmit electrical impulses, and nerve fibers are prolonged axons that conduct the impulses. The electrical impulses are converted to chemical signals to communicate with effector cells or other nerve cells. By way of example, a portion of an airway of the bronchial tree 27 can be denervated to attenuate one or more nervous system signals transmitted by nerve tissue. Denervating can include damaging all of the nerve tissue of a section of a nerve trunk along an airway to stop substantially all the signals from traveling through the damaged section of the nerve trunk to more distal locations along the bronchial tree or from the bronchial tree more proximally to the central nervous system. Additionally, signals that travel along nerve fibers that go directly from sensory receptors (e.g., cough and irritant receptors) in the airway to nearby effector cells (e.g., postganglionic nerve cells, smooth muscle cells, mucous cells, inflammatory cells, and vascular cells) will also be stopped. If a plurality of nerve trunks extends along the airway, each nerve trunk can be damaged. As such, the nerve supply along a section of the bronchial tree can be cut off. When the signals are cut off, the distal airway smooth muscle can relax leading to airway dilation, mucous cells decrease mucous production, or inflammatory cells stop producing airway wall swelling and edema. These changes reduce airflow resistance so as to increase gas exchange in the lungs 10, thereby reducing, limiting, or substantially eliminating one or more symptoms, such as breathlessness, wheezing, chest tightness, and the like. Tissue surrounding or adjacent to the targeted nerve tissue may be affected but not permanently damaged. In some embodiments, for example, the bronchial blood vessels along the treated airway can deliver a similar amount of blood to bronchial wall tissues and the pulmonary blood vessels along the treated airway can deliver a similar amount of blood to the alveolar sacs at the distal regions of the bronchial tree 27 before and after treatment. These blood vessels can continue to transport blood to maintain sufficient gas exchange. In some embodiments, airway smooth muscle is not damaged to a significant extent. For example, a relatively small section of smooth muscle in an airway wall which does not appreciably impact respiratory function may be reversibly altered. If energy is used to destroy the nerve tissue outside of the airways, a therapeutically effective amount of energy does not reach a significant portion of the non-targeted smooth muscle tissue.

One of the left and right main bronchi 21, 22 is treated to treat one side of the bronchial tree 27. The other main bronchus 21, 22 can be treated based on the effectiveness of the first treatment. For example, the left main bronchus 21 can be treated to treat the left lung 11. The right main bronchus 22 can be treated to treat the right lung 12. In some embodiments, a single treatment system can damage the nerve tissue of one of the bronchi 21, 22 and can damage the nerve tissue of the other main bronchus 21, 22 without removing the treatment system from the trachea 20. Nerve tissue positioned along the main bronchi 21, 22 can thus be damaged without removing the treatment system from the trachea 20. In some embodiments, a single procedure can be performed to conveniently treat substantially all, or at least a significant portion (e.g., at least 50%, 70%, 80%, 90% of the bronchial airways), of the patient's bronchial tree. In other procedures, the treatment system can be removed from the patient after treating one of the lungs 11, 12. If needed, the other lung 11, 12 can be treated in a subsequent procedure.

Figure 4A:
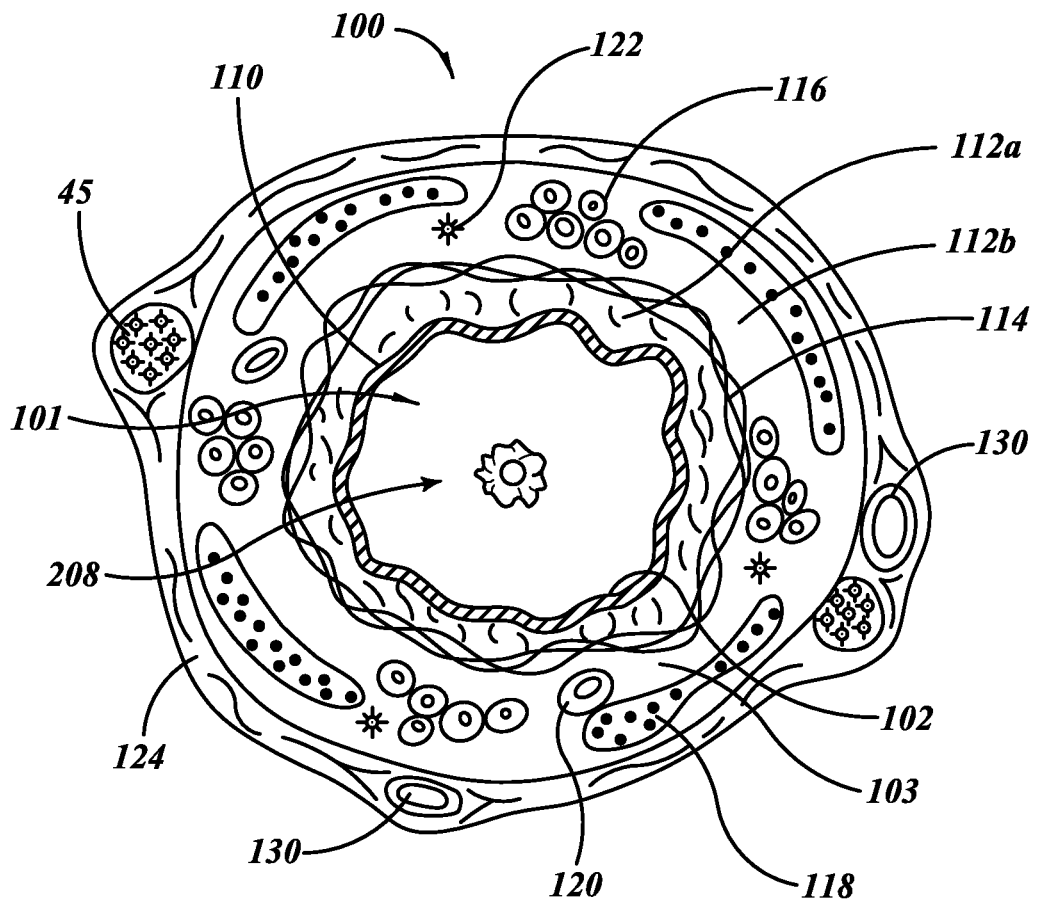
FIG. 4A is a cross-sectional view of an airway of a bronchial tree and a collapsed ablation assembly.

FIG. 4A is a transverse cross-sectional view of a healthy airway 100, illustrated as a bronchial tube. The inner surface 102 is defined by a folded layer of epithelium 110 surrounded by stroma 112*a*. A layer of smooth muscle tissue 114 surrounds the stroma 112*a*. A layer of stroma 112*b* is between the muscle tissue 114 and connective tissue 124. Mucous glands 116, cartilage plates 118, blood vessels 120, and nerve fibers 122 are within the stroma layer 112*b*. Bronchial artery branches 130 and nerve trunks 45 are exterior to a wall 103 of the airway 100. The illustrated arteries 130 and nerve trunks 45 are within the connective tissue 124 surrounding the airway wall 103 and can be oriented generally parallel to the airway 100. In FIG. 1, for example, the nerve trunks 45 originate from the vagus nerves 41, 42 and extend along the airway 100 towards the air sacs. The nerve fibers 122 are in the airway wall 103 and extend from the nerve trunks 45 to the muscle tissue 114. Nervous system signals are transmitted from the nerve trunks 45 to the muscle 114 and mucous glands 116 via the nerve fibers 122. Additionally, signals are transmitted from sensory receptors (e.g., cough, irritant, and stretch) through the nerve trunks 45 to the central nervous system.

Cilia can be damaged, excited, or otherwise altered to elicit a desired response along the epithelium 110 in order to control (e.g., increase or decrease) mucociliary transport. Many particles are inhaled as a person breathes, and the airways function as a filter to remove the particles from the air. The mucociliary transport system functions as a self-cleaning mechanism for all the airways throughout the lungs 10. The mucociliary transport is a primary method for mucus clearance from distal portions of the lungs 10, thereby serving as a primary immune barrier for the lungs 10. For example, the inner surface 102 of FIG. 4A can be covered with cilia and coated with mucus. As part of the mucociliary transport system, the mucus entraps many inhaled particles (e.g., unwanted contaminates such as tobacco smoke) and moves these particles towards the larynx. The ciliary beat of cilia moves a continuous carpet of mucus and entrapped particles from the distal portions of the lungs 10 past the larynx and to the pharynx for expulsion from the respiratory system. The ablation assembly 208 can damage the cilia to decrease mucociliary transport or excite the cilia to increase mucociliary transport.

Figure 4B:
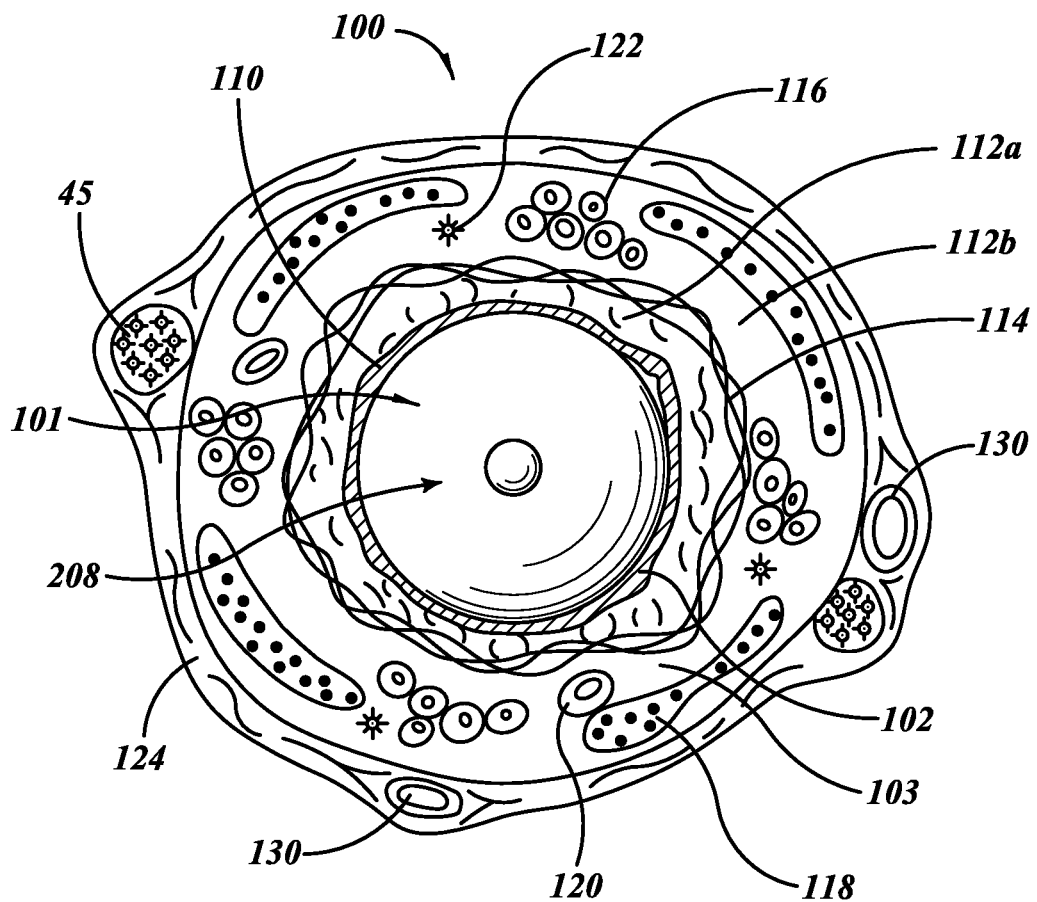
FIG. 4B is a cross-sectional view of an airway of a bronchial tree and an expanded ablation assembly.

The ablation assembly 208 is moved to the expanded state of FIG. 4B to selectively treat target regions inside of the airway wall 103 (e.g., anatomical features in the stromas 112a, 112b, the nerve trunk 45, etc.). For example, the mucous glands 116 can be damaged to reduce mucus production a sufficient amount to prevent the accumulation of mucus that causes increased airflow resistance while preserving enough mucus production to maintain effective mucociliary transport, if needed or desired. Nerve branches/fibers passing through the airway wall 103 or other anatomical features in the airway wall 103 can also be destroyed. The lesions are formed at specific locations to prevent stenosis or scar tissue that would significantly reduce the airflow through the airway 100.

Natural body functions can help prevent, reduce, or limit damage to tissue. Blood within the blood vessels 130 can absorb thermal energy and can then carry the thermal energy away from the heated section of the branches 130. In this manner, blood can mitigate or avoid damage to the blood vessels 130. After the treatment is performed, the bronchial artery branches 130 can continue to maintain the health of lung tissue. In some RF ablation embodiments, the ablation assembly 208 outputs a sufficient amount of RF energy to destroy an entire longitudinal section of the nerve trunk 45 without destroying the blood vessels 130.

Treatment efficacy can be evaluated based at least in part on one or more airway attributes, pulmonary function tests, exercise capacity tests, and/or questionnaires. Subjects can be evaluated to track and monitor their progress. If needed or desired, additional procedures can be performed until desired responses are achieved. Different types of instruments for evaluating airway attributes may be used. During ablation, feedback from an instrument can indicate whether the targeted tissue has been ablated. Once targeted tissue is ablated, therapy can be discontinued to minimize or limit collateral damage, if any, to healthy untargeted tissue.

Different attributes of airways can be evaluated to determine procedures to be performed. Such airway attributes include, without limitation, physical properties of airways (e.g., airway compliance, contractile properties, etc.), airway resistance, dimensions of airway lumens (e.g., shapes of airways, diameters of airways, etc.), responsiveness of airways (e.g., responsiveness to stimulation), muscle characteristics (e.g., muscle tone, muscle tension, etc.), inflammatory cells, inflammatory cytokines, or the like. In some embodiments, changes of airway muscle characteristics can be monitored by measuring pressure changes in the ablation assembly 208, which is inflated to a known pressure. Based on pressure changes, a physician determines the effects, if any, of the treatment, including, without limitation, whether targeted tissue has been stimulated, ablated, or the like.

Figure 5A:
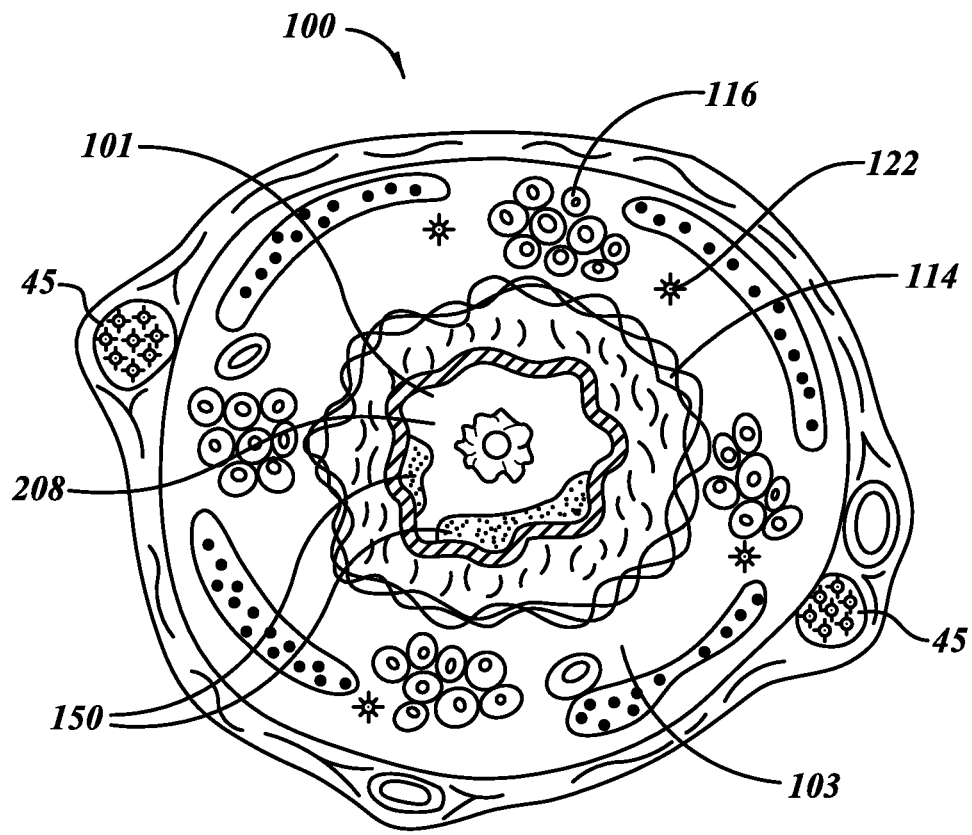
FIG. 5A is a cross-sectional view of an airway surrounding the collapsed ablation assembly when smooth muscle of the airway is constricted and mucus is in an airway lumen.
Figure 5B:
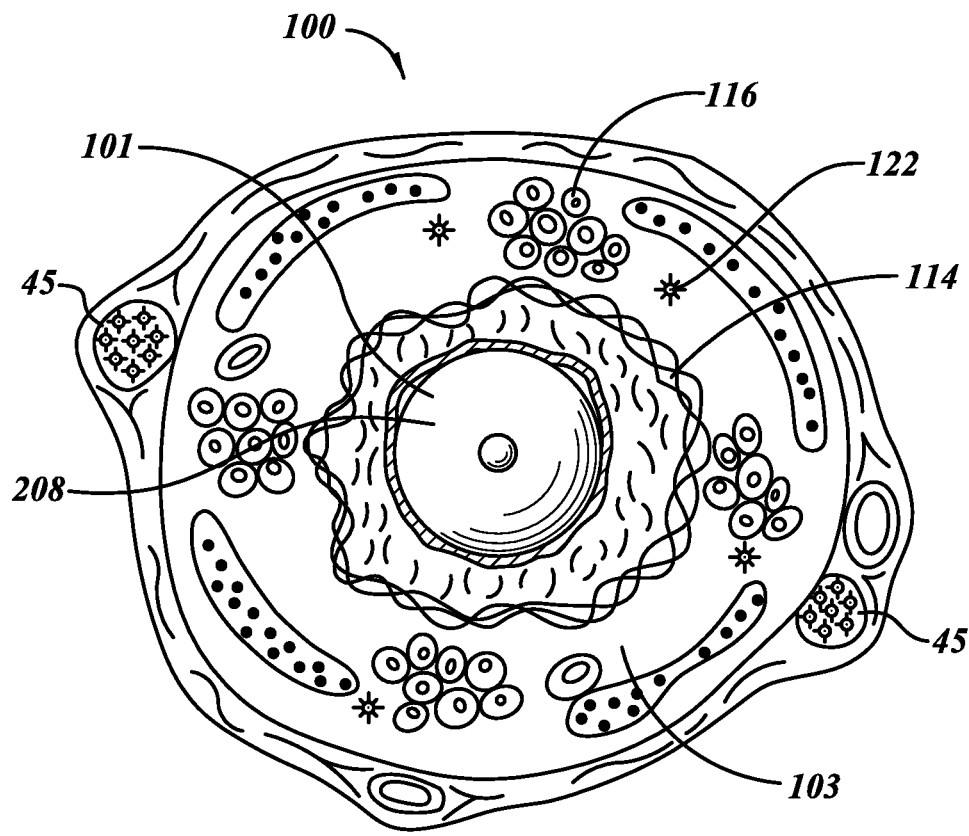
FIG. 5B is a cross-sectional view of the airway surrounding the expanded ablation assembly.

FIGS. 5A and 5B are transverse cross-sectional views of a portion of the airway 100 that has smooth muscle tissue 114 in a contracted state, mucus 150 from hypertrophied mucous glands 116, and inflammatory swelling and edema fluid thickening the airway wall 103. The contracted muscle tissue 114, the mucus 150, and thickened airway wall 103 cooperate to partially obstruct the lumen 101 resulting in a relatively high air flow resistance. The nerve tissue 45 is damaged to relax the muscle tissue 114 to dilate the airway 100 to reduce air flow resistance, thereby allowing more air to reach the alveolar sacs for the gas exchange process. Decreases in airway resistance may indicate that passageways of airways are opening, for example in response to attenuation of nervous system input to those airways. Stenosis can be limited or minimized to ensure that airway resistance does not significantly increase after treatment. Thus, the treatment ensures that there is a permanent decrease in airway flow resistance even after a significant length of time after treatment.

The decrease of airway resistance associated with treating low generation airways (e.g., main bronchi, lobar bronchi, segmental bronchi) may be greater than the amount of decrease of airway resistance associated with treating high generation airways (e.g., subsegmental bronchioles). A physician can select appropriate airways for treatment to achieve a desired decrease in airway resistance and can be measured at a patient's mouth, a bronchial branch that is proximate to the treatment site, a trachea, or any other suitable location. The airway resistance can be measured before performing the therapy, during the therapy, and/or after the therapy. In some embodiments, airway resistance is measured at a location within the bronchial tree by, for example, using a vented treatment system that allows for respiration from areas that are more distal to the treatment site.

The ablation assembly 208 can use energy to ablate the nerves 45 to permanently dilate the airway 100. As used herein, the term "energy" is broadly construed to include, without limitation, thermal energy, cryogenic energy (e.g., cooling energy), electrical energy, acoustic energy (e.g., ultrasonic energy), radio frequency energy, pulsed high voltage energy, mechanical energy, ionizing radiation, optical energy (e.g., light energy), and combinations thereof, as well as other types of energy suitable for treating tissue. In some embodiments, the catheter system 204 delivers energy and also one or more substances (e.g., radioactive seeds, radioactive materials, etc.), treatment agents, and the like. Exemplary non-limiting treatment agents include, without limitation, one or more antibiotics, anti-inflammatory agents, pharmaceutically active substances, bronchoconstrictors, bronchodilators (e.g., beta-adrenergic agonists, anticholinergics, etc.), nerve blocking drugs, photoreactive agents, or combinations thereof. For example, long acting or short acting nerve blocking drugs (e.g., anticholinergics) can be delivered to the nerve tissue to temporarily or permanently attenuate signal transmission. Substances can also be delivered directly to the nerves 122 or the nerve trunks 45, or both, to chemically damage the nerve tissue.

Figure 6:
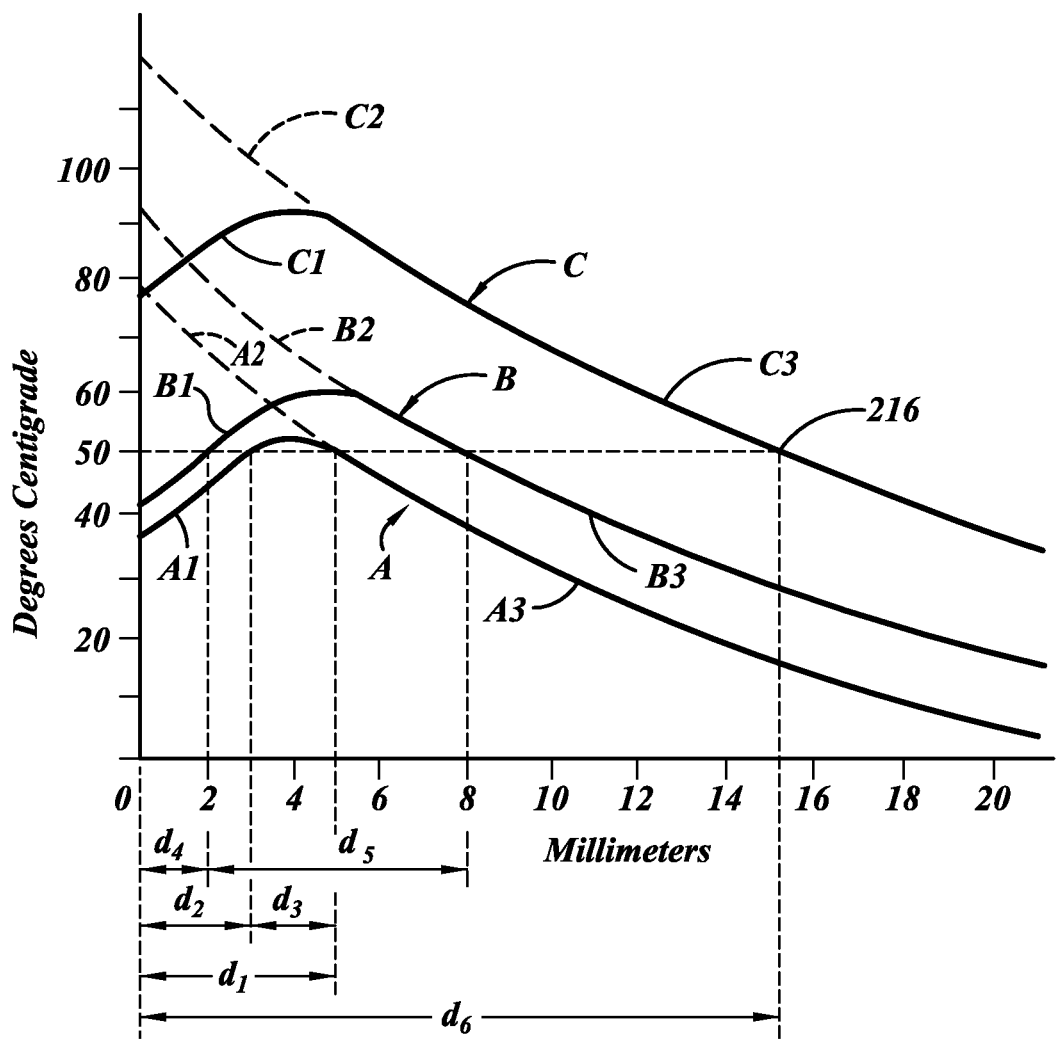
FIG. 6 is a graph of the depth of tissue versus the temperature of the tissue.
Figure 7:
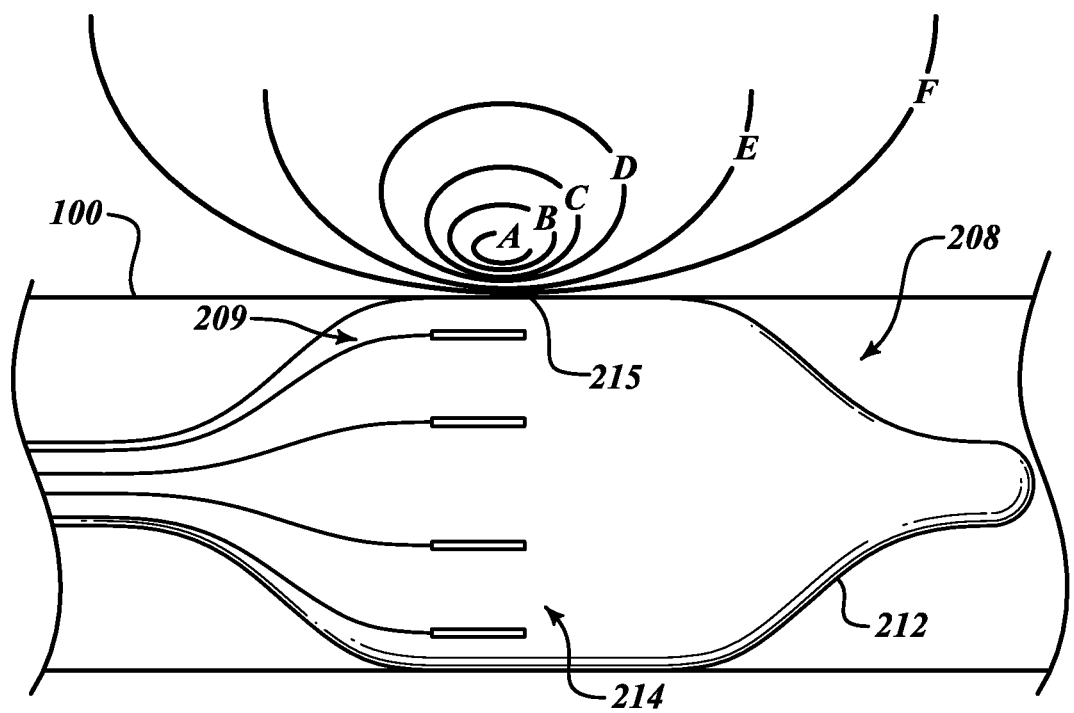
FIG. 7 is a side elevational view of an ablation assembly in an airway.

FIGS. 6 and 7 show the effect produced by superficial and deep heating by RF energy and superficial cooling by circulating coolant in the ablation assembly 208. The coolant absorbs thermal energy such that the tissue touching a cooling section 209 of the ablation assembly 208 is cooled. The cooling section 209 can absorb a sufficient amount of thermal energy from the airway wall 100 to limit or prevent damage to tissue between the ablation assembly 208 and the nerve or other targeted tissue.

FIG. 6 shows a graph with a horizontal axis corresponding to the depth into the tissue of the airway wall from the point of contact with or proximate to an electrode assembly 214 in millimeters with a vertical axis corresponding to the temperature of the tissue in degrees Centigrade. Temperatures in the figures are in degrees Centigrade, unless indicated otherwise. The point "0" on the graph corresponds to the point or area of contact between the electrode assembly 214 and the tissue of the airway wall. Three curves A, B, and C are shown in the graph and correspond to three different power levels of radio frequency energy being delivered into the tissue. The temperature on the graph is up to about 100° C. The temperature of about 100° C., or slightly less, has been shown because it is considered to be an upper limit for tissue temperature during RF ablation. At approximately 90° C., tissue fluids begin to boil and tissue coagulates and chars, thereby greatly increasing its impedance and compromising its ability to transfer RF energy into the tissue of the airway wall. Thus, it may be desirable to have tissue temperatures remain below about 90° C. At about 50° C., a line 216 represents the temperature above which tissue cell death occurs and below which tissues suffer no substantial long term effects (or any long term effects).

Curve A shown in FIG. 6 represents what occurs with and without cooling of the electrode assembly 214 at a relatively low power level, for example, about 10 watts of RF energy. Curve A is divided into three segments A1, A2, and A3. The broken line segment A2 represents a continuation of the exponential curve A3 when no cooling is applied. As can be seen by curve A, the temperature of the electrode-tissue interface without cooling reaches 80° C. and decreases exponentially as the distance into the tissue of the airway 100 increases. As shown, the curve A3 crosses the 50° C. tissue cell death boundary represented by the line 216 at a depth of about 5 millimeters. Thus, without electrode cooling, the depth of cell death that would occur would be approximately 5 millimeters as represented by the distance d1. Further cell death would stop at this power level.

If active cooling is employed, the temperature drops to a much lower level, for example, about 35° C. as represented by the curve A1 at the electrode-tissue interface at 0 millimeters in distance. Since this temperature is below 50° C., cell death will not begin to occur until a distance of d2 at the point where the curve A2 crosses the cell death line at 50° C., for example, a depth of 3 millimeters from the surface. Cell death will occur at depths from 3 millimeters to 5 millimeters as represented by the distance d3. Such a cooled ablation procedure is advantageous because it permits cell death and tissue destruction to occur at a distance (or a range of distances) from the electrode-tissue interface without destroying the epithelium and the tissue immediately underlying the same. In some embodiments, the nerve tissues running along the outside of the airway can be ablated without damaging the epithelium or underlying structures, such as the stroma and smooth muscle cells.

The curve B represents what occurs with and without cooling of the electrode at a higher power level, for example, 20 watts of RF energy. Segment B2 of curve B represents a continuation of the exponential curve of the segment B3 without cooling. As can be seen, the temperature at the electrode-tissue interface approaches 100° C. which may be undesirable because that is a temperature at which boiling of tissue fluid and coagulation and charring of tissue at the tissue-electrode interface will occur, thus making significantly increasing the tissue impedance and compromising the ability to deliver additional RF energy into the airway wall. By providing active cooling, the curve B1 shows that the temperature at the electrode-tissue interface drops to approximately 40° C. and that cell death occurs at depths of two millimeters as represented by d4 to a depth of approximately 8 millimeters where the curve B3 crosses the 50° C. tissue cell death boundary. Thus, it can be seen that it is possible to provide a much deeper and larger region of cell death using the higher power level without reaching an undesirable high temperature (e.g., a temperature that would result in coagulation and charring of tissue at the electrode-tissue interface). The systems can be used to achieve cell death below the epithelial surface of the airway so that the surface need not be destroyed, thus facilitating early recovery by the patient from a treatment.

The curve C represents a still higher power level, for example, 40 watts of RF energy. The curve C includes segments C1, C2, and C3. The broken line segment C2 is a continuation of the exponential curve C3. Segment C2 shows that the temperature at the electrode-tissue interface far exceeds 100° C. and would be unsuitable without active cooling. With active cooling, the temperature at the electrode-tissue interface approaches 80° C. and gradually increases and approaches 95° C. and then drops off exponentially to cross the 50° C. cell death line 216 at a distance of about 15 millimeters from the electrode-tissue interface at the epithelial surface of the airway represented by the distance d6. Because the starting temperature is above the 50° C. cell death line 216, tissue cell death will occur from the epithelial surface to a depth of about 15 millimeters to provide large and deep regions of tissue destruction.

FIG. 7 shows a cross-sectional temperature profile in a section of the airway wall through which the RF energy is delivered to ablate tissue. The terms "ablate" or "ablation," including derivatives thereof, include, without limitation, substantial altering of electrical properties, mechanical properties, chemical properties, or other properties of tissue. Ablation can involve destroying or permanently damaging, injuring, or traumatizing tissue. For example, ablation may include localized tissue destruction, cell lysis, cell size reduction, necrosis, or combinations thereof. In the context of pulmonary ablation applications, the term "ablation" includes sufficiently altering nerve tissue properties to substantially block transmission of electrical signals through the ablated nerve tissue.

Isothermal curves show the temperatures that are reached at the electrode assembly 214 and at different depths into the airway wall 100 from the electrode-tissue interface 215 when power is applied to the electrode assembly 214 and coolant (e.g., a room temperature saline solution or iced saline) is delivered to the balloon 212. The term "element" in the context of "expandable element" or "deployable element" includes a discrete element or a plurality of discrete elements. By way of example, an expandable element can be a single balloon or a plurality of balloons in fluid communication with one another.

By adjusting the rate of power delivery to the electrode assembly 214, the rate at which coolant is passed into the balloon 212, and the temperature of the coolant, and the size of the balloon 212, the isotherms can be modified. By selecting the proper temperature and flow rate of coolant and the rate of power delivery to the electrode assembly 214, it is possible to achieve temperatures in which isotherm A=60° C., B=55° C., C=50° C., D=45° C., E=40° C., and F=37° C. Further adjustments make it possible to achieve temperatures where isotherm A=50° C., B=47.5° C., C=45° C., D=42.5° C., E=40° C., and F=37° C. Only those areas contained within the 50° C. isotherm will be heated enough to induce cell death. In some procedures, tissue at a depth of about 2 mm to about 8 mm in the airway wall can be ablated while other non-targeted tissues at a depth less than 2 mm in the airway wall are kept at a temperature below at temperature that would cause cell death.

Figure 8:
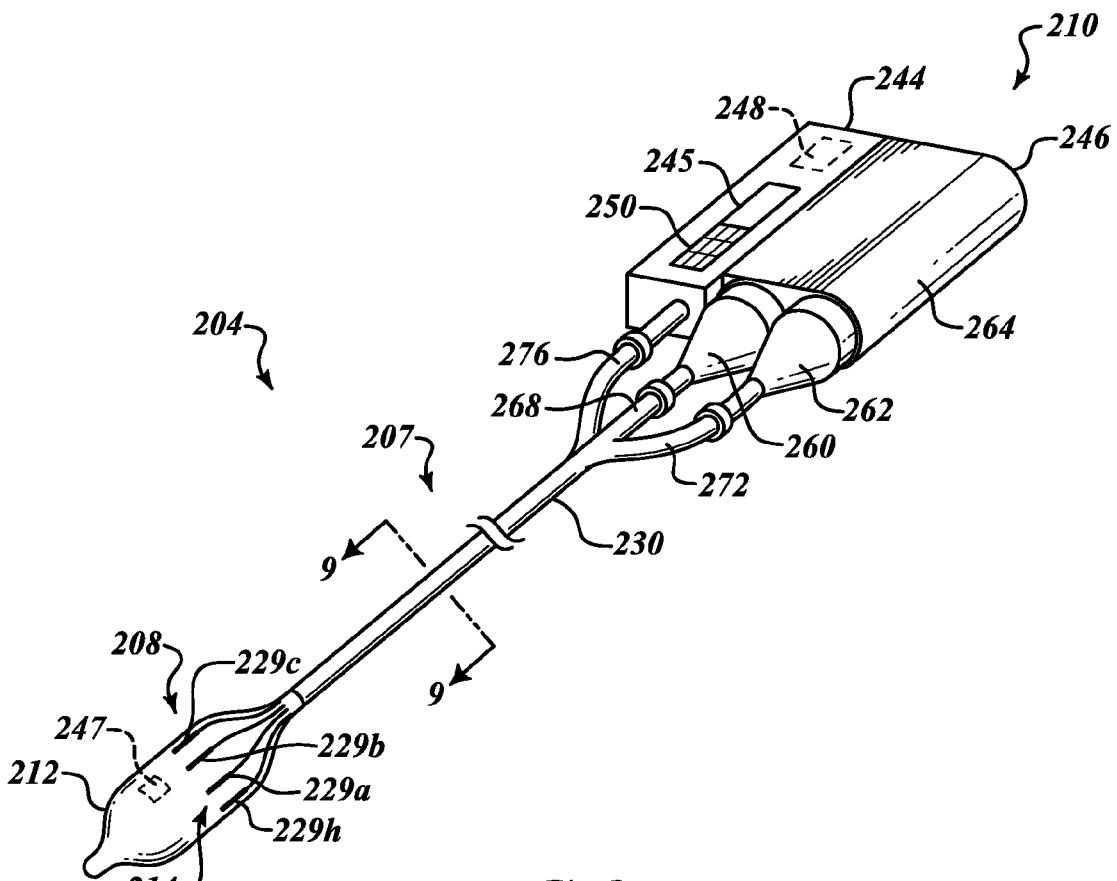
FIG. 8 is an isometric view of a delivery device with an ablation assembly.

With reference to FIG. 8, the catheter system 204 includes a control module 210 coupled to a catheter 207 having an elongate shaft 230. The balloon 212 can be inflated from a collapsed state to the illustrated expanded state. As the balloon 212 inflates, the electrode assembly 214 can be moved towards an airway wall. The inflated balloon 212 can help hold the electrode assembly 214 near (e.g., proximate to or in contact with) tissue through which energy is delivered. Coolant can absorb thermal energy to cool the balloon 212 or the electrode assembly 214, or both.

The control module 210 generally includes a controller 244 and a fluid delivery system 246. The controller 244 includes, without limitation, one or more processors, microprocessors, digital signal processors (DSPs), field programmable gate arrays (FPGA), and/or application-specific integrated circuits (ASICs), memory devices, buses, power sources, and the like. For example, the controller 244 can include a processor in communication with one or more memory devices. Buses can link an internal or external power supply to the processor. The memories may take a variety of forms, including, for example, one or more buffers, registers, random access memories (RAMs), and/or read only memories (ROMs). The controller 244 may also include a display 245, such as a screen, and an input device 250. The input device 250 can include a keyboard, touchpad, or the like and can be operated by a user to control the catheter 207.

The controller 244 can store different programs. A user can select a program that accounts for the characteristics of the tissue and desired target region. For example, an air-filled lung can have relatively high impedance, lymph nodes can have medium impedance, and blood vessels can have relatively low impedance. The controller 244 can determine an appropriate program based on the impedance. Performance can be optimized based on feedback from sensors that detect temperatures, tissue impedance, or the like. For example, the controller 244 can control operation of the ablation assembly 208 based on tissue temperatures. If the tissue surface temperature becomes excessively hot, cooling can be increased and/or electrode power decreased in order to produce deep lesions while protecting surface tissues.

An internal power supply 248 (illustrated in dashed line in FIG. 8) can be an energy generator, such as a radiofrequency (RF) electrical generator. RF energy can be outputted at a desired frequency. Example frequencies include, without limitation, frequencies in a range of about 50 KHZ to about 1,000 MHZ. When the RF energy is directed into tissue, the energy is converted within the tissue into heat causing the temperature of the tissue to be in the range of about 40° C. to about 99° C. The RF energy can be applied for about 1 second to about 120 seconds. In some embodiments, the RF generator 248 has a single channel and delivers approximately 1 to 25 watts of RF energy and possesses continuous flow capability. Other ranges of frequencies, time intervals, and power outputs can also be used. Alternatively, the internal power supply 248 can be an energy storage device, such as one or more batteries. Electrical energy can be delivered to the electrode assembly 214, which converts the electrical energy to RF energy or another suitable form of energy. Other forms of energy that may be delivered include microwave, ultrasound, direct current, or electromagnetic energy. Alternatively, cryogenic ablation may be utilized. Fluid at cryogenic temperatures can be delivered through the shaft 230 to cool a cryogenic heat exchanger on the ablation assembly 208.

The fluid delivery system 246 includes a fluid source 260 coupled to a supply line 268 and a fluid receptacle 262 coupled to a return line 272. The fluid source 260 can include a container (e.g., a bottle, a canister, a tank, or other type of vessel for holding fluid) held in a housing unit 264. In pressurizable embodiments, the fluid source 260 includes one or more pressurization devices (e.g., one or more pumps, compressors, or the like) that pressurize coolant. Temperature control devices (e.g., Peltier devices, heat exchangers, or the like) can cool or recondition the fluid. The fluid can be a coolant comprising saline, de-ionized water, refrigerant, cryogenic fluid, gas, or the like. In other embodiments, the fluid source 260 can be an insulated container that holds and delivers a chilled coolant to the supply line 268. The coolant flows distally through the elongate shaft 230 along a delivery lumen 326 and fills the ablation assembly 208. Coolant from the ablation assembly 208 flows proximally through the elongate shaft 230 via the return lumen 324 and ultimately flows into the receptacle 262.

A sensor 247 (illustrated in dashed line) is communicatively coupled to the controller 244. The controller 244 can command the catheter 207 based on signals from the sensor 247 (e.g., a pressure sensor, a temperature sensor, a thermocouple, a pressure sensor, a contact sensor, or the like). Sensors can also be positioned on the electrode assembly 214, along the elongate shaft 230, or at any other location. In a closed loop mode of operation, the electrical energy can be delivered to the electrode assembly 214 based upon feedback signals from the sensor 247, which can be configured to transmit (or send) one or more signals indicative of one or more tissue characteristics, energy distribution, tissue temperatures, or any other measurable parameters of interest. Based on those readings, the controller 244 adjusts operation of the electrode assembly 214. In an open loop mode of operation, operation of the electrode assembly 214 can be set by user input. For example, the user can observe tissue temperature or impedance readings and manually adjust the power level. Alternatively, the power can be set to a fixed power mode. In yet other embodiments, the catheter system 204 can switch between a closed loop mode of operation and an open loop mode of operation.

Figure 9:
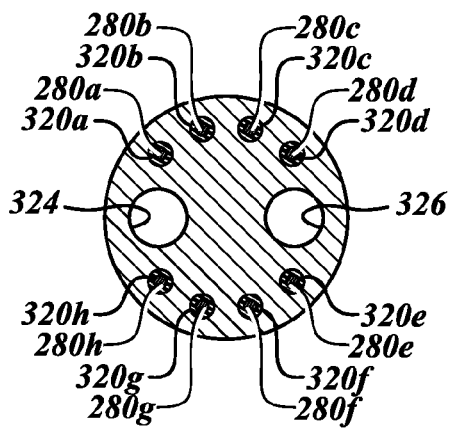
FIG. 9 is a cross-sectional view of an elongate shaft taken along a line 9-9 of FIG. 8.

Referring to FIGS. 8 and 9, the elongate shaft 230 includes a power line lumens 320*a-h*, the delivery lumen 326, and the return lumen 324. Power lines 280*a*-280*h* (collectively "280") extend through the power line lumens 320*a*-320*h* (collectively "320"), respectively, and couple the controller 244 to the electrode assembly 214. The elongate shaft 230 can be made, in whole or in part, of one or more metals, alloys (e.g., steel alloys such as stainless steel), plastics, polymers, and combinations thereof, as well as other biocompatible materials, and can be flexible to pass conveniently along highly branched airways.

Figure 10:
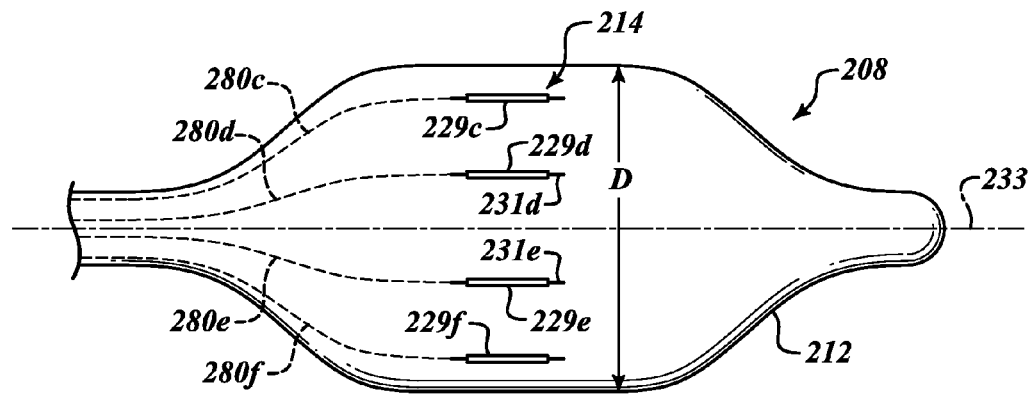
FIG. 10 is a side elevational view of an ablation assembly.
Figure 11:
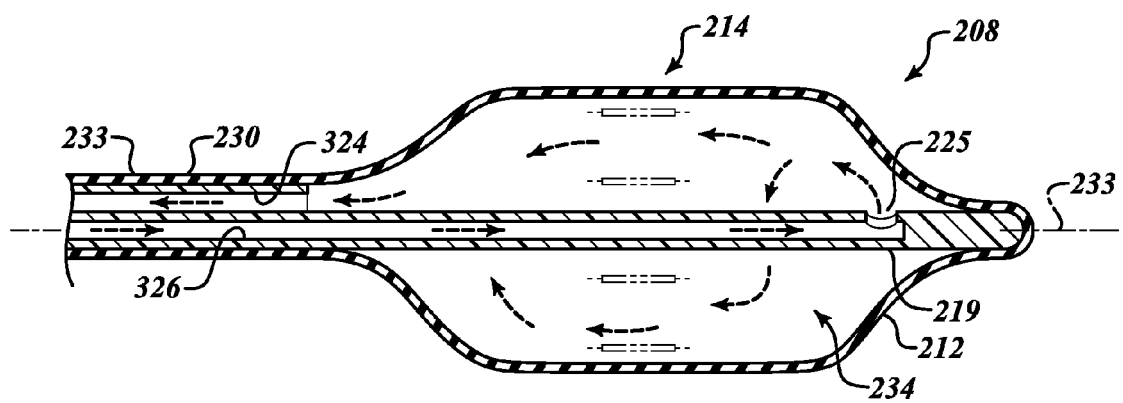
FIG. 11 is a longitudinal cross-sectional view of the ablation assembly of FIG. 10.

Referring to FIGS. 10 and 11, power lines 280 deliver energy from the power supply 248 to the electrode assembly 214. In some embodiments, the power lines 280 pass through the chamber 234 and the outer wall of the balloon 212. In other embodiments, connectors for the electrode assembly 214 are positioned within the chamber 234. The power lines

280 can extend between the connectors and the elongated shaft 230 to avoid exposure to bodily fluid.

The electrode assembly 214 can include, without limitation, monopolar electrodes, bipolar electrodes, metal electrodes, wire electrodes, needle electrodes, or the like and can form an array of circumferential lesions, each extending along only a portion of a circumference of a vessel or body structure. If the body structure is an airway, each of the lesions can at least partially surround a lumen of the airway. The lesions can have an arc length of less than 360 degrees (e.g., about 25 degrees to about 45 degrees). In some embodiments, the lesions are spaced apart with respect to a longitudinal axis of the body structure. Together, the lesions cover the desired circumference. For example, the lesion can overlap circumferentially (e.g., when viewed along an axial length of the body structure) with the beginning of the next lesion while being longitudinally spaced apart from one another, thereby ensuring the entire circumference of the airway (or portion thereof) has been treated.

The electrode assembly 214 includes electrodes 229 circumferentially spaced apart about the balloon 212. Each electrode 229 has a pair of exposed electrode elements. An electrode element 231d of electrode 229d and an element 231e of an adjacent electrode 229e can cooperate to form an RF arc that ablates radially adjacent tissue. The electrodes 229 can be coupled to an exterior surface of the balloon 212. In other embodiments, the electrodes 229 can be embedded in the sidewall of the balloon 212 or otherwise fixed to the balloon 212.

Adjacent electrodes 229 may be operated in a bipolar manner, wherein one electrode is positive and the other electrode is negative, such that RF power is transmitted through the tissue. If the electrodes 229 are monopolar electrodes, the electrodes can be coupled to separate power lines 280 to allow for independent control of each electrode. Alternatively, the electrodes 229 may be coupled to the same power line so as to be operated together.

The balloon 212 can be made, in whole or in part, of polymers, plastics, silicon, rubber, polyethylene, polyvinyl chloride, chemically inert materials, non-toxic materials, electrically insulating materials, combinations thereof, or the like. To enhance heat transfer, the balloon sidewall can comprise one or more conductive materials with a high thermal conductivity. For example, conductive strips (e.g., metal strips) can help conduct thermal energy away from hot spots, if any. The balloon 212 can conform to irregularities on the airway surface (e.g., cartilaginous rings, side branches, etc.) and can be made, in whole or in part, of a distensible material, such as polyurethane (e.g., low durometer polyurethane) or other type of highly conformable material that may be transparent, semi-transparent, or opaque. The balloon 212 can have different inflated shapes, including a hot dog shape, an ovoid shape, a cylindrical shape, or the like. To treat a bronchial tree of a human, the diameter D of the inflated balloon 212 can be in a range of about 12 mm to about 18 mm. For enhanced treatment flexibility, the inflated balloon diameter may be in a range of about 5 mm to about 25 mm. The balloon 212 can be sized to treat other organs or tissue of other animals. To inflate the balloon 212, fluid is delivered along the delivery lumen 326 and through an inlet port 225, as shown in FIG. 11. The coolant circulates within the chamber 234 and then flows proximally along the return lumen 324.

Figure 12:
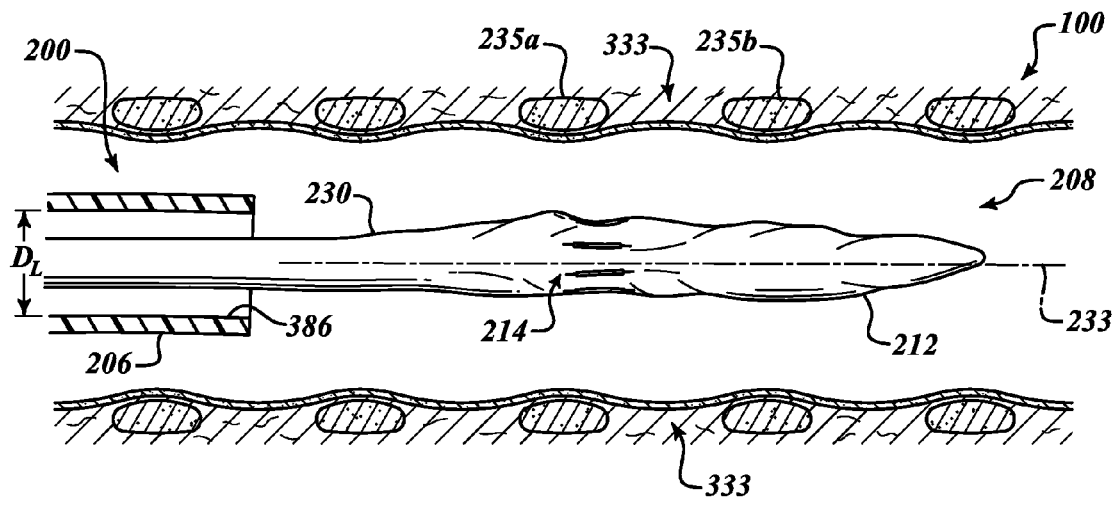
FIG. 12 is a partial cross-sectional view of a treatment system with a delivery device extending out of an access apparatus.
Figure 13:
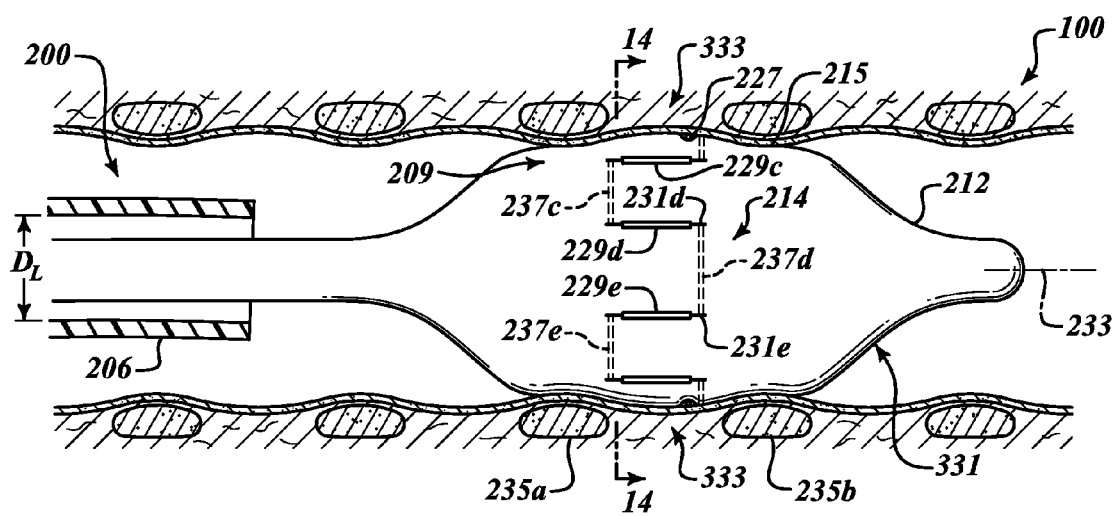
FIG. 13 is a side elevational view of an ablation assembly.

FIGS. 12 and 13 show one exemplary method of using the treatment system 200. The airway 100 can be viewed to locate and evaluate the treatment site(s) and non-targeted tissues before, during, and/or after performing a therapy. The access apparatus 206 can be a guide tube, a delivery sheath, a bronchoscope, or an endoscope and can include one or more viewing devices, such as optical viewing devices (e.g., cameras), optical trains (e.g., a set of lens), and the like. Different regions about the circumference the airway can be stimulated (e.g., electrically stimulated) to locate the position of the airway nerve trunk(s) or conditions. Detection of bronchoconstriction may be accomplished by measuring airway smooth muscle contraction distal to the point along the airway length that stimulation is performed. Muscle contraction can be measured by monitoring changes in the pressure of an inflated balloon or other type of sensor that is proximate to or in contact with the airway. This technique can minimize or limit the circumferential area of the airway that is treated to reduce or eliminate the risk of airway stenosis. The nerve locations can be determined by measuring nerve electrical signals at points along the airway circumference to locate the position of the airway nerves. An airway nerve signal stimulant, such as cold air, histamine or phenyl diguanide may be used to increase the nerve signal amplitude to facilitate airway nerve signal localization around the airway circumference.

When the access apparatus 206 of FIG. 12 is moved along a body lumen, the collapsed ablation assembly 208 is held within a working channel 386. The ablation assembly 208 is moved distally out of the working lumen 386 and is inflated to move the electrode assembly 214 near (e.g., proximate to or in contact with) the airway wall. RF energy can travel through tissue to heat tissue (e.g., superficial and deep tissue) to form lesions at targeted regions. The targeted regions and associated lesion generally correspond to the dashed lines in FIGS. 13 and 14.

The term "lesion" as used herein refers to tissue which is permanently damaged, i.e. to the point of cell death. In some cases, the delivery of energy will cause temporary or non-lethal damage to cells outside the region referred to as the "lesion." For example, epithelial or smooth muscle cells may be temporarily damaged or altered by the energy delivery described herein. However, advantageously, through the use of differential cooling, these cells can recover and remain functional and, thus, are not considered part of the "lesion." By contrast, the ablation assembly 208 can permanently damage to nerve tissues or other targeted tissue lying deep in the airway wall or on the outside of the airway wall, thus attenuating nerve signals that are the cause of certain pulmonary conditions.

The cooling section 209 of FIG. 13 contacts the airway wall 100 so as to cool tissue while energy is outputted by the electrode assembly 214. The net effect of this superficial and deep heating by RF energy and superficial cooling by the circulating coolant is the concentration of heat in the outer layers of the airway wall 100. The temperature of the connective tissue can be higher than the temperatures of the epithelium, stroma, and/or smooth muscle. By example, the temperature of the connective tissue can be sufficiently high to cause damage to the nerve trunk tissue or other deep tissue while other non-targeted tissues of the airway are kept at a lower temperature to prevent or limit damage to the non-targeted tissues.

Figure 14:
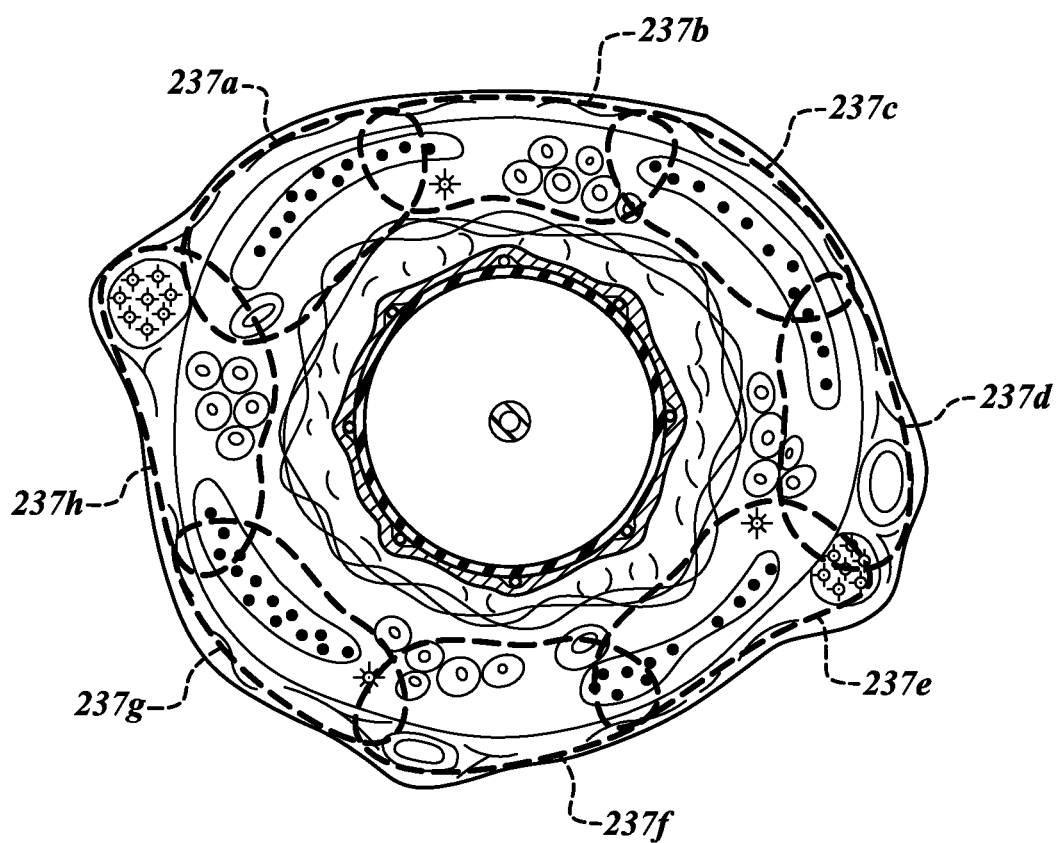
FIG. 14 is a cross-sectional view of an airway surrounding a deployed ablation assembly, taken along a line 14-14 of FIG. 13.

FIGS. 13 and 14 show eight separate lesions 237a-h (collectively "237"). Adjacent lesions 237 are axially offset from one another along a longitudinal axis 233 of the ablation assembly 208. Each lesion 237 can have an arc length of about 45 degrees such that the array of lesions extends about substantially the entire circumference of the airway wall 100, as shown in FIG. 14. The length of the exposed electrode elements corresponds to the widths of the lesions 237. The lengths of exposed electrode elements (e.g., the length of electrode elements 231d, 231e) can be selected based on the desired width of the lesions 237. Advantageously, the lesions 237 can be formed simultaneously. For example, all or a substantial portion of the lesions 237 can be formed at the same time to avoid having to move the ablation assembly between ablation treatments. In other embodiments, different electrodes 229 can be activated to sequentially form lesions. The electrode assembly 214 can be moved to different locations to ablate different tissue. As such, one or more lesions can be performed simultaneously or sequentially based on the desired treatment.

With conventional ablation catheters, the ablating process may be sufficient to cause scarring which may cause local airway narrowing or stenosis. Because lesions 237 are at different locations along the length of the airway, the effects of stenosis can be mitigated. The illustrated embodiment is well suited to denervate the airway while avoiding the formation of a continuous ring of scar tissue. A continuous ring of scar tissue extending 360 degrees about the inner circumference of the airway 100 may significantly decrease the cross-sectional area of the airway lumen, thereby significantly increasing airflow resistance. The staggered lesions 237 help mitigate the reduction of the cross-sectional area of the airway lumen.

FIG. 14 shows the location of the lesions 237. A projection of the outer profiles of the lesions 237 along a long axis of the airway 100 and onto an imaginary plane perpendicular to the long axis can define a substantially continuous closed ring, as shown in FIG. 14. Because nerve trunks 45 extend longitudinally along the airway 100, the lesions 237 can be at a depth sufficient to ensure that all of the nerve trunks are ablated. In other embodiments, the electrode assembly 214 can be used to treat only a portion of the airway circumference, e.g. 180 degrees, 150 degrees, or 130 degrees of the airway circumference. That may be all that is required to effectively denervate the airway 100. Accordingly, nervous signals can be effectively cut off without forming a lesion that extends about the entire airway wall and can further reduce the formation of stenosis.

During RF ablation, heat can be concentrated in one or more of the internal layers (e.g., the stroma) of the airway wall or in the inner lining (e.g., the epithelium) of the airway wall. Furthermore, one or more of the vessels of the bronchial artery branches may be within the lesion. The heat generated using the electrode 214 can be controlled such that blood flowing through the bronchial artery branches protects those branches from thermal injury while nerve trunk tissue is damaged, even if the nerve tissue is next to the artery branches. The catheter 207 can produce relatively small regions of cell death. For example, a 2 mm to 3 mm section of tissue in the middle of the airway wall 100 or along the outer surface of the airway wall 100 can be destroyed. By the appropriate application of power and the appropriate cooling, lesions can be created at any desired depth.

Airway cartilage rings or cartilage layers typically have a significantly larger electrical resistance than airway soft tissue (e.g., smooth muscle or connective tissue). Airway cartilage impedes energy flow (e.g., electrical radiofrequency current flow) and makes the formation of therapeutic lesions with radiofrequency electrical energy to affect airway nerve trunk(s) challenging when the electrode is next to cartilage.

The illustrated energy emitter 214 can function as an intercartilaginous energy emitter. The electrode elements 227 may be dimensioned to generally coincide with the spacing of the cartilaginous rings 235a, 235b (collectively "235"). As shown in FIG. 13, each electrode element 227 is disposed between two adjacent rings 235a, 235b such that the lesions 237 are positioned entirely within the space 333 between the cartilage rings 235.

The electrodes 229 can serve as intercartilaginous positioners that help preferentially seat the electrode elements 227 in the space 333, thus making it easy to perform the treatment or to verify correct positioning. For example, the electrode elements 227 can protrude outwardly and tend to move into and fit into the regions of softer, more compliant tissue in the space 333. The electrodes 229 can thus be used to index the ablation assembly 208.

Figure 15:
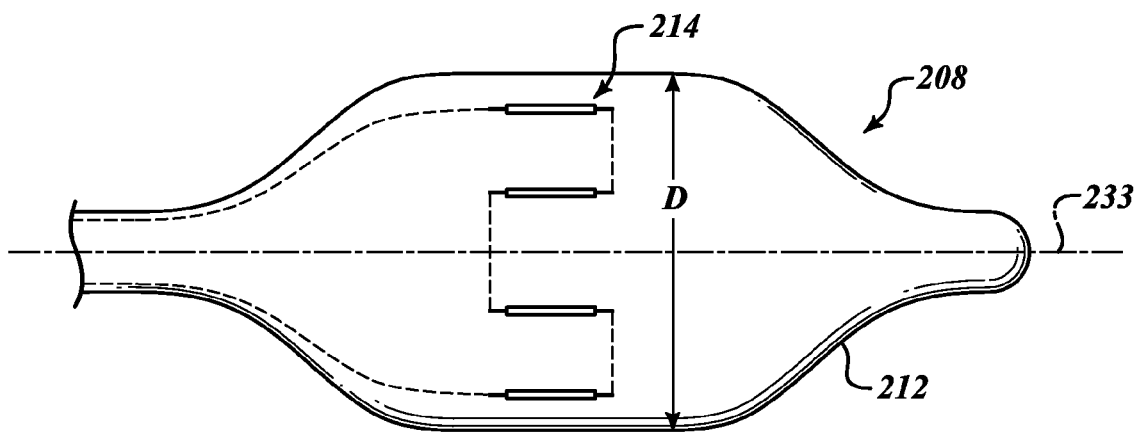
FIG. 15 is a side elevational view of an ablation assembly.

FIG. 15 shows electrodes that are monopolar electrodes connected by a single power line. Power can be simultaneously delivered to the electrodes. Any number of electrodes can be positioned along the balloon 212. For example, one or more of the electrodes can be evenly or unevenly spaced about the circumference of the balloon.

Figure 16:
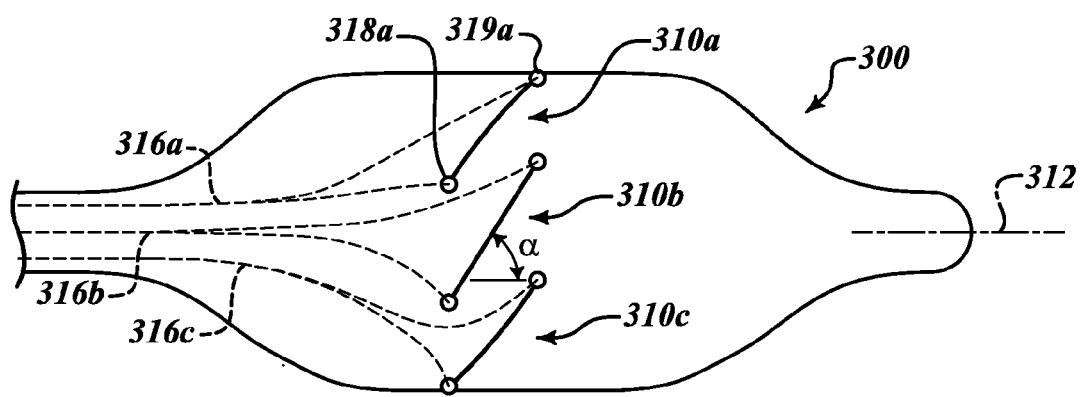
FIG. 16 is a side elevational view of an ablation assembly for producing oblique lesions.

FIG. 16 shows electrodes 310a-310c (collectively "310") oriented at an oblique angle relatively to a longitudinal axis 312 of an ablation assembly 300. Power lines 316a-316c (collectively "316") provide energy to the respective electrodes 310. (Although not illustrated, other electrodes are located on the non-visible backside of the ablation assembly 300.) The electrodes 310 can be bipolar electrodes. By way of example, the electrode 310a can include electrode elements 318a, 319a, which can be alternatively positive and negative to transmit RF energy between the elements 318a, 319a.

The angle α between the electrodes 310 and the direction of the longitudinal axis 312 can be selected based on the length of the lesions to be formed, desired circumferential gap between adjacent lesions, and the like. The illustrated angle α is about 45 degrees. Other angles are also possible, if needed or desired. Between adjacent electrodes 310, there can be regions of non-treated, undamaged tissue.

As shown in FIG. 16, one lesion created by an electrode or electrode pair 310a overlaps in a circumferential direction with the beginning of the next lesion created by the circumferentially adjacent electrode or electrode pair 310b to ensure that an entire circumference (or portion thereof) of a tubular body structure is treated. If an imaginary line is drawn in the longitudinal direction through one end of the lesion made by electrode 310a, the imaginary line intersects or is proximate to the near end of the adjacent lesion made by the electrode 310b. Thus, ends of adjacent lesions are axially offset along the axis 312 and overlapping in the circumferential direction.

Figure 17:
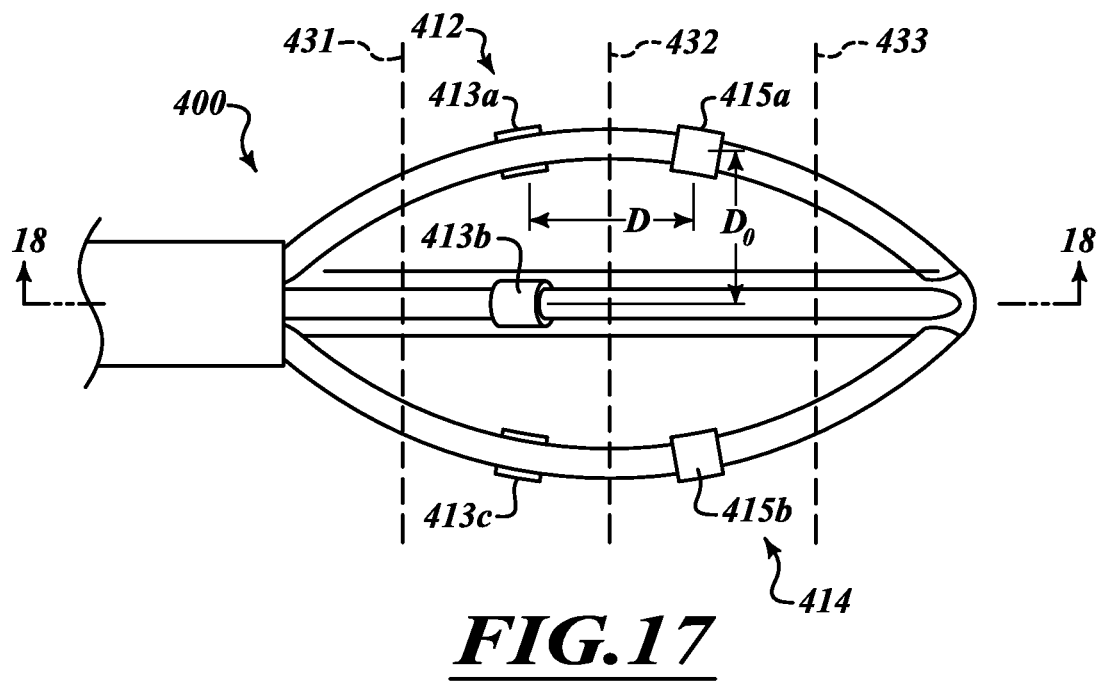
FIG. 17 is a side elevational view of an ablation assembly with internal passageways.

FIG. 17 shows an ablation assembly 400 that includes an expandable basket 414 and electrodes 413, 415. The basket 414 includes hollow members through which coolant flows to cool the electrodes 413, 415. A longitudinal length of the basket 414 can be selected such that the basket 414 extends across multiple cartilaginous rings. The electrodes 413, 415 can be positioned between the rings. For example, the elongate basket 414 can extend across at least three cartilaginous rings (represented by vertical dashed lines 431, 432, 433 in FIG. 17). The electrodes 413 are positioned between cartilaginous rings 431, 432. The electrodes 415 are positioned between cartilaginous rings 432, 433. When the basket 414 is deployed, the distance D between adjacent rows of electrodes 413, 415 can generally correspond to the distance between the cartilaginous rings, thereby ensuring that the electrodes 413, 415 can be seated between the cartilaginous rings. The electrode 413a can have a first polarity and the electrode 413b can have an opposite polarity such that energy flows between the electrodes. The electrode pair 413a, 413b is angularly offset from the adjacent pair of electrodes 415a, 415b to form circumferentially overlapping and axially spaced apart lesions.

The distance of overlap D can be sufficient to ensure that the entire circumference of the airway is treated.

Figure 18:
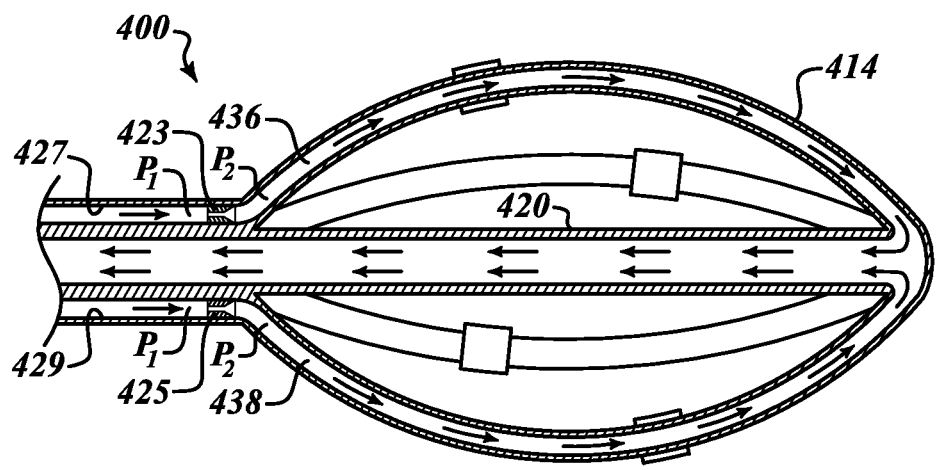
FIG. 18 is a cross-sectional view of the ablation assembly of FIG. 17 taken along a line 18-18.

FIG. 18 shows fluid flowing along lumens 427, 429 and through pressure reducing elements 423, 425, respectively. As used herein, the term "pressure reducing element" refers, without limitation, to a device configured to reduce the pressure of a working fluid. The pressure reducing element can reduce the pressure of the working fluid to a pressure equal to or less than a vaporization pressure of the working fluid. The working fluid can comprise a refrigerant (e.g., a cryogenic refrigerant or a non-cryogenic refrigerant). In some embodiments, the pressure reducing elements are in the form of pressure reduction or expansion valves that cause vaporization of at least a portion of the working fluid passing therethrough. The pressure reducing element vaporizes an effective amount of the working fluid (e.g., a refrigerant, cryogenic fluid, etc.) to reduce the temperature of the working fluid. In some modes, substantially all or most of the working fluid by weight passing through the elements 423, 425 is converted to a low temperature, low pressure gas. In some embodiments, the pressure reducing elements 423, 425 can be a nozzle valve, a needle valve, a Joule-Thomson throttle, a throttle element, or any other suitable valve for providing a desired pressure drop. For example, a Joule-Thomson throttle can recover work energy from the expansion of the fluid resulting in a lower downstream temperature. In some embodiments, the pressure reducing elements can be substituted with flow regulating elements (e.g., a valve system), especially if the working fluid is a non-refrigerant, such as water.

With reference to FIG. 18, high pressure gas $P_1$ of FIG. 18 passes through the delivery lumens 427, 429. The high pressure gas $P_1$ passes through the elements 423, 425 and enters the channels 436, 438 where the pressure drops to $P_2$. The drop in pressure from $P_1$ to $P_2$ leads to a drop in temperature of the gas from $T_1$ to $T_2$. The magnitude of the temperature change is given by:

$$T_1 - T_2 = \mu(P_1 - P_2)$$

where
T is the temperature of the gas;
P is the pressure of the gas;
$\mu$ is the Joule-Thomson coefficient of the gas;
Subscript 1 denotes a high pressure condition; and
Subscript 2 denotes a low pressure condition.

A second pressure drop can occur when the gas in the channels 436, 438 exits through the vents and drops to a surround pressure, as discussed in connection with FIGS. 19 and 20. If the ablation assembly 400 is used in the respiratory system, the surrounding pressure is atmospheric pressure. This temperature drop is:

$$T_2 - T_3 = \mu(P_2 - P_{ATM})$$

The Joule-Thomson coefficient ($\mu$) is specific for each gas or gas mixtures. Standard temperature values for $\mu$ are:
Carbon Dioxide $$\mu_{CO_2} = 1.16 \times 10^{-5} \frac{K}{Pa}$$

Air $$\mu_{air} = 0.23 \times 10^{-5} \frac{K}{Pa}.$$

These coefficients indicate that for a given pressure drop, $CO_2$ will cause a 5 times greater drop in temperature than a similar drop in pressure experienced by air.

The use of air in the lungs can be desirable. Carbon dioxide can be used if the flow rates of coolant gas are sufficiently low so as to not overwhelm the subject's ability to ventilate this additional carbon dioxide out of the lungs. The cooling effect can be enhanced if the coolant in the coolant conduit is a high pressure liquid, such as liquid air or liquid $CO_2$. The high pressure liquid passes through the pressure reducing elements (e.g., a throttle) and undergoes an endothermal phase change from a high pressure liquid to a high pressure gas, which causes the temperature of the gas to be lower than that of the high pressure liquid. It then goes through a Joule-Thomson expansion from $P_1$ to $P_2$ which causes a further drop in temperature, before being vented out via vents 441, as discussed in connection with FIGS. 19 and 20.

Figure 19:
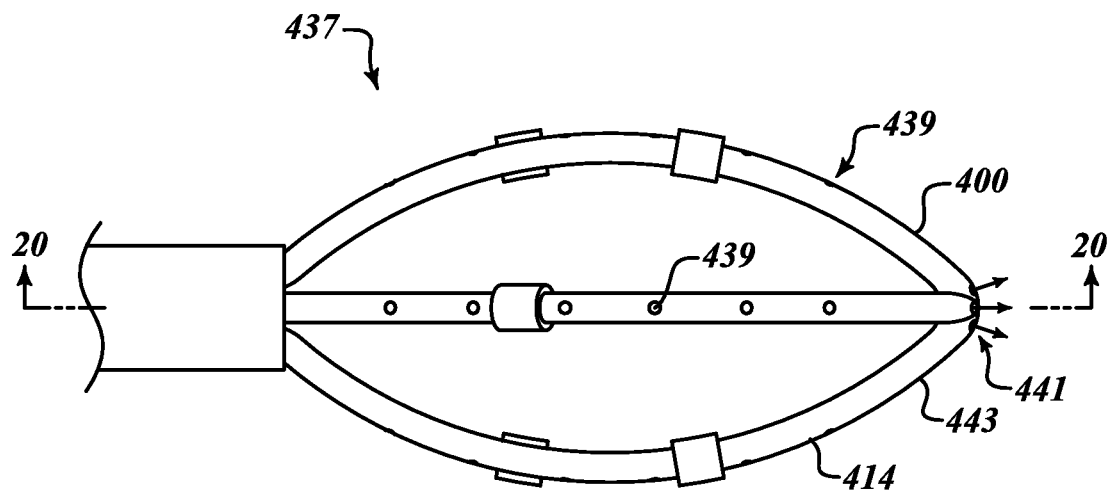
FIG. 19 is a side elevational view of an ablation assembly with vents.
Figure 20:
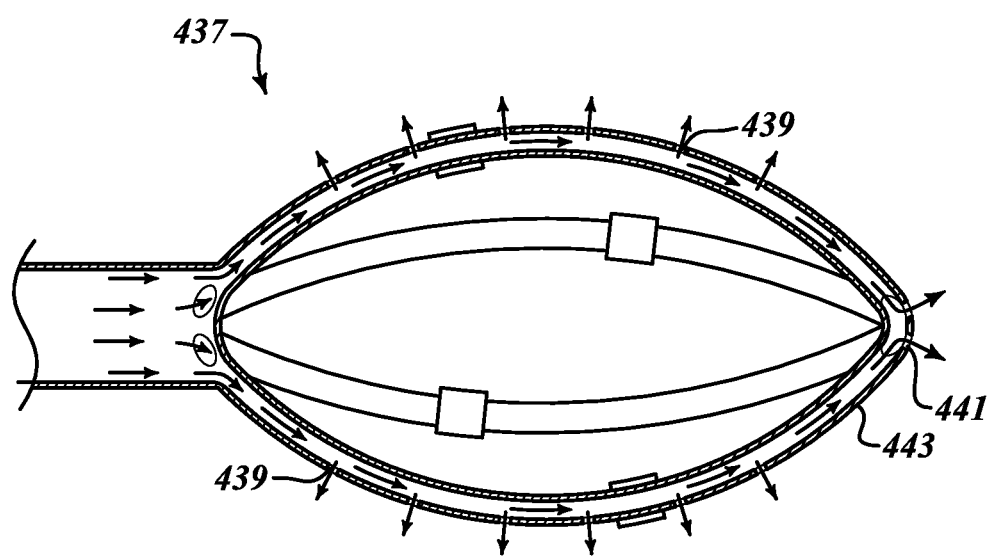
FIG. 20 is a cross-sectional view of the ablation assembly of FIG. 19 taken along a line 20-20.

FIGS. 19 and 20 show an ablation assembly 437 that is generally similar to the ablation assembly 400 of FIGS. 17 and 18, except as detailed below. The ablation assembly 437 includes an array of openings or vents 439 positioned along the elongate members. Coolant flowing through the elongate members can escape out of the openings 439 to cool adjacent tissue. Additionally, openings or vents 441 positioned at the distal end 443 can discharge coolant. As shown in FIG. 20, coolant, represented by arrows, can escape out of the vents 439, 441. In this manner, coolant can cool the ablation assembly 437 and can provide direct tissue cooling. Vents 441 may optionally be configured to provide a suitable pressure drop to vaporize the coolant from Joule-Thomson expansion, as described above, thus lowering the coolant temperature.

Figure 21:
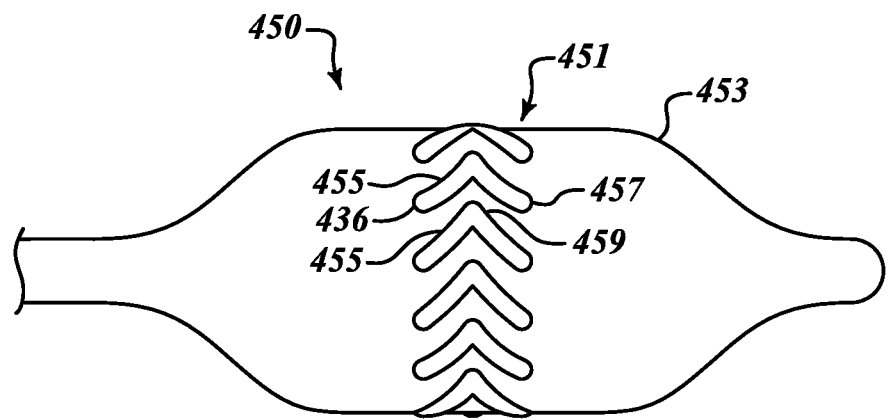
FIG. 21 is a side elevational view of an ablation assembly with an array of V-shaped electrodes.

FIG. 21 shows an ablation assembly 450 that has V-shaped electrodes circumferentially spaced apart along an expandable member 453. An electrode 455 has ends 456, 457 that overlap with a tip 459 of the adjacent electrode 455. The electrodes can output energy to V-shaped target regions, which are likewise spaced apart along the airway circumference to form V-shaped lesions. Untreated tissue between the V-shaped lesions can help ensure that the lumen airway does not significantly narrow due to scar tissue or stenosis.

Figure 22:
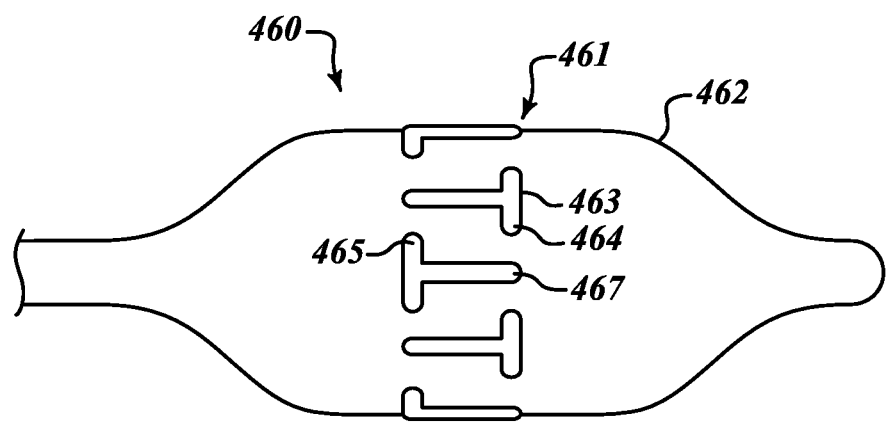
FIG. 22 is a side elevational view of an ablation assembly with T-shaped electrodes.

FIG. 22 illustrates an ablation assembly 460 including an expandable element 462 carrying T-shaped electrodes. The electrode 463 has a free end 464 that overlaps with an end 465 of an adjacent electrode 467. The circumferentially aligned electrodes 461 can form a plurality of generally T-shaped lesions. In other embodiments, the electrodes can be U-shaped, S-shaped, W-shaped, L-shaped, or any other suitable shape. In addition, in any of these embodiments, the electrodes may be longitudinally displaced in a diagonal or helical pattern similar to that shown in FIG. 16.

Figure 23:
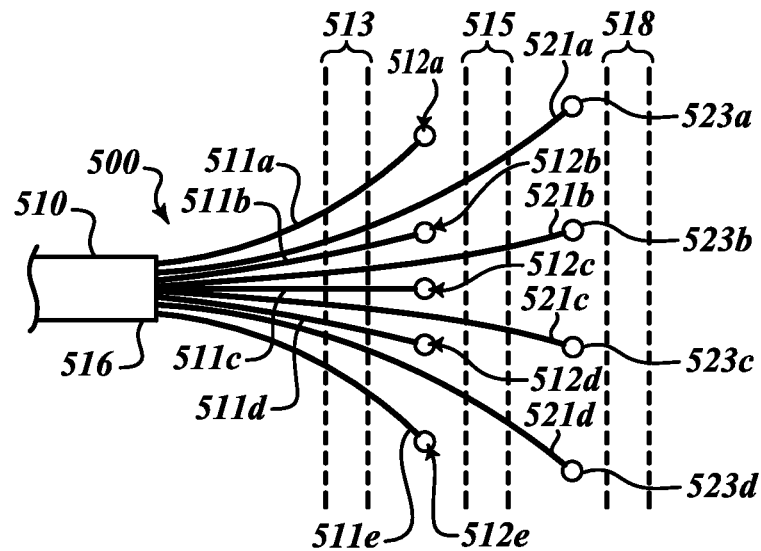
FIG. 23 is a side elevational view of a multi-tine ablation assembly.

FIG. 23 shows an ablation assembly 500, including a first set of elongate members 511a-511d (collectively "511") that can position electrodes 512 between cartilaginous rings 513, 515 (illustrated in dashed lines). Elongate members 521a-521d (collectively "521") carry electrodes 523a, 523b, 523c, 523d (collectively "523") positioned between the cartilaginous rings 515, 518. The electrodes 512 form lesions between the rings 513, 515. The electrodes 523 form lesions between the rings 515, 518. The elongate members 511, 521 may be flexible and resilient rods or wires biased radially outwardly to position the electrodes against the airway wall and configured to position electrodes 523 in circumferentially offset positions relative to the electrodes 512 so that different circumferential regions of an airway wall are treated with each electrode pair. One end of a lesion in one inter-collagenous space can overlap circumferentially with an adjacent lesion in an adjacent inter-collagenous space. The lesions can thus be axially spaced apart from one another but circumferentially overlapping with respect to the body lumen. The elongate members 511, 521 may be retracted into a tubular sheath 510 to collapse them into a radially contracted configuration suitable for introduction into the airway.

Figure 24:
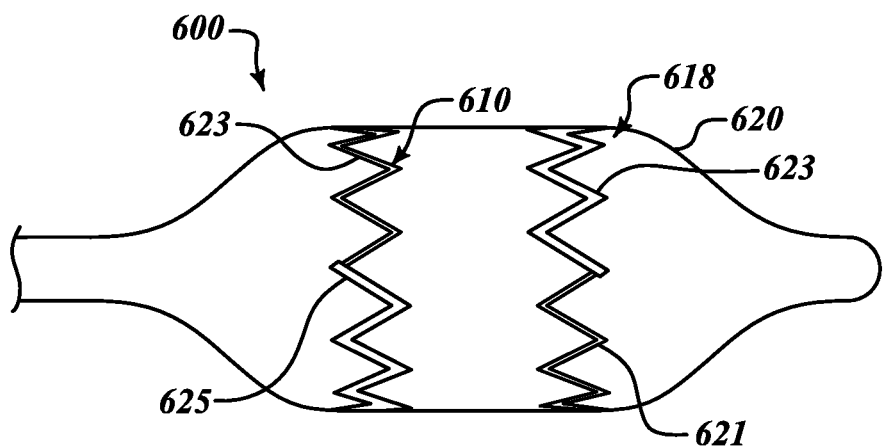
FIG. 24 is a side elevational view of an ablation assembly with a pair of electrode assemblies.

FIG. 24 shows an ablation assembly 600 with an expandable energy emitter assembly 610. An expandable electrode assembly 623 can encircle all or a major part of an expandable member 620, illustrated as a balloon. An insulator 625 extends between the ends over a portion of the electrode assembly 623. The electrode 623 can have a zigzag configuration (illustrated), serpentine configuration, or wavy configuration to allow expansion and can extend about 90 degrees to about 360 degrees around the balloon 620. During use, the exposed electrode 623 can face a region of an airway to be treated, e.g., the posterior side where the nerve trunks are often located. Alternatively, the emitter assembly 610 can include a plurality of exposed electrodes separated by insulated portions to create discrete lesions.

Optionally, a second energy emitter 618 is positioned distally of the energy emitter 610. The energy emitter 618 has an exposed electrode 621 and an insulator 623. The electrode 621 can cooperate with the electrode 623 to form circumferentially offset and axially spaced-apart complementary (e.g., overlapping) lesions. For example, the electrode 623 can form a lesion having an arc length of about 180 degrees along an upper portion of an airway wall. The electrode 621 can form a lesion having an arc length of about 180 degrees along a lower portion of an airway wall. Together, the two lesions extend about the entire circumference of the airway wall. The lesions can be created simultaneously or sequentially.

Figure 25:
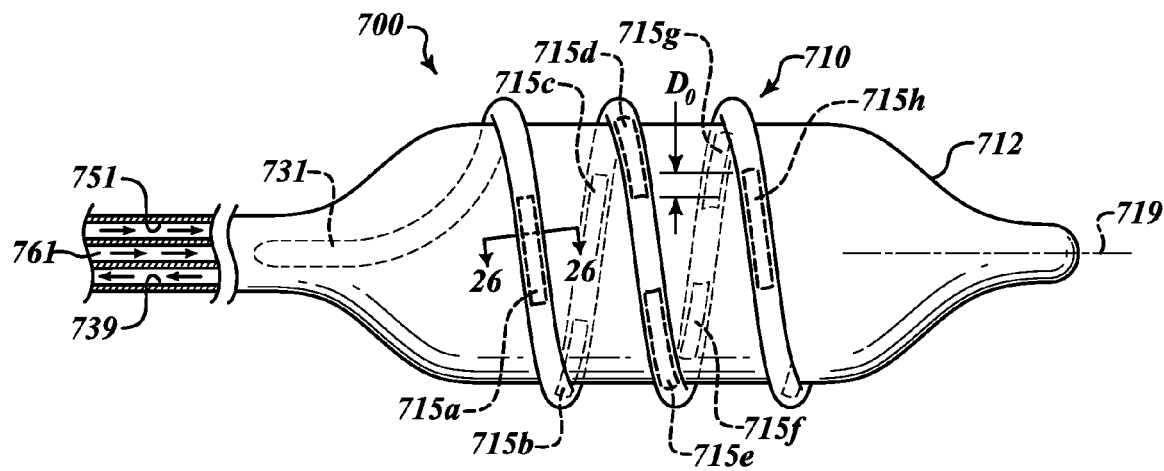
FIG. 25 is a side elevational view of an ablation assembly with a coolable electrode assembly.

FIG. 25 shows an ablation assembly 700 that includes an energy emitter in the form of an electrode assembly 710 wrapped about an expandable element 712. The electrode assembly 710 includes a conduit 731 and a plurality of electrodes 715a-h (collectively "715"). The electrodes 715 can simultaneously or sequentially form lesions.

Figure 26:
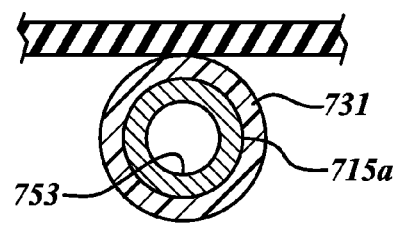
FIG. 26 is a cross-sectional view of the electrode assembly taken along a line 26-26 of FIG. 25.

Referring to FIG. 26, the electrode 715a can be a hollow tubular metallic member which, when the balloon 712 is inflated, is oriented in the general circumferential direction. The conduit 731 delivers coolant (saline or other coolant) serially through the electrodes 716.

Different coolants can be delivered through the balloon 712 and the conduit 731. Coolant can flow through a delivery lumen 761 through the conduit 731 to cool the electrodes 715. Another coolant can flow through a delivery lumen 751 and into the balloon 712. Coolant in the balloon 712 and the conduit 731 can flow proximally via a return lumen 739. In other embodiments, coolant flows serially through the electrode assembly 710 and the balloon 712.

Separate wire pairs can be electrically coupled to each electrode 715. Each electrode 715 can be operated independently. In other embodiments, the electrodes 715 are bipolar and arranged in pairs of opposite polarity. As discussed with respect to previous embodiments, the electrodes 715 can be oriented and positioned with respect to one another to form lesions within inter-collagenous spaces. U.S. patent application Ser. No. 12/463,304, filed May 8, 2009, and U.S. patent application Ser. No. 12/913,702 filed, Oct. 27, 2010, are incorporated by reference in their entireties and disclose techniques, materials, catheters, and components that can be used with the ablation assembly 700.

Electrodes 715a-h are arranged along the helical conduit 731 such that they create lesions which are circumferentially offset from one another, albeit with some overlap, and which are axially offset from one another. An imaginary line drawn in the axial direction (parallel to axis 719) through each of electrodes 715a-h will intersect another of electrodes 715a-h to ensure that the entire circumference of the airway is treated. Advantageously, the electrodes are spaced apart along the helical conduit 731 such that the lesions they create are longitudinally separated along the airway, thus reducing the chance that stenosis will result.

Lesion shapes can be controlled by adjusting the temperature of the coolant, coolant flow rates, heat carrying capacity of coolants, thermal characteristics of the balloon (e.g., the heat transfer properties of the balloon), or the amount of delivered power. FIGS. 27A-31B show temperature profiles and corresponding lesions formed by progressively increased cooling by a balloon. The cooling capacity of the balloon can be increased by decreasing the coolant temperature or by increasing the coolant flow rate, or both. Lesion shaping can also be achieved by holding the cooling capacity of the balloon generally constant while varying the coolant capacity of the electrode or by increasing or decreasing the power delivered to the tissue. By way of example, the ablation assembly 700 in FIG. 25 can be used to form the lesions of FIGS. 27B, 27C, 28B, 29B, 30B, and 31B. Because the balloon 712 has a larger diameter than an electrode channel 753, there is a relatively low flow velocity along the balloon surface as compared to the high velocity flow through the electrode 715a. This results in differential cooling. If the electrode 715a and the balloon 712 have independent flows, the coolants can be at different temperatures and/or flow velocities for differential cooling.

Figure 27A:
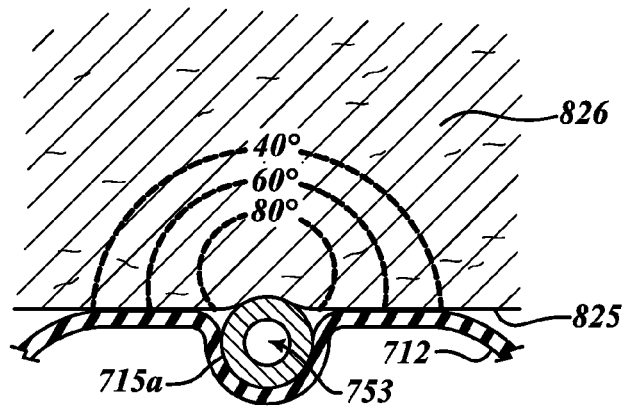
FIGS. 27A-31B show isotherms and corresponding lesions.
Figure 27B:
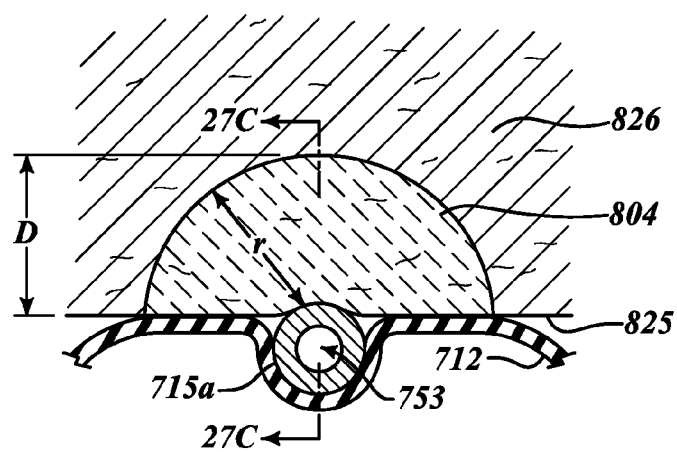
Figure 27C:
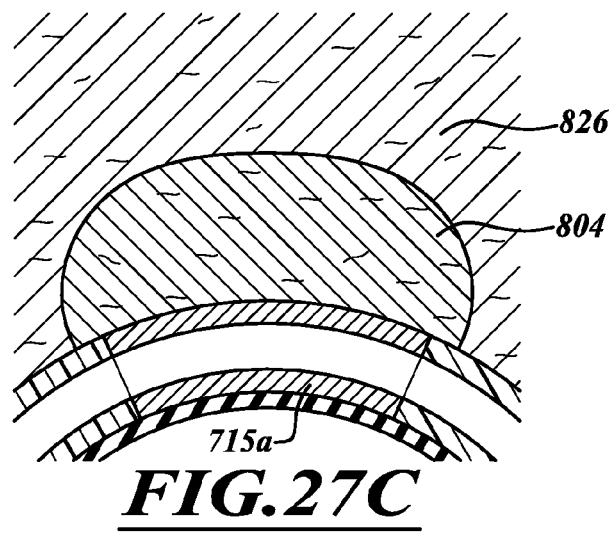

FIG. 27A shows isotherms 80° C., 60° C., and 40° C. and temperature distributions in tissue. FIG. 27B shows a lesion 804 corresponding to the isotherms of FIG. 27A. The coolant in a cooling channel 753 is the only coolant that absorbs a significant amount of heat. The balloon 712 does not absorb a significant amount of thermal energy and can be filled with fluid at a temperature that is generally equal to room temperature or within a range of about 20° C.-30° C. In some embodiments, the balloon 712 is inflated with ambient air and can hold the electrode 715a against the tissue 825. In other embodiments, the balloon 712 is inflated with warm saline. The lesion 804 has a generally semicircular shape. The radius r and depth D can be increased or decreased by decreasing or increasing, respectively, the temperature of the coolant in the cooling channel 753. Additionally or alternatively, the radius r and depth D can be increased or decreased by decreasing or increasing, respectively, the flow rate of the coolant.

Figure 28A:
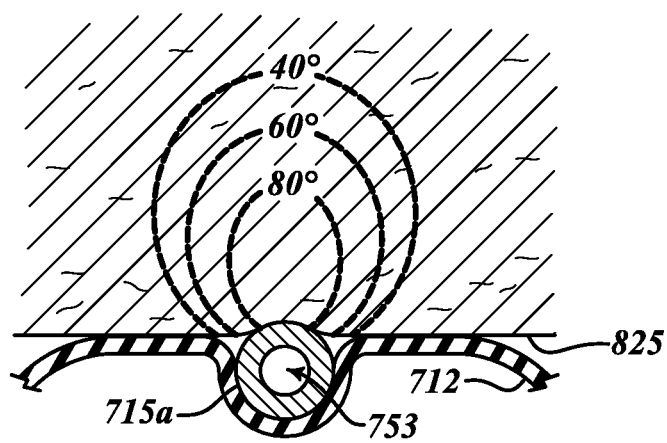
Figure 28B:
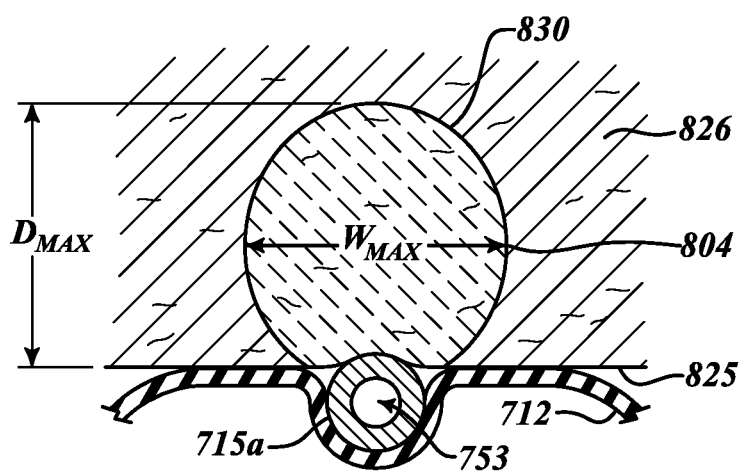

Chilled coolant can be delivered through the balloon 712 to reduce the cross-sectional width of the lesion at the tissue surface 825. FIGS. 28A and 28B show isotherms and a corresponding generally elliptical shaped lesion 804 when a coolant cools the electrode 715a and when a low temperature coolant flows at a low velocity through the balloon 712. The coolant in the balloon 712 absorbs a sufficient amount of thermal energy to protect tissue that contacts or is proximate to the balloon-tissue interface. In some embodiments, including the illustrated embodiment of FIG. 28B, the cross-sectional width of the lesion 804 at the surface 825 is less than a cross-sectional width of the lesion 804 of FIG. 27B at the surface 825. The cross-sectional width of the lesion 804 of FIG. 28B increases with depth to a maximum width $W_{Max}$ and then decreases to the deepest region 830. The maximum width $W_{Max}$ is less than the depth D of the lesion 804. FIG. 28B shows the lesion 804 at the surface 825 having a width that is no more than about 150% of the electrode width.

Figure 29A:
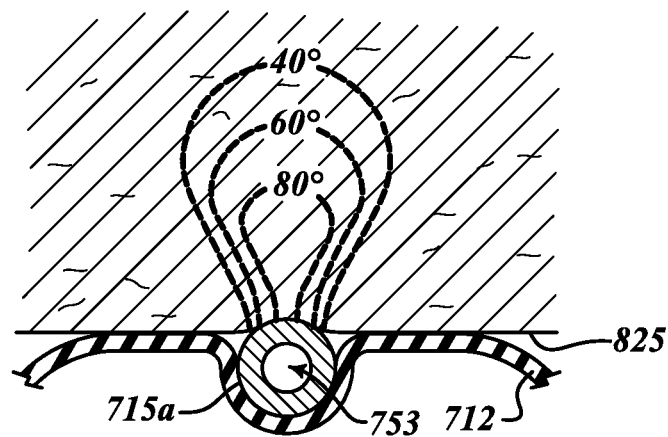
Figure 29B:
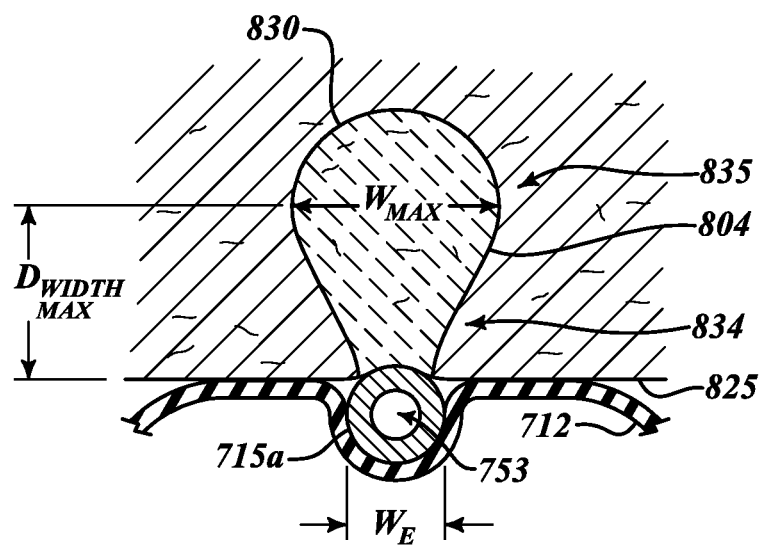

FIGS. 29A and 29B show isotherms and the lesion 804 when a low temperature coolant flows at a high velocity through the balloon 712 or a very low temperature coolant flows at a low velocity through the balloon 712. The somewhat teardrop shaped lesion 804 extends from the tissue surface 825. The width of a shallow or narrowed region 834 of the lesion 804 is about equal to the cross-sectional width $W_E$ of the electrode 715a. Thus, the lesion 804 at the surface 825 has a maximum cross-sectional width that is no more than about 150% of an electrode-tissue interface. This ensures that a minimal amount of surface tissue is damaged. The lesion 804 tapers outwardly from the shallow portion 834 to an enlarged region 835. The lesion cross-sectional width gradually increases with depth to a maximum width $W_{Max}$. The maximum width $W_{Max}$ can be more than about 1 to about 5 times the cross-sectional width at the surface 825. The deepest region 830 of the lesion 804 has a partially circular shape.

Figure 30A:
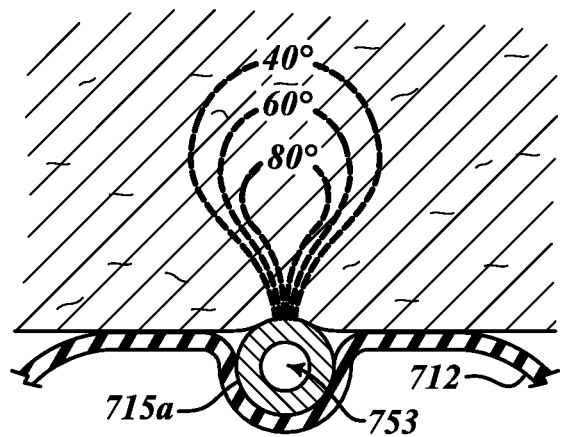
Figure 30B:
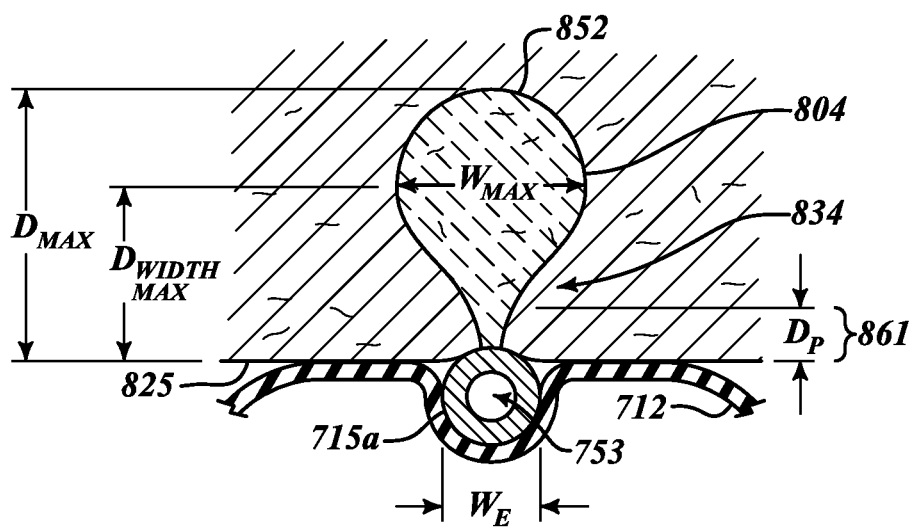

FIGS. 30A and 30B show isotherms and a teardrop shaped lesion 804 that can be formed when a very low temperature coolant flows at a high velocity through the balloon 712. The lesion 804 extends from the tissue surface 825 and has a narrow shallow region 834 that rapidly expands outwardly to a wide deep region 852. The width of the shallow region 834 is less than a width $W_E$ of the electrode 715a. The cross-sectional width rapidly increases with depth to a maximum width $W_{Max}$. Thus, most of the volume of the lesion 804 is deep in the tissue.

Figure 31A:
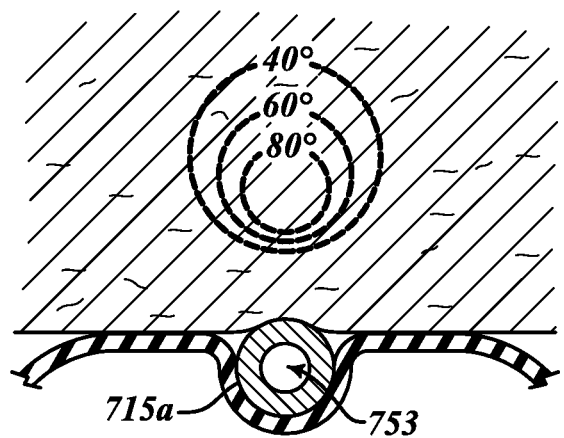
Figure 31B:
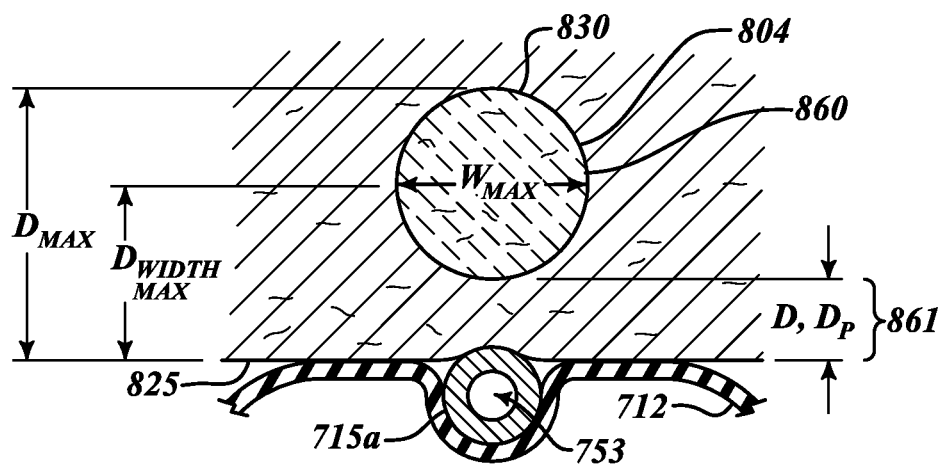

FIGS. 31A and 31B show isotherms and a corresponding circular shaped lesion 804 that can be formed when a very low temperature coolant flows at a very high velocity through the balloon 712. The lesion 804 is disposed at a depth D from the tissue surface 825. The maximum cross-section a width $W_{Max}$ of the lesion 804 is at a depth $D_{Width\ Max}$. The lesion 804 is spaced apart from the electrode-tissue interface and can have different shapes depending on the flow rates and the temperatures of the coolants. Differential cooling can be used to achieve other buried lesion shapes, such as generally elliptical shapes, elongated shapes, or the like.

The $D_{Width\ Max}$ can be selected based on the location of the target region. To damage nerve tissue, the $D_{Width\ Max}$ can be at least about 2 mm to ensure that the lesion includes the nerve tissue and to mitigate or avoid a significant amount of damage to smooth muscle tissue. Such embodiments are well suited for treating an airway wall because the smooth muscle tissue is typically not below a depth of 2 mm. In this manner, the cross-sectional width of the target region can be maximized at a depth deeper than the smooth muscle tissue. The majority, and in some embodiments substantially all, of the lesion will be in tissue which is not smooth muscle tissue, typically lying deeper in the airway wall than the region of smooth muscle tissue. Further, any damage to smooth muscle cells in the airway wall can be less than the amount of damage that, in the absence of damaging nerve tissue, would be required to substantially alter the responsiveness or constriction of the airway, e.g. as a result of asthma, COPD, or other pulmonary disease.

The lesion can be separated from the tissue surface by a protected region in which a significant amount of the tissue is not permanently damaged. FIGS. 31B and 32B show a protected region 861 having a depth $D_P$. Advantageously, because a significant amount of tissue in the protected region 861 is not permanently damaged, tissue functioning can be preserved. The depth $D_P$ can be at least about 1 mm to about 2 mm to ablate nerve tissue.

Figure 32:
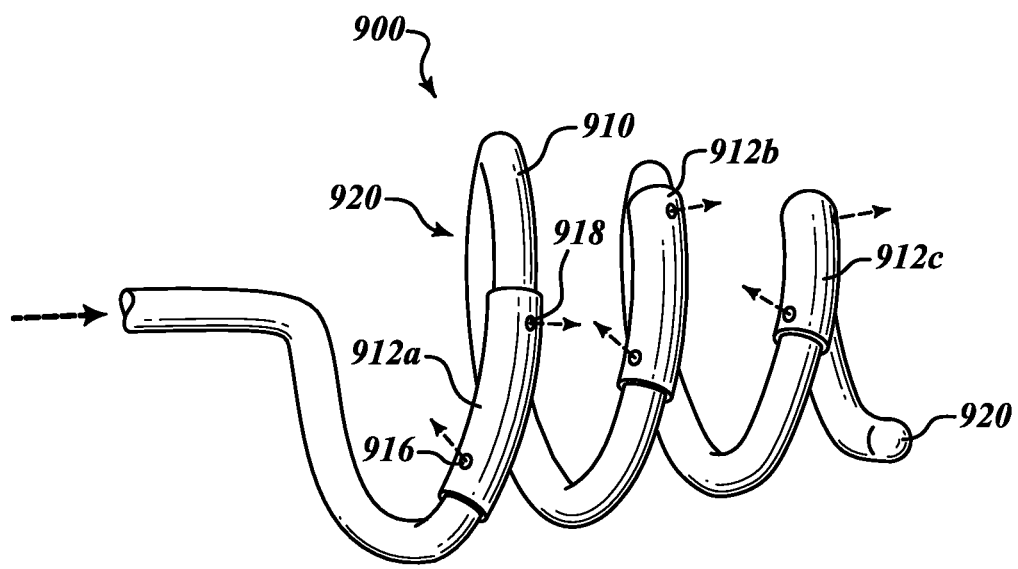
FIG. 32 is a side elevational view of a helical ablation assembly.

FIG. 32 shows a helical ablation assembly 900 that includes a curved (illustrated as helical-shaped) main body 910 (shown tapered to match an airway taper) and electrodes 912a, 912b, 912c (collectively "912"). Optionally, one or more pressure reducing elements can be positioned within the body 910 to act as Joule-Thomson throttle to reduce the temperature of the coolant.

The electrodes 912 can be generally similar to each other and, accordingly, the description of one electrode applies equally to the others, unless indicated otherwise. The electrode 912a includes a plurality of vents 916, 918. Coolant, represented by arrows, can flow out of the vents 916, 918. The electrode 912a can be coupled to an exterior surface of the main body 910. This allows the electrodes 912 to protrude outwardly a sufficient distance to physically contact with tissue. Electrodes 912 are arranged to create lesions which are circumferentially offset from one another, but which have some circumferential overlaps at their edges, i.e., an imaginary line drawn longitudinally down the airway through the end of one lesion will intersect the end of the next lesion. Because electrodes 912 are spaced apart along the helical body 910, the lesions they create are also spaced apart axially in the airway, thus reducing the possibility of stenosis.

The main body 910 may comprise a flexible and electrically conductible material, such as Nitinol, that can be shaped into a helical or corkscrew shape when activated. A warm fluid can be delivered through the main body 910, causing the body 910 to move from a delivery configuration (e.g., a straight configuration) to a deployed configuration (e.g., a corkscrew configuration or a helical configuration). In other embodiments, the main body 910 can be biased towards the deployed configuration and can be delivered out of a sleeve or working lumen to assume the deployed configuration. The ablation assembly 900 can be pulled proximally into the sleeve or working lumen to return the ablation assembly 900 to a delivery configuration. In other embodiments, tensioners, pull wires, pull rods, or the like can be used to cause the main body 910 to assume different configurations.

Optionally, a balloon can be positioned through an interior region 920. A generally conically-shaped balloon, cylindrical balloon, hot dog shaped balloon, or other suitably shaped balloon may be insertable into the interior region 920.

Figure 33:
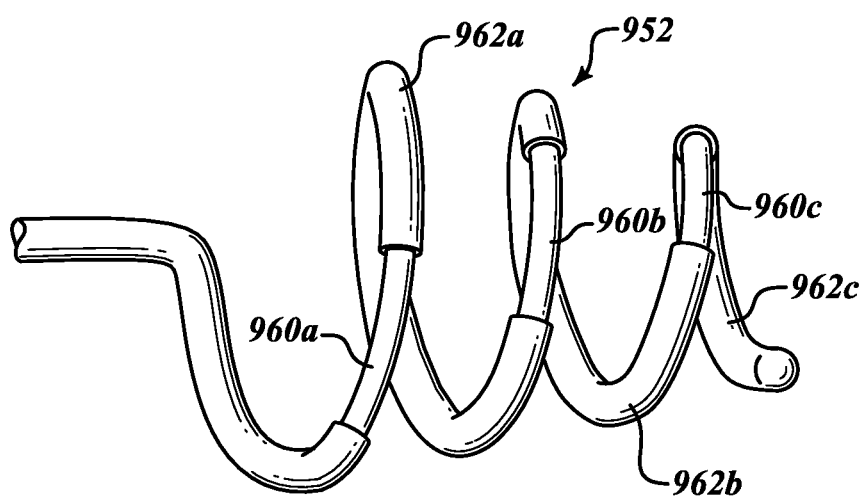
FIG. 33 is a side elevational view of another helical ablation assembly.

FIG. 33 shows a helical ablation assembly 952 made of a tubular conductive inner member having with series of spaced-apart exposed sections forming electrodes 960a, 960b, 960c (collectively "960") with an insulative cover over the intervening sections to create insulated regions 962a, 962b, 962c. A coolant can be circulated through the ablation assembly 520 to cool electrodes 960. To provide additional tissue cooling, the coolant can optionally be delivered out of vents (not shown) in the inner tubular member and/or the insulative cover.

Figure 34:
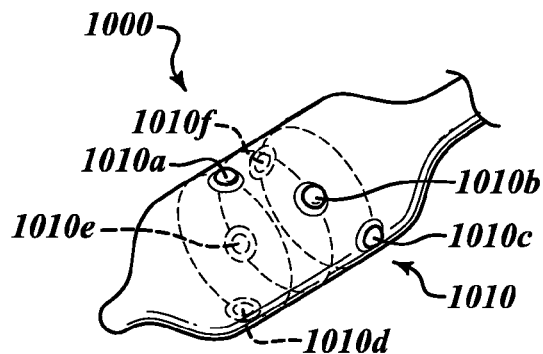
FIG. 34 is an isometric view of an ablation assembly with spaced apart electrodes.
Figure 35:
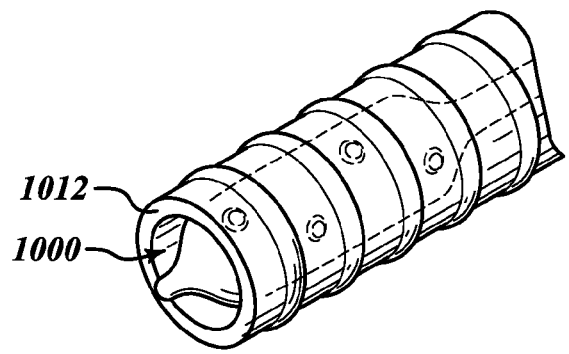
FIG. 35 is an isometric view of the ablation assembly of FIG. 34 positioned in airway body lumen.
Figure 36:
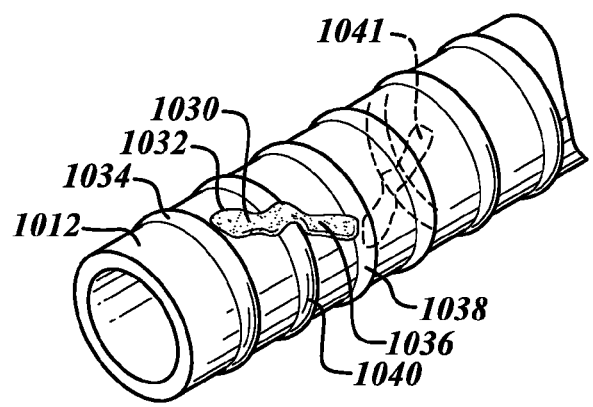
FIG. 36 is an isometric view of lesions formed by the ablation assembly of FIG. 34.

FIG. 34 shows an ablation assembly 1000 that includes an array of spaced apart bipolar electrodes 1010a-f (collectively "1010"). The electrodes are arranged in pairs of opposite polarity, such that lesions are created diagonally between each bipolar pair. The electrodes 1010 can form oblique lesions that traverse cartilaginous rings. As shown in FIG. 35, the ablation assembly 1000 is positioned within an airway 1012. The electrodes 1010 are positioned between the rings. Electrodes 1010a-c can create a lesion 1030 of FIG. 36. An end 1032 of the lesion 1030 is proximate to a ring 1034. An opposing end 1036 is adjacent to a ring 1038. The ends 1032, 1036 are displaced from one another axially along the airway 1012. As shown in FIG. 36, the axial displacement of the ends 1032, 1036 is significantly greater than the circumferential distance between the ends 1032, 1036. In certain procedures, the distance between the ends 1032, 1036 is at least one millimeter, 5 millimeters, 10 millimeters. In some embodiments, the axial distance between the ends 1032, 1036 is greater than the distance between adjacent cartilaginous rings. This ensures that the lesions traverse the rings.

A central section of the lesion 1030 of FIG. 36 traverses a ring 1040 between the rings 1034, 1038. Electrodes 1010d, 1010e, 1010f on the back side of the ablation assembly 1000 form a lesion 1041. The illustrated lesions 1041, 1030 are on opposite sides and at different axial locations along the airway.

The electrodes 1010 can protrude outwardly a sufficient distance to interact with the airway tissue to keep the electrodes 1010 located between cartilaginous rings. When operating in bipolar mode, lesions are formed and traverse the rings. After forming the lesions, the catheter can be pulled proximally or pushed distally and used to form axially offset lesions. Additionally or alternatively, the catheter can be rotated to form oblique lesions at different angular positions along the airway 1012. The lesions of FIG. 36 are illustrated as continuous lesions. In other embodiments, lesions can comprise a plurality of discrete spaced-apart lesions. For example, the lesion 1030 can comprise an array of spaced-apart lesions.

Figure 37:
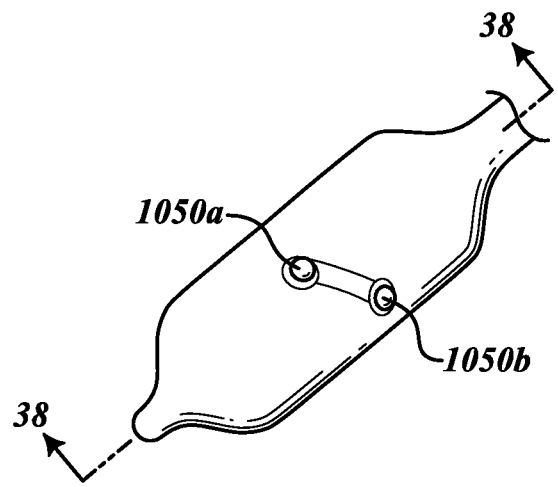
FIG. 37 is an isometric view of an ablation assembly with coolant cooled electrodes.
Figure 38:
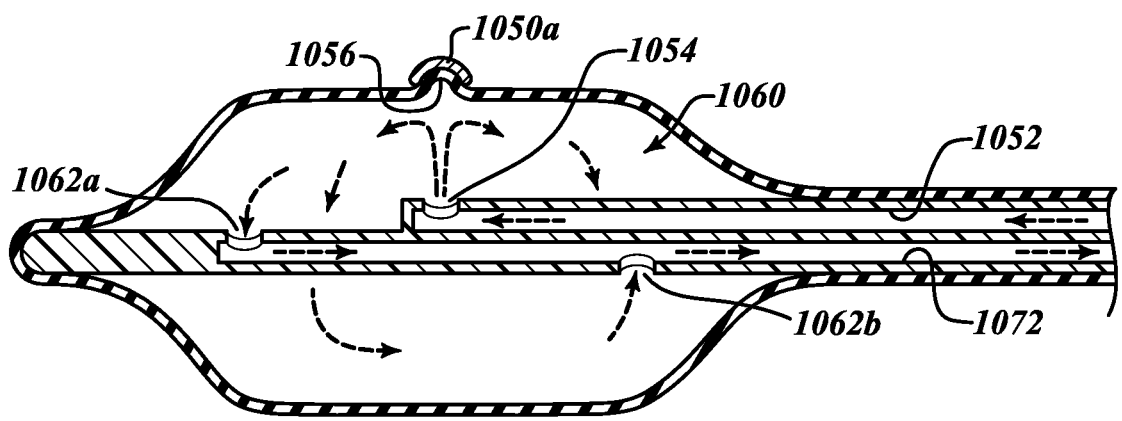
FIG. 38 is a cross-sectional view of an ablation assembly taken along a line 38-38 of FIG. 37.

FIGS. 37 and 38 show circumferentially offset and axially spaced-apart electrodes 1050a, 1050b cooled by an internal jet. A coolant flows through a delivery lumen 1052 and exits a port 1054. The jet of coolant flows along an open cooling channel 1056 to cool the electrode 1050a. The coolant exits a chamber 1060 via outlet ports 1062a, 1062b. The coolant flows along a return lumen 1072. The electrodes 1050a, 1050b can be operated either in a monopolar mode or in bipolar mode while being cooled.

Figure 39A:
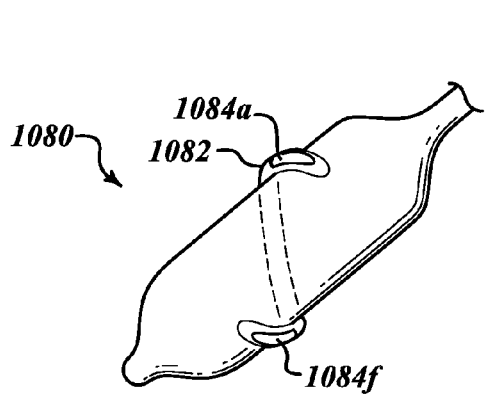
FIG. 39A is an isometric view of an ablation assembly with a curved energy emitter.
Figure 39B:
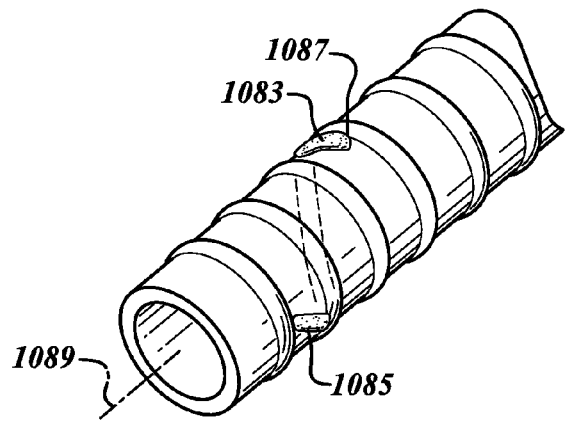
FIG. 39B is an isometric view of a vessel treated by the ablation assembly of FIG. 39A.
Figure 40A:
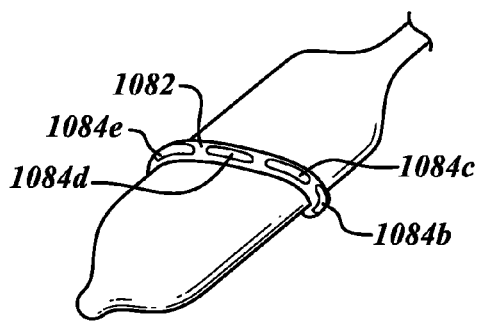
FIG. 40A is another isometric view of the ablation assembly of FIG. 39A.
Figure 40B:
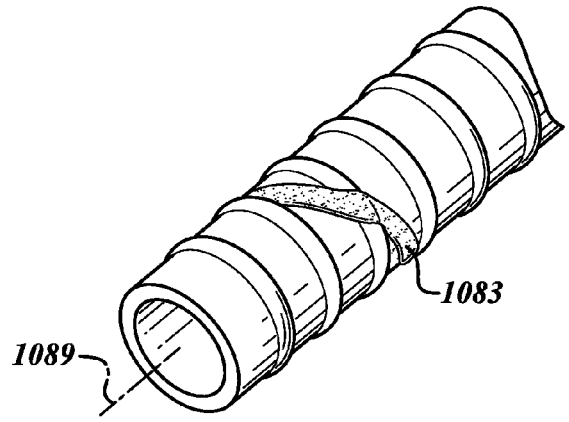
FIG. 40B is an isometric view of the vessel treated by the ablation assembly of FIG. 40A.

FIGS. 39A-40B show an ablation assembly 1080 that includes an energy emitter in the form of an electrode assembly 1082. The electrode assembly 1082 includes an array of electrodes 1084a-f (collectively "1084") that can form a lesion 1083 (FIGS. 39B and 40B). A wide range of different types of serpentine, curved, zigzag, z-shaped, or other various configurations. The illustrated lesion 1083 has a generally helical shape and traverses multiple cartilaginous rings. The ablation assembly 1080 can have any number of these types of electrode assemblies 1082. For example, a pair of helical ablation assemblies 1082 can be positioned on the outside of the ablation assembly 1080.

The illustrated lesion 1083 is continuous and has ends 1085, 1087 that are spaced axially apart along a long axis 1089 of the airway. The ends 1085, 1087 are also angularly offset from one another. As shown in FIGS. 39B and 40B, the distance between the ends 1085, 1087 along the axis 1089 is greater than the distance between adjacent rings. As such, the lesion 1083 traverses multiple rings.

The electrodes 1084 can be close together to form the generally contiguous lesion 1083. In other embodiments, the distance between the electrodes 1084 can be increased to provide a plurality of spaced-apart lesions. The spaced-apart lesions can be arranged to have a shape similar to the lesion 1083 but other shapes and lesion patterns are possible.

Figure 41:
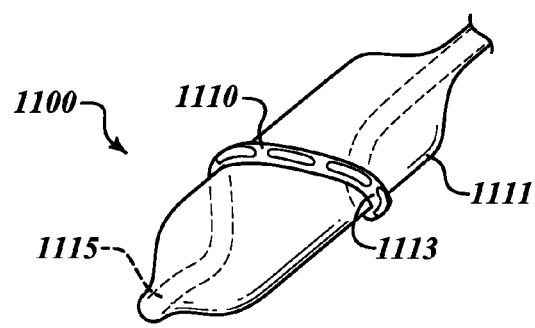
FIG. 41 is an isometric view of an ablation assembly, in accordance with another embodiment.

FIG. 41 shows an ablation assembly 1100 with an electrode assembly 1110 that wraps around a balloon 1111. The electrode assembly 1110 comprises a tube 1113 suitable for containing a coolant and has a distal end 1115 in communication with the interior of the balloon 1111. Electrodes are mounted, adhered, painted, or otherwise coupled to the exterior of the tube 1113. In this way, coolant may be delivered through the catheter to the interior of the balloon 1111 to inflate the balloon 1111, from which the coolant flows through the tube 1113 to cool the electrodes. Alternatively, the coolant can cool the electrodes and subsequently the balloon 1111. The electrode assembly 1110 and balloon 1111 can provide differential cooling to form shaped lesions.

Figure 42:
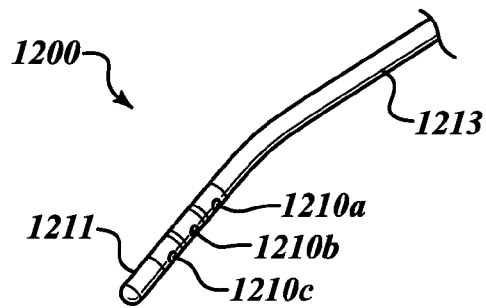
FIG. 42 is an isometric view of an ablation assembly in a delivery configuration.
Figure 43:
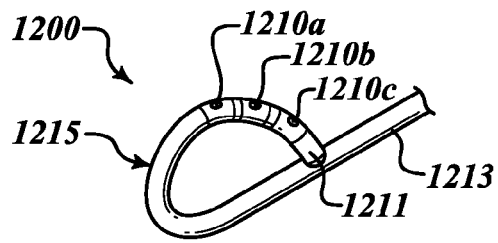
FIG. 43 is an isometric view of the ablation assembly of FIG. 42 in deployed configuration.
Figure 43A:
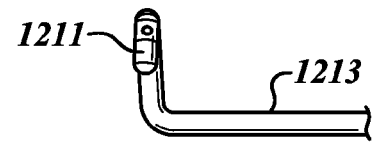
FIG. 43A is a side elevational view of the ablation assembly of FIG. 43.
Figure 44:
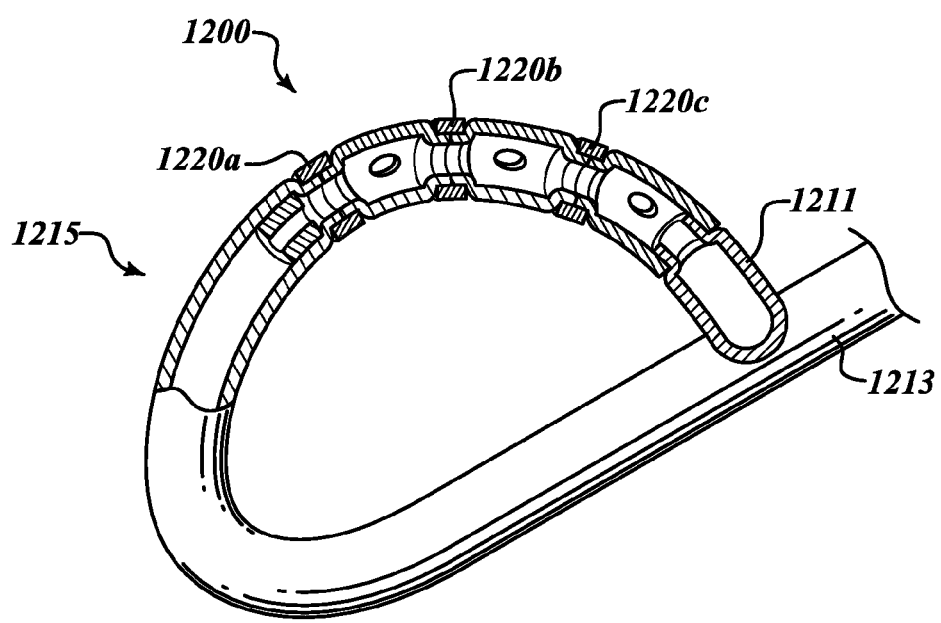
FIG. 44 is a cross-sectional view of a distal section of the ablation assembly of FIG. 43.

FIGS. 42-44 show an ablation assembly 1200 movable from a delivery configuration (FIG. 42) to a deployed configuration (FIGS. 43 and 44). In the delivery configuration, a distal portion 1211 of ablation assembly 1200 is linearized with the proximal portion of the catheter shaft 1213 so as to be generally aligned with a longitudinal axis of the airway or other body lumen into which it is being inserted. In the deployed configuration, the distal portion 1211 of the ablation assembly 1200 is deflected or deformed such that it forms a loop 1215 which lies in a plane which is transverse to the longitudinal axis of the proximal extremity of the catheter shaft 1213. In this way, the loop 1215 may extend around the inner wall of the airway to position electrodes 1220 at a series of circumferentially spaced-apart locations thereon.

In the deployed configuration, the loop may be helical or may lie in a plane disposed at an oblique angle relative to the longitudinal axis of the catheter shaft 1213 such that electrodes 1220 are positioned at axially separated locations along the airway wall. Loop 1215 may be deployed using a variety of well known mechanisms. For example, a pull wire may extend slidably through a lumen in the catheter shaft and be fixed at a point near the distal end such that tension on the pull wire deploys the loop 1215 in the desired configuration. Alternatively, the distal portion of the catheter may be preformed in the deployed configuration and may be resilient such that the distal portion may be constrained within a sheath during delivery, then released by retracting the sheath such that the distal portion resumes the deployed configuration.

Vents 1210a-1210c (collectively "1210") provide direct coolant cooling of tissue. Electrodes 1220a-c (collectively "1120") are operated independently to form discrete lesions or operated together to form one aggregate electrode for forming a continuous lesion. The electrodes 1220 can be positioned between two cartilage rings in the proximal main stem bronchii to treat about one-third of the circumference of the airway (e.g., anterior medial or anterior lateral region of the airway). The electrodes 1220 are then repositioned distally between two distal cartilaginous rings to treat the other third anterior lateral or anterior medial portion of the airway wall. The electrodes 120 are moved again to treat the posterior third of the airway, such as membrane portion. Coolant can be delivered through the vents 1210 to cool the tissue. The ablation assembly 1200 can be used to sequentially ablate different sections of vessels and can be moved distally and proximally to provide sufficient spacing between lesions to mitigate scar tissue or stenosis, if any.

The delivery devices disclosed herein can treat the digestive system, nervous system, vascular system, or other systems. For example, the elongate assemblies, intra-luminal catheters, and delivery devices disclosed herein can be delivered through blood vessels to treat the vascular system. The treatment systems and its components disclosed herein can used as an adjunct during another medical procedure, such as minimally invasive procedures, open procedures, semi-open procedures, or other surgical procedures (e.g., lung volume reduction surgery) that provide access to a desired target site. Various surgical procedures on the chest may provide access to lung tissue. Access techniques and procedures used to provide access to a target region can be performed by a surgeon and/or a robotic system. Those skilled in the art recognize that there are many different ways that a target region can be accessed.

Guidewires, delivery sheaths, optical instruments, introducers, trocars, biopsy needles, or other suitable medical equipment can be used to steer the delivery apparatuses. If the target treatment site is at a distant location in the patient (e.g., a treatment site near the lung root 24 of FIG. 1), a wide range of instruments and techniques can be used to access the site. The flexible elongated assemblies can be easily positioned within the subject using, for example, steerable delivery devices, such as endoscopes and bronchoscopes, as discussed above.

Semi-rigid or rigid elongated assemblies can be delivered using trocars, access ports, rigid delivery sheaths using semi-open procedures, open procedures, or other delivery tools/procedures that provide a somewhat straight delivery path. Advantageously, the semi-rigid or rigid elongated assemblies can be sufficiently rigid to access and treat remote tissue, such as the vagus nerve, nerve branches, nerve fibers, and/or nerve trunks along the airways, without delivering the elongated assemblies through the airways. The embodiments and techniques disclosed herein can be used with other procedures, such as bronchial thermoplasty.

Unless the context requires otherwise, throughout the specification and claims which follow, the word "comprise" and variations thereof, such as "comprises" and "comprising" are to be construed in an open, inclusive sense, that is, as "including but not limited to."

The various embodiments described above can be combined to provide further embodiments. These and other changes can be made to the embodiments in light of the above-detailed description. The embodiments, features, systems, devices, materials, methods and techniques described herein may, in some embodiments, be similar to any one or more of the embodiments, features, systems, devices, materials, methods and techniques described in of application Ser. No. 12/463,304 filed on May 8, 2009; U.S. application Ser. No. 12/913,702 filed on Oct. 27, 2010; U.S. Provisional Patent Application No. 61/255,367 filed Oct. 27, 2009; and U.S. Provisional Patent Application No. 61/260,348 filed Nov. 11, 2009. Each of these applications is incorporated herein by reference in its entirety. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned U.S. patent application Ser. No. 12/463,304 and U.S. application Ser. No. 12/913,702 filed on Oct. 27, 2010. For example, the apparatuses of disclosed in U.S. patent application Ser. No. 12/463, 304 and U.S. application Ser. No. 12/913,702 filed on Oct. 27, 2010 may incorporate the electrodes or other features disclosed herein.

In addition, the embodiments, features, systems, delivery devices, materials, methods and techniques described herein may, in certain embodiments, be applied to or used in connection with any one or more of the embodiments, features, systems, devices, materials, methods and techniques disclosed in the above-mentioned of application Ser. No. 12/463, 304 filed on May 8, 2009; U.S. application Ser. No. 12/913, 702 filed on Oct. 27, 2010; U.S. Provisional Patent Application No. 61/255,367 filed Oct. 27, 2009; and U.S. Provisional Patent Application No. 61/260,348 filed Nov. 11, 2009.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating a subject, comprising:
positioning an ablation assembly with respect to an airway of the subject, wherein the ablation assembly comprises a plurality of energy emitting elements spaced circumferentially about from each other about and axially from each other along a longitudinal axis of the ablation assembly; and
causing energy to be emitted from the ablation assembly to target regions of the airway to create a plurality of axially spaced apart discrete lesions, each lesion extending only partially around a circumference of the airway, wherein an arc length about the circumference of at least one lesion at least partially overlaps with an arc length about the circumference of at least one other lesion of the plurality of lesions.

2. The method of claim 1, further comprising causing tissue to be heated at a depth greater than about 2 mm to cause cell death while maintaining tissues at a depth less than 2 mm in the airway wall at a temperature below that at which cell death occurs.

3. The method of claim 1, further comprising causing coolant to be delivered through the ablation assembly to cool tissues of the airway at a depth less than 2 mm.

4. A method of treating a subject, comprising:
moving an energy emitter of a delivery device along an airway of the subject, wherein the energy emitter comprises a plurality of energy emitting electrodes spaced circumferentially and axially from each other along a longitudinal axis of the ablation assembly;
positioning at least one electrode of the energy emitter between cartilaginous rings of the airway; and
causing energy to be emitted from the at least one electrode to target regions of the airway at axially separated locations along a long axis of the airway to form a plurality of inter-cartilaginous lesions, each lesion extending only partially around a circumference of the airway, and wherein at least some of the lesions overlap circumferentially about a long axis of the airway.

5. The method of claim 4, further comprising causing the wall of the airway to be cooled to protect interior tissue of the airway.

6. The method of claim 4, wherein one of the lesions lies in a first imaginary plane orthogonal to the long axis of the airway and the another lesion lies in a second imaginary plane orthogonal to the long axis of the airway, wherein the first imaginary plane and the second imaginary plane are axially spaced apart along the long axis of the airway.

7. The method of claim 4, further comprising causing a wall of the airway to be cooled while causing the energy to be emitted to limit or prevent cell death in tissue located between a nerve trunk and the energy emitter.

8. The method of claim 4, further comprising causing tissue to be heated at a depth of at least about 2 mm to cause cell death while maintaining tissues at a depth less than 2 mm in the airway wall at a temperature below that at which cell death occurs.

9. The method of claim 4, further comprising causing coolant to be delivered through the electrode while causing energy to be emitted from the electrode.

10. A method of treating tissue, comprising:
positioning an ablation assembly in a lumen of an airway of a subject, wherein the ablation assembly comprises a plurality of electrodes spaced circumferentially and axially from each other along a longitudinal axis of the ablation assembly; and
causing energy to be delivered to tissue of the airway using e the plurality of electrodes of the ablation assembly positioned near an inner surface of the airway, wherein the energy damages target regions axially separated along the airway thereby defining lesions having a maximum cross-sectional width radially spaced from the inner surface of the airway.

11. The method of claim 10, further comprising positioning the plurality of the electrodes between cartilaginous rings while causing energy to be delivered.

12. The method of claim 10, further comprising causing energy to be delivered to form at least one helical-shaped lesion or spiral-shaped lesion.

13. The method of claim 10, wherein the maximum cross-sectional width of at least one target region is at a depth at least 2 mm from the inner surface of the airway contacting the ablation assembly.

14. The method of claim 10, further comprising causing tissue to be damaged at one of the target regions such that the cross-sectional width of the damaged tissue is maximized at a depth deeper than a region of smooth muscle tissue in the tissue.

15. The method of claim 10, wherein causing energy to be delivered comprises damaging at least one target region such that a majority of that target region is outside a region of smooth muscle tissue of the tissue.

16. The method of claim 15, wherein most of a volume of the damaged tissue is outside of a region of smooth muscle tissue.

17. A method for treating a subject, comprising:
positioning an ablation assembly within an airway of the subject, wherein the ablation assembly comprises a plurality of energy emitting elements spaced circumferentially and axially from each other along a longitudinal axis of the ablation assembly; and
causing energy to be delivered from the ablation assembly to form a plurality of lesions, each lesion being axially offset with respect to one another in a direction of a long axis of the airway, wherein each lesion is at least partially adjacent to or overlaps another lesion in a circumferential direction of the airway.

18. The method of claim 17, wherein each lesion is separated by a distance of at least 5 mm as measured along the long axis of the ablation assembly.

19. The method of claim 17, further comprising causing energy to be delivered to form a continuous lesion that has a spiral shape or a helical shape.

20. The method of claim 17, further comprising causing a discontinuous lesion to be formed, the lesion having a spiral shape or a helical shape.

21. The method of claim 17, wherein the at least one lesion comprises a plurality of spaced apart lesions positioned about the airway.

* * * * *